US00RE44437E

(19) United States
(12) Reissued Patent
Chan-Hui et al.

(10) Patent Number: US RE44,437 E
(45) Date of Reissued Patent: Aug. 13, 2013

(54) METHODS FOR DETECTING RECEPTOR COMPLEXES COMPRISING PI3K

(75) Inventors: Po-Ying Chan-Hui, Bellevue, WA (US); Rajiv Dua, Manteca, CA (US); Ali Mukherjee, Millbrae, CA (US); Sailaja Pidaparthi, Cupertino, CA (US); Hossein Salimi-Moosavi, Newbury Park, CA (US); Yining Shi, Freemont, CA (US); Sharat Singh, Rancho Santa Fe, CA (US)

(73) Assignee: Monogram Biosciences, Inc., South San Francisco, CA (US)

(21) Appl. No.: 13/352,705

(22) Filed: Jan. 18, 2012

Related U.S. Patent Documents

Reissue of:
(64) Patent No.: 7,648,828
Issued: Jan. 19, 2010
Appl. No.: 11/041,073
Filed: Jan. 21, 2005

U.S. Applications:
(63) Continuation of application No. 10/813,417, filed on Mar. 30, 2004, now abandoned, which is a continuation-in-part of application No. 10/623,057, filed on Jul. 17, 2003, now Pat. No. 7,105,308.

(60) Provisional application No. 60/459,888, filed on Apr. 1, 2003, provisional application No. 60/494,482, filed on Aug. 11, 2003, provisional application No. 60/508,034, filed on Oct. 1, 2003, provisional application No. 60/512,941, filed on Oct. 20, 2003, provisional application No. 60/523,258, filed on Nov. 18, 2003.

(51) Int. Cl.
*G01N 33/574* (2006.01)

(52) U.S. Cl.
USPC ..... 435/7.23; 435/7.1

(58) Field of Classification Search
None
See application file for complete search history.

(56) References Cited

U.S. PATENT DOCUMENTS

| | | | |
|---|---|---|---|
| 4,331,590 | A | 5/1982 | Bocuslaski |
| 4,650,750 | A | 3/1987 | Giese |
| 4,709,016 | A | 11/1987 | Giese |
| 4,772,550 | A | 9/1988 | Greenquist |
| 4,780,421 | A | 10/1988 | Kameda |
| 4,891,324 | A | 1/1990 | Pease |
| 4,968,603 | A | 11/1990 | Slamon |
| 5,057,412 | A | 10/1991 | Rabin |
| 5,108,896 | A | 4/1992 | Philo |
| 5,192,660 | A | 3/1993 | Reed-Gitomer |
| 5,340,716 | A | 8/1994 | Ullman |
| 5,360,819 | A | 11/1994 | Giese |
| 5,436,128 | A | 7/1995 | Harpold |
| 5,470,705 | A | 11/1995 | Grossman |
| 5,480,968 | A | 1/1996 | Kraus |
| 5,494,793 | A | 2/1996 | Schindele |
| 5,514,543 | A | 5/1996 | Grossman |
| 5,516,636 | A | 5/1996 | McCapra |
| 5,516,931 | A | 5/1996 | Giese |
| 5,536,834 | A | 7/1996 | Singh |
| 5,565,324 | A | 10/1996 | Still |
| 5,578,498 | A | 11/1996 | Singh |
| 5,580,732 | A | 12/1996 | Grossman |
| 5,602,273 | A | 2/1997 | Giese |
| 5,604,104 | A | 2/1997 | Giese |
| 5,610,020 | A | 3/1997 | Giese |
| RE35,491 | E | 4/1997 | Cline |
| 5,616,719 | A | 4/1997 | Davalian |
| 5,624,800 | A | 4/1997 | Grossman |
| 5,646,001 | A | 7/1997 | Terstappen |
| 5,650,270 | A | 7/1997 | Giese |

(Continued)

FOREIGN PATENT DOCUMENTS

| | | |
|---|---|---|
| EP | 0484027 | 5/1992 |
| WO | WO93/06121 | 4/1993 |

(Continued)

OTHER PUBLICATIONS

Biernat, W. et al., "Quantitative HER2 levels and steroid receptor expression in primary breast cancers and in matched brain metastases," 2012 J. Clin. Oncol. 30 (Jun. 20 Suppl.): Abstract 603.
Biernat, W. et al., "Quantitative HER2 levels and steroid receptor expression in primary breast cancers and in matched brain metastases," American Society of Clinical Oncology (ASCO) Annual Meeting, May 31-Jun. 4, 2012; Chicago, IL (Poster 603).
Huang, W. et al., "Quantitative HER2 measurement and PI3K mutation profile in matched primary and metastatic breast cancer tissues," 2012 J. Clin. Oncol. 30 (Jun. 20 Suppl.): Abstract 614.
Huang, W. et al., "Quantitative HER2 measurement and PI3K mutation profile in matched primary and metastatic breast cancer tissues," American Society of Clinical Oncology (ASCO) Annual Meeting, May 31-Jun. 4, 2012, Chicago, IL (Poster 614).

(Continued)

*Primary Examiner* — Mark Halvorson
(74) *Attorney, Agent, or Firm* — Kilpatrick Townsend & Stockton LLP

(57) ABSTRACT

The invention is directed to a new class of biomarker in patient samples comprising dimers of ErbB cell surface membrane receptors. In one aspect, the invention includes a method of determining the status of a disease or healthful condition by correlating such condition to amounts of one or more dimers of ErbB cell surface membrane receptors measured directly in a patient sample, in particular a fixed tissue sample. In another aspect, the invention includes a method of determining a status of a cancer in a specimen from an individual by correlating measurements of amounts of one or more dimers of ErbB cell surface membrane receptors in cells of the specimen to such status, including presence or absence of a pre-cancerous state, presence or absence of a cancerous state, prognosis of a cancer, or responsiveness to treatment. Preferably, methods of the invention are implemented by using sets of binding compounds having releasable molecular tags that are specific for multiple components of one or more types of receptor dimers. After binding, molecular tags are released and separated from the assay mixture for analysis.

20 Claims, 36 Drawing Sheets

(56) References Cited

U.S. PATENT DOCUMENTS

| | | | |
|---|---|---|---|
| 5,703,222 | A | 12/1997 | Grossman |
| 5,705,622 | A | 1/1998 | McCapra |
| 5,709,994 | A | 1/1998 | Pease |
| 5,721,099 | A | 2/1998 | Still |
| 5,756,726 | A | 5/1998 | Hemmi |
| 5,766,481 | A | 6/1998 | Zambias |
| 5,777,096 | A | 7/1998 | Grossman |
| 5,789,172 | A | 8/1998 | Still |
| 5,800,999 | A | 9/1998 | Bronstein |
| 5,804,396 | A | 9/1998 | Plowman |
| 5,807,675 | A | 9/1998 | Davalian |
| 5,807,682 | A | 9/1998 | Grossman |
| 5,843,655 | A | 12/1998 | McGall |
| 5,843,666 | A | 12/1998 | Akhavan-Tafti |
| 5,846,839 | A | 12/1998 | Gallop |
| 5,849,878 | A | 12/1998 | Cantor et al. |
| 5,874,542 | A | 2/1999 | Rockwell |
| 5,886,238 | A | 3/1999 | Schaap |
| 5,952,654 | A | 9/1999 | Giese |
| 5,958,202 | A | 9/1999 | Regnier |
| 5,968,511 | A | 10/1999 | Akita |
| 5,986,076 | A | 11/1999 | Rothschild |
| 5,989,871 | A | 11/1999 | Grossman |
| 6,001,573 | A | 12/1999 | Poelant |
| 6,001,579 | A | 12/1999 | Still |
| 6,001,583 | A | 12/1999 | Margolis |
| 6,027,890 | A | 2/2000 | Ness |
| 6,248,546 | B1 | 6/2001 | Khosravi |
| 6,251,581 | B1 | 6/2001 | Ullman |
| 6,312,893 | B1 | 11/2001 | Van Ness |
| 6,322,980 | B1 | 11/2001 | Singh |
| 6,331,530 | B1 | 12/2001 | Breslow |
| 6,335,201 | B1 | 1/2002 | Allbritton |
| 6,346,384 | B1 | 2/2002 | Pollner |
| 6,346,529 | B1 | 2/2002 | Floyd |
| 6,358,682 | B1 | 3/2002 | Jaffee |
| 6,365,362 | B1 | 4/2002 | Terstappen |
| 6,368,874 | B1 | 4/2002 | Gallop |
| 6,383,740 | B2 | 5/2002 | Collins |
| 6,388,063 | B1 | 5/2002 | Plowman |
| 6,417,168 | B1 | 7/2002 | Greene et al. |
| 6,489,116 | B2 | 12/2002 | Wagner |
| 6,514,700 | B1 | 2/2003 | Singh |
| 6,545,102 | B1 | 4/2003 | Akhavan-Tafti et al. |
| 6,558,928 | B1 | 5/2003 | Landegren |
| 6,573,043 | B1 | 6/2003 | Cohen |
| 6,627,196 | B1 | 9/2003 | Baughman |
| 6,627,400 | B1 | 9/2003 | Singh et al. |
| 6,630,296 | B2 | 10/2003 | Xue et al. |
| 6,630,318 | B1 | 10/2003 | Margolis |
| 6,649,351 | B2 | 11/2003 | Matray et al. |
| 6,673,550 | B2 | 1/2004 | Matray et al. |
| 6,682,887 | B1 | 1/2004 | Singh |
| 6,686,152 | B2 | 2/2004 | Singh et al. |
| 6,727,072 | B2 | 4/2004 | Spaulding |
| 6,770,439 | B2 | 8/2004 | Singh et al. |
| 6,818,399 | B2 | 11/2004 | Singh et al. |
| 6,846,645 | B2 | 1/2005 | Xue et al. |
| 6,852,544 | B2 | 2/2005 | Aebersold et al. |
| 6,916,612 | B2 | 7/2005 | Singh et al. |
| 6,949,347 | B2 | 9/2005 | Singh et al. |
| 6,955,874 | B2 | 10/2005 | Singh et al. |
| 7,001,725 | B2 | 2/2006 | Singh et al. |
| 7,037,654 | B2 | 5/2006 | Chenna et al. |
| 7,041,459 | B2 | 5/2006 | Singh et al. |
| 7,045,311 | B2 | 5/2006 | Ciambrone et al. |
| 7,105,308 | B2 | 9/2006 | Chan-Hui et al. |
| 7,135,300 | B2 | 11/2006 | Chan-Hui et al. |
| 7,160,735 | B2 | 1/2007 | Dehlinger et al. |
| 7,217,531 | B2 | 5/2007 | Singh et al. |
| 7,255,999 | B2 | 8/2007 | Singh et al. |
| 7,279,585 | B2 | 10/2007 | Singh et al. |
| 7,312,034 | B2 | 12/2007 | Virgos et al. |
| 7,358,052 | B2 | 4/2008 | Singh |
| 7,402,397 | B2 | 7/2008 | Chan-Hui et al. |
| 7,402,398 | B2 | 7/2008 | Pidaparthi et al. |
| 7,402,399 | B2 | 7/2008 | Mukherjee et al. |
| 7,537,938 | B2 | 5/2009 | Kirakossian et al. |
| 7,648,828 | B2 | 1/2010 | Chan-Hui et al. |
| 7,771,929 | B2 | 8/2010 | Singh et al. |
| 7,939,267 | B2 | 5/2011 | Moore et al. |
| 8,198,031 | B2 | 6/2012 | Chan-Yui et al. |
| 8,247,180 | B2 | 8/2012 | Pidaparthi et al. |
| 2002/0037542 | A1 | 3/2002 | Albritton |
| 2002/0045738 | A1 | 4/2002 | Singh et al. |
| 2002/0058263 | A1 | 5/2002 | Singh et al. |
| 2002/0064779 | A1 | 5/2002 | Landegren et al. |
| 2002/0172984 | A1 | 11/2002 | Holland |
| 2003/0092012 | A1 | 5/2003 | Chenna et al. |
| 2003/0170734 | A1 | 9/2003 | Williams et al. |
| 2003/0175747 | A1 | 9/2003 | Singh |
| 2003/0190689 | A1 | 10/2003 | Crosby |
| 2003/0203408 | A1 | 10/2003 | Williams et al. |
| 2003/0207300 | A1 | 11/2003 | Matray et al. |
| 2003/0207403 | A1 | 11/2003 | Paszty |
| 2003/0235832 | A1 | 12/2003 | Chenna et al. |
| 2004/0018528 | A1 | 1/2004 | Morimoto |
| 2004/0018562 | A1 | 1/2004 | Rouhani |
| 2004/0023288 | A1 | 2/2004 | Ridder |
| 2004/0029139 | A1 | 2/2004 | Singh |
| 2004/0029194 | A1 | 2/2004 | Parish |
| 2004/0033542 | A1 | 2/2004 | Frackelton |
| 2004/0067498 | A1 | 4/2004 | Chenna et al. |
| 2004/0091850 | A1 | 5/2004 | Boone et al. |
| 2004/0106161 | A1 | 6/2004 | Bossenmaier et al. |
| 2004/0157271 | A1 | 8/2004 | Kirakossian et al. |
| 2004/0166529 | A1 | 8/2004 | Singh et al. |
| 2004/0175765 | A1 | 9/2004 | Singh et al. |
| 2004/0197815 | A1 | 10/2004 | Singh et al. |
| 2004/0229293 | A1 | 11/2004 | Chan-Hui et al. |
| 2004/0229294 | A1 | 11/2004 | Chan-Hui et al. |
| 2004/0229299 | A1 | 11/2004 | Badal et al. |
| 2004/0229380 | A1 | 11/2004 | Chan-Hui et al. |
| 2004/0248150 | A1 | 12/2004 | Singh et al. |
| 2004/0265858 | A1 | 12/2004 | Singh et al. |
| 2005/0048553 | A1 | 3/2005 | Chenna et al. |
| 2005/0130238 | A1 | 6/2005 | Chan-Hui et al. |
| 2005/0130246 | A1 | 6/2005 | Salimi-Moosavi et al. |
| 2005/0170438 | A1 | 8/2005 | Chan-Hui et al. |
| 2006/0199231 | A1 | 9/2006 | Moore et al. |
| 2006/0223107 | A1 | 10/2006 | Chenna et al. |
| 2008/0187948 | A1 | 8/2008 | Chan-Hui et al. |
| 2008/0233602 | A1 | 9/2008 | Chan-Yui et al. |
| 2008/0254497 | A1 | 10/2008 | Singh |
| 2008/0311674 | A1 | 12/2008 | Singh et al. |
| 2009/0011432 | A1 | 1/2009 | Chan-Hui et al. |
| 2009/0011440 | A1 | 1/2009 | Mukherjee et al. |
| 2009/0111127 | A1 | 4/2009 | Chan-Hui et al. |
| 2009/0155818 | A1 | 6/2009 | Pidaparthi et al. |
| 2009/0173631 | A1 | 7/2009 | Boone et al. |
| 2009/0191559 | A1 | 7/2009 | Huang et al. |
| 2010/0143927 | A1 | 6/2010 | Sperinde et al. |
| 2010/0210034 | A1 | 8/2010 | Bates et al. |
| 2010/0233732 | A1 | 9/2010 | Bates et al. |
| 2010/0291594 | A1 | 11/2010 | Chan-Hui et al. |
| 2011/0180408 | A1 | 7/2011 | Badal et al. |

FOREIGN PATENT DOCUMENTS

| | | |
|---|---|---|
| WO | WO96/24061 | 8/1996 |
| WO | WO97/00446 | 1/1997 |
| WO | WO97/27325 | 7/1997 |
| WO | WO97/27327 | 7/1997 |
| WO | WO97/28275 | 8/1997 |
| WO | WO98/01533 | 1/1998 |
| WO | WO98/15830 | 4/1998 |
| WO | WO98/42736 | 10/1998 |
| WO | WO99/05319 | 2/1999 |
| WO | WO99/42838 | 8/1999 |
| WO | WO99/64519 | 12/1999 |
| WO | WO00/56925 | 9/2000 |
| WO | WO 00/66607 | 11/2000 |
| WO | WO01/57350 | 8/2001 |
| WO | WO 01/83502 | 11/2001 |
| WO | WO 02/12547 | 2/2002 |

| | | | |
|---|---|---|---|
| WO | WO 02/94998 | | 11/2002 |
| WO | WO 02/95356 | | 11/2002 |
| WO | WO 03/006947 | | 1/2003 |
| WO | WO 03/033741 | | 4/2003 |
| WO | WO 03/042398 | | 5/2003 |
| WO | WO 03/042657 | | 5/2003 |
| WO | WO 03/042658 | | 5/2003 |
| WO | WO 03/042699 | | 5/2003 |
| WO | WO03/045990 | | 6/2003 |
| WO | WO 03/076649 | | 9/2003 |
| WO | WO03/076649 | A1 | 9/2003 |
| WO | WO 03/085374 | | 10/2003 |
| WO | WO2004/000102 | | 12/2003 |
| WO | WO2004/008099 | | 1/2004 |
| WO | WO2004/009798 | | 1/2004 |
| WO | WO 2004/010842 | | 2/2004 |
| WO | WO 2004/011900 | | 2/2004 |
| WO | WO 2004/061131 | | 7/2004 |
| WO | WO 2004/061446 | | 7/2004 |
| WO | WO 2004/063700 | | 7/2004 |
| WO | WO 2004/068116 | | 8/2004 |
| WO | WO 2004/087887 | | 10/2004 |
| WO | WO 2004/091384 | | 10/2004 |
| WO | WO 2004/092353 | | 10/2004 |
| WO | WO 2005/019470 | | 3/2005 |
| WO | WO 2005/037071 | | 4/2005 |
| WO | WO 2005/045058 | | 5/2005 |
| WO | WO 2005/072507 | | 8/2005 |
| WO | WO 2006/044748 | | 4/2006 |
| WO | WO 2006/052788 | | 5/2006 |
| WO | WO 2006/084018 | | 8/2006 |
| WO | WO 2009/070772 | | 6/2009 |
| WO | WO 2009/086197 | | 7/2009 |
| WO | WO 2010/065568 | | 6/2010 |
| WO | WO 2010/083463 | | 7/2010 |
| WO | WO 2010/083470 | | 7/2010 |

OTHER PUBLICATIONS

Sperinde, J. et al., "A comparative study of p95-HER2 carboxy terminal fragment (CTF) detected by immunohistochemistry and VeraTag immunoassays in human breast tumors," In: Proc. Am. Assoc. Cancer Res., Mar. 31, 2012-Apr. 4, 2012, Chicago, IL. Philadelphia (PA): AACR; Cancer Res. 2012, 72(8 Suppl): Abstract 687.

Sperinde, J. et al., "A comparative study of p95-HER2 carboxy terminal fragment (CTF) detected by immunohistochemistry and VeraTag immunoassays in human breast tumors," American Association for Cancer Research (AACR) Annual Meeting, Mar. 31-Apr. 4, 2012, Chicago, IL (Poster 687).

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 2012 J. Clin. Oncol. 30 (Jun. 20 Suppl.): Abstract 608.

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," American Society of Clinical Oncology (ASCO) Annual Meeting, May 31-Jun. 4, 2012, Chicago, IL (Poster 608).

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," 2011 J. Clin. Oncol. 29(15)(May 20 Suppl.): Abstract 586.

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," American Society of Clinical Oncology (ASCO) Annual Meeting, Jun. 3-7, 2011, Chicago, IL (Poster 586).

Cook, J.W. et al., "Mutations in the catalytic domain of PI3 kinase and correlation with clinical outcome in trastuzumab-treated metastatic breast cancer (MBC)," 2011 J. Clin. Oncol. 29(15)(May 20 Suppl.): Abstract 582.

Cook, J.W. et al., "Mutations in the catalytic domain of PI3 kinase and correlation with clinical outcome in trastuzumab-treated metastatic breast cancer (MBC)," American Society of Clinical Oncology (ASCO) Annual Meeting, Jun. 3-7, 2011, Chicago, IL (Poster 582).

Duchnowska, R. et al., "Correlation between Quantitative HER2 Protein Expression and Risk of Brain Metastases in HER2-Positive Advanced Breast Cancer Patients Receiving Trastuzumab-Containing Therapy," Cancer Research, Dec. 15, 2011, 71(24 Suppl. 3):291s (Abstract P2-12-05).

Duchnowska, R. et al., "Correlation between Quantitative HER2 Protein Expression and Risk of Brain Metastases in HER2-Positive Advanced Breast Cancer Patients Receiving Trastuzumab-Containing Therapy," Annual San Antonio Breast Cancer Symposium, Dec. 6-10, 2011, San Antonio, TX, USA (Poster P2-12-05).

Huang, W. et al., "Comparison of four HER2 testing methods in detection of HER2-positive breast cancer: results in the FinHer study cohort," Cancer Research, Dec. 15, 2011, 71(24)(Suppl. 3):187s-188s (Abstract P1-07-01).

Huang, W. et al., "Comparison of four HER2 testing methods in detection of HER2-positive breast cancer: results in the FinHer study cohort," Annual San Antonio Breast Cancer Symposium, Dec. 6-10, 2011, San Antonio, TX, USA (Poster P1-07-01).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Cancer Research, Dec. 15, 2011, 71(24)(Suppl. 3):192s-193s (Abstract P1-07-12).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Annual San Antonio Breast Cancer Symposium, Dec. 6-10, 2011, San Antonio, TX, USA (Poster P1-07-12).

Shi, Y. et al., "Quantitative measurement of HER3-PI3K complex and total p85a subunit in formalin-fixed, paraffin-embedded (FFPE) tissues using VeraTag™ immunoassays," American Association for Cancer Research Special Conference: Targeting PI3K/mTOR Signaling in Cancer, Feb. 24-27, 2011, San Francisco, CA: Poster.

Wallweber, J. et al., "Subclassification of squamous cell carcinomas of the head and neck based on HER/ErbB and c-MET receptor protein expression and activation profiles," In: Proc. Am. Assoc. Cancer Res. AACR, Apr. 2-6, 2011, Orlando, FL: Abstract LB-323.

Wallweber, J. et al., "Subclassification of squamous cell carcinomas of the head and neck based on HER/ErbB and c-MET receptor protein expression and activation profiles," American Association for Cancer Research (AACR) Annual Meeting, Apr. 2-6, 2011, Orlando, FL (Poster LB-323).

Duchnowska, R. et al., "Correlation between quantitative HER2 Protein level and the risk of brain metastases (BM) in patients (ots) with metastatic breast cancer (MBC) treated with trastuzumab-containing therapy," 2010 J. Clin. Oncol. 28(15s) (Jun. 20 Suppl.): Abstract 1030.

Duchnowska, R. et al., "Correlation between quantitative HER2 Protein level and the risk of brain metastases (BM) in patients (ots) with metastatic breast cancer (MBC) treated with trastuzumab-containing therapy," American Society of Clinical Oncology (ASCO) Annual Meeting, Jun. 4-8, 2010, Chicago, IL (Poster 1030).

Wallweber, J., "Quantitative assessment of HER/erbB receptor protein expression and activation status in FFPE tumor samples identifies an activated HER1 signature in squamous cell carcinomas of the head and neck," In: Proc. Am. Assoc. Cancer Res. AACR, Apr. 17-21, 2010, Washington, D.C.: Abstract LB-66.

Wallweber, J., "Quantitative assessment of HER/erbB receptor protein expression and activation status in FFPE tumor samples identifies an activated HER1 signature in squamous cell carcinomas of the head and neck," American Association for Cancer Research (AACR) Annual Meeting, Apr. 17-21, 2010, Washington, D.C. (Poster LB-66).

Bates, M. et al., "Relationship between Quantitative HER2 Protein Expression and Clinical Outcomes in ER-Positive and ER-Negative Sub-Groups of Patients with Trastuzumab," Dec. 15, 2009, Cancer Research 69(24)(Suppl. 1): Abstract 5136.

Bates, M. et al., "Relationship between Quantitative HER2 Protein Expression and Clinical Outcomes in ER-Positive and ER-Negative Sub-Groups of Patients with Trastuzumab," 32nd Annual San Antonio Breast Cancer Symposium, Dec. 9-13, 2009, San Antonio, TX, USA (Poster 5136).
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," In: Proc. Am. Assoc. Cancer Res. AACR, Apr. 18-22, 2009, Denver, CO: Abstract 5427.
Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," American Association of Cancer Research (AACR) Annual Meeting, Apr. 18-22, 2009, Denver, CO (Poster 5427).
Joensuu, H. et al. "Breast cancer patients with very high tumor HER2 expression levels might not benefit from treatment with trastuzumab plus chemotherapy: A retrospective exploratory analysis of the FinHer trial," Dec. 15, 2009, Cancer Research 69(24)(Suppl. 1): Abstract 5083.
Joensuu, H. et al. "Breast cancer patients with very high tumor HER2 expression levels might not benefit from treatment with trastuzumab plus chemotherapy: A retrospective exploratory analysis of the FinHer trial," 32nd Annual San Antonio Breast Cancer Symposium, Dec. 10-13, 2009, San Antonio, TX, USA.
Williams, S. et al., "Profiling PI3K-Akt pathway activation in formalin fixed, paraffin-embedded cell line models and breast and ovarian tumors using a novel proximity assay," In: Proc. Am. Assoc. Cancer Res. AACR, Apr. 18-22, 2009, Denver, CO: Abstract 5251.
Williams, S. et al., "Profiling PI3K-Akt pathway activation in formalin fixed, paraffin-embedded cell line models and breast and ovarian tumors using a novel proximity assay," American Association of Cancer Research (AACR) Annual Meeting, Apr. 18-22, 2009, Denver, CO (Poster 5251).
Lipton, A. et al., "Multiple Subtypes of HER-2/Neu-Positive Metastatic Breast Cancer," Cancer Research, Dec. 15, 2009, 69(24 Suppl. 1): Abstract 2030.
Lipton, A. et al., "Multiple Subtypes of HER-2/Neu-Positive Metastatic Breast Cancer," 32nd Annual San Antonio Breast Cancer Symposium, Dec. 9-13, 2009, San Antonio, TX, USA (Poster 2030).
Shi, Y. et al., "Quantitative, sensitive, and reproducible measurement of epidermal growth factor receptor/HER1 homodimerization and total expression in formalin-fixed, paraffin-embedded tumors using a novel proximity-based assay," In: Proc. Am. Assoc. Cancer Res. AACR, Apr. 18-22, 2009, Denver, CO: Abstract 5244.
Shi, Y. et al., "Quantitative, sensitive, and reproducible measurement of epidermal growth factor receptor/HER1 homodimerization and total expression in formalin-fixed, paraffin-embedded tumors using a novel proximity-based assay," American Association of Cancer Research (AACR) Annual Meeting, Apr. 18-22, 2009 Denver, CO (Poster 5244).
Leitzel, A. et al., "Discordant HER2 Total and HER2 Homodimer Levels by HERmark Analysis in Matched Primary and Metastatic Breast Cancer FFPE Specimens," Cancer Research, Dec. 15, 2009, 69(24 Suppl. 1): Abstract 2132.
Leitzel, A. et al., "Discordant HER2 Total and HER2 Homodimer Levels by HERmark Analysis in Matched Primary and Metastatic Breast Cancer FFPE Specimens," 32nd Annual San Antonio Breast Cancer Symposium, Dec. 9-13, 2009, San Antonio, TX, USA (Poster 2132).
Badal, M.Y. et al., "Measurement of the HER3-PI3K complex as a marker of PI3K-Akt pathway activation in formalin fixed, paraffin-embedded cell line models and breast and ovarian tumors using a novel proximity assay," American Association for Cancer Research (AACR) Special Conference on Targeting the PI3K-Kinase Pathway in Cancer, Nov. 11-14, 2008, Cambridge, MA, USA (Poster).
Bates, M., et al., "Quantitative HER2 homodimer levels correlate with time to first recurrence in HER2-positive breast cancer patients who did not receive trastuzumab in the adjuvant setting," Cancer Res. Jan. 15, 2009, 69(2 Suppl. 1): Abstract 1074.
Bates, M. et al., "Quantitative HER2 homodimer levels correlate with time to first recurrence in HER2-positive breast cancer patients who did not receive trastuzumab in the adjuvant setting," 31st Annual San Antonio Breast Cancer Symposium, Dec. 10-14, 2008, San Antonio, TX, USA (Poster 1074).
Eli, L. et al., "Development of novel-proximity-based immunoassays for activated HER1, HER2, HER1-HER2 heterodimers in formalin-fixed, paraffin-embedded (FFPE) cells," 2008 Eur. J. Cancer 6(Oct. 12):30 (Abstract 88).
Eli, L. et al., "Development of novel-proximity-based immunoassays for activated HER1, HER2, HER1-HER2 heterodimers in formalin-fixed, paraffin-embedded (FFPE) cells," International Conference on Molecular Targets and Cancer Therapeutics, AACR-NCI-EORTC, Oct. 21-24, 2008, Geneva, Switzerland (Poster 88).
Huang, W. et al., "Comparison of Central HER-2 Tests With Quantitative HER-2 Expression and HER-2 Homodimer Measurements Using A Novel Proximity Based Assay," 2008 Arch. Pathol. Lab. Med. 132 (Sept.):1476 (CAP Abstract 40).
Huang, W. et al., "Comparison of Central HER-2 Tests With Quantitative HER-2 Expression and HER-2 Homodimer Measurements Using A Novel Proximity Based Assay," American College of Pathologist (CAP) Annual Meeting, Sep. 25-28, 2008 (Poster 40).
Joensuu, H. et al., "Quantitative measurement of HER2 expression and HER2 homodimer using a novel proximity based assay: comparison with HER2 status by immunohistochemistry and chromogenic in situ hybridization in the FinHer study," Cancer Research, Jan. 15, 2009, 69(2 Suppl. 1): Abstract 2071.
Joensuu, H. et al., "Quantitative measurement of HER2 expression and HER2 homodimer using a novel proximity based assay: comparison with HER2 status by immunohistochemistry and chromogenic in situ hybridization in the FinHer study," 31st Annual San Antonio Breast Cancer Symposium, Dec. 10-14, 2008, San Antonio, TX, USA (Poster 2071).
Lipton, A. et al., "HER2 protein expression predicts response to trastuzumab in FISH-positive patients," Cancer Research, Jan. 15, 2009, 69(2 Suppl. 1): Abstract 32.
Lipton, A. et al., "HER2 protein expression predicts response to trastuzumab in FISH-positive patients," 31st Annual San Antonio Breast Cancer Symposium, Dec. 10-14, 2008, San Antonio, TX, USA (Oral Presentation 32).
Leitzel K., et al., "Use of total HER2 and HER2 homodimer levels to predict response to trastuzumab," J. Clin. Oncol. 2008 (May 20 Suppl.): Abstract 1002.
Leitzel, K. et al., "Total HER2 and HER2 homodimer levels predict response to trastuzumab," American Society of Clinical Oncology (ASCO) Annual Meeting, May 30-Jun. 3, 2008, Chicago, IL (Oral Presentation 1002).
Mukherjee, A. et al., "Proximity-based assays for the detection of activated HER3, HER2/3 heterodimers and HER3/PI3K complexes in FFPE cell line controls and tumors," Cancer Research, Jan. 15, 2009, 69(Suppl. 1): Abstract 4040.
Mukherjee, A. et al., "Proximity-based assays for the detection of activated HER3, HER2/3 heterodimers and HER3/PI3K complexes in FFPE cell line controls and tumors," 31st Annual San Antonio Breast Cancer Symposium, Dec. 10-14, 2008, San Antonio, TX, USA (Poster 4040).
Shi, Y. et al., "Development of highly quantitative, sensitive, and reproducible assays for the detection of EGFR/HER1 and ErbB3/HER3 in in formalin-fixed, paraffin-embedded cells," 2008 Eur. J. Cancer 6(Oct. 12):34-35 (Abstract 103).
Shi, Y. et al., "Development of highly quantitative, sensitive, and reproducible assays for the detection of EGFR/HER1 and ErbB3/HER3 in in formalin-fixed, paraffin-embedded cells," International Conference on Molecular Targets and Cancer Therapeutics, AACR-NCI-EORTC, Oct. 21-24, 2008, Geneva, Switzerland, Poster 103.
Bates, M.P. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements For Concomitant Chemotherapy," 2007 J. Clin. Oncol. 25(18S) (Jun. 20 Suppl.): Abstract 10557.
Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," American Society of Clinical Oncology (ASCO) Annual Meeting, Jun. 2-5, 2007, Chicago, IL (Poster 10557).
Dua, R. et al., "Profiling HER-Family Receptor Dimerization in HER2 Overexpressing Cells that Coexpress Mutated EGFR Receptors," Breast Cancer Research and Treatment, Dec. 13, 2007, 106(1 Suppl.):5203 (Abstract 4108).
Dua, R. et al., "Profiling HER-Family Receptor Dimerization in HER2 Overexpressing Cells that Coexpress Mutated EGFR Receptors," 30th Annual San Antonio Breast Cancer Symposium, Dec. 13-16, 2007, San Antonio, TX, USA (Poster 4108).
Dua, R. et al., "Patterns of HER-Family Receptor Dimerization Intrastuzumab Susceptible and Trastuzumab Resistant Cell Lines," 2007 J. Clin. Oncol. 25(18S) (Jun. 20 Suppl.): Abstract 2533.
Dua, R. et al., "Patterns of HER-Family Receptor Dimerization Intrastuzumab Susceptible and Trastuzumab Resistant Cell Lines," American Society of Clinical Oncology (ASCO) Annual Meeting, Jun. 2-5, 2007, Chicago, IL, USA (Poster 2533).
Eli, L. et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Dec. 13, 2007, 106(1 Suppl.):S87-S88 (Abstract 2011).
Eli, L. et al., "Development of Novel Proximity-Based Immunoassays for the Detection of HER Heterodimerization in Breast Cancer Cell Line Lysates and Formalin-Fixed, Paraffin-Embedded Tissue," 30th Annual San Antonio Breast Cancer Symposium, Dec. 13-16, 2007, San Antonio, TX, USA (Poster 2011).
Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, Dec. 13, 2007, 106(1 Suppl.):S86 (Abstract 2007).
Huang, W. et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," 30th Annual San Antonio Breast Cancer Symposium, Dec. 13-16, 2007, San Antonio, TX, USA (Poster 2007).
Toi, M. et al., "Differential Survival Following Trastuzumab Treatment Based on Quantitative HER2 Expression and HER2 Dimerization in a Clinic-Based Cohort of Patients With Metastatic Breast Cancer," 2007 J. Clin. Oncol. 25(18S) (Jun. 20 Suppl.): Abstract 1025.
Toi, M. et al., "Differential Survival following Trastuzumab Treatment based on Quantitative HER2 Expression and HER2:HER2 Dimerization in a Clinic-Based Cohort of Patients with Metastatic Breast Cancer," American Society of Clinical Oncology (ASCO) Annual Meeting, Jun. 2-5, 2007, Chicago, IL (Poster 1025).
Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, Dec. 13, 2007, 106(1 Suppl.):S207 (Abstract 5002).
Wallweber, J. et al., "Increased Detection of Breast Cancer Markers Human Epidermal Growth Factor Receptor Dimer and Downstream Signaling Proteins Utilizing the VeraTag Technology with Dextran Modified Antibodies," 30th Annual San Antonio Breast Cancer Symposium, Dec. 13-16, 2007, San Antonio, TX, USA (Poster 5002).
Winslow, J. et al., "Characterization of a Novel Proximity Immunoassay for the Quantitative Determination of HER2 Protein Expression and HER2 Homodimerization in Formalin-Fixed, Paraffin-Embedded Breast Cancer Tissue," Breast Cancer Research and Treatment, Dec. 13, 2007, 106(1 Suppl.):S88 (Abstract 2012).
Winslow, J. et al., "Characterization of a Novel Proximity Immunoassay for the Quantitative Determination of HER2 Protein Expression and HER2 Homodimerization in Formalin-Fixed, Paraffin-Embedded Breast Cancer Tissue," 30th Annual San Antonio Breast Cancer Symposium, Dec. 13-16, 2007, San Antonio, TX, USA (Poster 2012).
Hameed, M.R. et al., "The ERB family receptor dimerization in glioblastoma—An eTag assay analysis of 23 cases," 2006 J. Clin. Oncol. 24(18S) (Jun. 20 Suppl.): Abstract 1582.
Hameed, M.R. et al., "The ERB family receptor dimerization in glioblastoma—An eTag assay analysis of 23 cases," American Society of Cancer Oncology (ASCO) Annual Meeting, Jun. 2-6, 2006, Atlanta, GA (Poster 1582).
Jimeno, A. et al., "Combined targeted therapy shows increased efficacy in a novel in vivo pancreas cancer model," American Association for Cancer Research (AACR) Annual Meeting, Apr. 1-6, 2006, Washington, D.C. (Abstract 2181).
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA: Abstract A121.
Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA (Poster A121).
Shi, Y., "Analysis of ErbB/HER receptor pathways in formalin-fixed and paraffin-embedded cancer cell lines using multiplexed eTag™ assays," 2005 J. Clin. Oncol. 23(16S) (Jun. 1 Suppl.): Abstract 9565.
Shi, Y. et al., "Analysis of ErbB/HER receptor pathways in formalin-fixed and paraffin-embedded cancer cell lines using multiplexed eTag™ assays," American Society of Clinical Oncology (ASCO) Annual Meeting, May 13-17, 2005, Orlando, FL (Poster 9565).
Mukherjee, A. et al., "Correlation of ErbB activation status and clinical response in Herceptin treated breast cancer patients," 2005, Proc. Amer. Canc. Res., 46 (Apr. 16): Abstract 3688.
Mukherjee, A. et al., "Correlation of ErbB activation status and clinical response in Herceptin treated breast cancer patients," American Association for Cancer Research (AACR) Annual Meeting, Apr. 16-20, 2005, Anaheim/Orange County, CA, USA (Poster 3688).
Mukherjee, A., "The Use of ErbB/HER Activation Status as Prognostic Markers in Breast Cancer Patients Treated with Trastuzumab," 2005 J. Clin. Oncol. 23(16S) (Jun. 1 Suppl.): Abstract 553.
Mukherjee, A. et al., "The use of ErbB activation Status as Prognostic Markers in Breast Cancer Patients Treated with Trastuzumab," American Society of Clinical Oncology (ASCO) Annual Meeting, May 13-17, 2005, Orlando, FL (Poster 553).
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA: Abstract A127.
Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA (Poster A127).
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA: Abstract A124.
Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA (Poster A124).
Salimi-Moosavi, H. et al., "IC50 determination for receptor-targeted compounds and downstream signaling," In: Proc. Am. Assoc. Cancer Res. AACR, Apr. 16-20, 2005, Anaheim, CA: Abstract 4567.
Shi, Y. et al., "Multiplexed assay for assessing ErbB/HER receptor pathways in formalin-fixed and paraffin-embedded cancer cell lines," In: Proc. Am. Assoc. Cancer Res. AACR Apr. 16-20, 2005 Anaheim, CA: Abstract 5762.
Shi, Y. et al., "Multiplexed assay for assessing ErbB/HER receptor pathways in formalin-fixed and paraffin-embedded cancer cell lines," American Association for Cancer Research (AACR) Annual Meeting, Apr. 16-20, 2005, Anaheim, CA (Poster 5762).
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA: Abstract B17.
Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA (Poster B17).
Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK (Poster 1025).
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA: Abstract A123.
Yatabe, Y et al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA (Poster A123).
Duchnowska, R. et al., "Correlation between quantitative HER2 protein expression and risk of brain metastasis in HER2-positive advanced breast cancer patients receiving trastuzumab-containing therapy," Oncologist 17(1):26-35 (2012) (pub. online Jan. 10, 2012).
Han, S-W, "Correlation of HER2, p95HER2 and HER3 expression and treatment outcome of lapatinib plus capecitabine in HER2-positive metastatic breast cancer," PLoS ONE 7(7):e39943 (2012) (pub. online Jul. 27, 2012).
Bates, M. et al., "Identification of a Subpopulation of Metastatic Breast Cancer Patients with Very High HER2 Expression Levels and Possible resistance to Trastuzumab," Ann. Oncol., 22(9):2014-2020 (2011) (pub. online Feb. 11, 2011).
Defazio-Eli, L. et al., "Quantitative assays for the measurement of HER1-HER2 heterodimerization and phosphorylation in cell lines and breast tumors: applications for diagnostics and targeted drug mechanism of action," Breast Canc. Res. 13:R44 (2011) (pub. Apr. 15, 2011).
Dua, R. et al., "Detetion of hepatocyte growth factor (HGF) ligand-C-met receptor activation in formalin-fixed, paraffin-embedded specimens by a novel proximity assay," PLOS One 6(1): e15932 (2011) (pub. online Jan. 21, 2011).
Joensuu, H. et al., "Very high quantitative tumor HER2 content and outcome in early breast cancer," Ann. Oncol. 22(9): 2007-2013 (2011) (pub. online Feb. 1, 2011).
Ghosh, M. et al., "Trastuzumab has preferential activity against breast cancers driven by HER2 homodimers," Cancer Res. 71(5):1871 (2011) (pub. online Feb. 15, 2011).
Dua, R. et al., "EGFR over-expression and activation in high HER2, ER negative breast cancer cell lines induces trastuzumab resistance," Breast Cancer Res. Treat. 122(3):6850697 (2010) (pub. online Oct. 27, 2009).
Jain, A. et al., "HER kinase axis receptor dimer partner switching occurs in response to EGFR tyrosine kinase inhibition despite failure to block cellular proliferation," Cancer Res. 70(5):1989-1999 (2010) (pub. online Feb. 16, 2010).
Huang, Q. et al., "Comparison of central HER2 testing with quantitative total HER2 expression and HER2 homodimer measurement using a novel proximity based assay," Am. J. Clin. Pathol. 134:303-311 (2010) (pub. Aug. 2010).
Larson, J.S. et al., "Analystical validation of a highly senstivie, accurate, and reproducible assay (HERmark®) for the measurement of HER2 total protein and HER2 homodimers in FFPE breast cancer tumor specimens," Pathol. Res. Intl, 2010: Article ID 814176 (2010) (pub. online Jun. 28, 2010).
Lipton, A. et al., "Quantitative HER2 protein levels predict outcome in fluorescence in situ hybridization-positive patients with metastatic breast cancer treated with trastuzumab," Cancer 116:5168-5178 (2010) (pub. online Nov. 3, 2010).
Mamluk, R. et al., "Anti-tumor effect of CT-322 as an adnectin inhibitor of vascular endothelial growth factor receptor-2," MAbs 2(2):199-208 (2010) (pub. online Mar. 1, 2010).
Toi, M. et al., "Differential survival following trastuzumab treatment based on quantitative HER2 expression and HER2 homodimers in a clinic-based cohort of patients with metastatic breast cancer," BMC Cancer 10:56 (2010) (pub. Feb. 23, 2010) (10 pages).
Desmedt, C. et al., "Quantitation of HER2 expression or HER2:HER2 dimers and differential survival in a cohort of metastatic breast cancer patients carefully selected for trastuzumab treatment primarily by FISH," Diagn. Mol. Pathol. 18(1):22-29 (2009) (pub. Mar. 2009).
Chan-Hui, P-Y et al., "Applications of eTag™ assay platform to systems biology approaches in molecular oncology and toxicology studies," Clin. Immun. 111:162-174 (2004) (pub. online Mar. 11, 2004).
Tian, H. et al., "Multiplex mRNA assay using electrophoretic tags for high-throughput gene expression analysis," Nucl. Acid Res. 32(16):e126 (pub. online Sep. 8, 2004).
Mukherjee, A. et al., "Profiling the HER3/PI3K Pathway in Breast Tumors Using Proximity-Directed Assays Identifies Correlations between Protein Complexes and Phosphoproteins," PLoS One 6(1): e16443 (2011) (pub. online Jan. 28, 2011).
Sperinde, J. et al., "Quantitation of p95HER2 in paraffin sections by using a p95-specific antibody and correlation with outcome in a cohort of trastuzumab-treated breast cancer patients," Clin. Canc. Res. 16(16):4226-4235 (2010) (pub. online Jul. 27, 2010).
Shi, Y. et al., "A novel proximity assay for the detection of proteins and protein complexes: quantitation of HER1 and HER2 total protein expression and homodimerization in formalin-fixed, paraffin-embedded cell lines and breast cancer tissue," Diagn. Mol. Pathol. 18(1):11-21 (2009) (pub. Mar. 2009).
Cho, S. and Pak, J., "Fabrication of a Multi-Electrode Array DNA Sensor for Electrochemical Genotyping," 2002, J. Korean Phys. Soc., 41(6):1054-1057.
Dankort, D. et al., "Grb2 and Shc Adapter Proteins Play Distinct Roles in Neu (ErbB-2)-Induced Mammary Tumorigenesis: Implications for Human Breast Cancer," 2001, Mol. Cell. Biol., 21(5):1540-1551.
Devi, L., "Heterodimerization of G-protein-coupled receptors:pharmacology, signaling and trafficking," 2001, Trends Pharma. Sci., 22(10):532-537.
De-Los-Santosalvarez, P. et al., "New scheme for electrochemical detection of DNA based on electrocatalytic oxidation of NADH," 2003, Electrochem. Commun., 5:267-271.
International Search Report and Written Opinion mailed Apr. 19, 2007 corresponding to Application No. PCT/US04/33815.
International Search Report and Written Opinion mailed Apr. 25, 2005 corresponding to Application No. PCT/US04/25945.
International Search Report and Written Opinion mailed Mar. 27, 2006 corresponding to Application No. PCT/US04/09805.
International Search Report and Written Opinion mailed Nov. 2, 2005 corresponding to Application No. PCT/US04/09715.
International Search Report and Written Opinion mailed Dec. 10, 2004 corresponding to Application No. PCT/US04/11900.
Yakes et al, Cancer Res, 2002, 62:4132-4141.*
Ady, et al., "Detection of HER-2/neu-positive circulating epithelial cells in prostate cancer patients," British Journal of Cancer, 2004, 90:443-448.
Agus, et al., "A Potential Role for Activated HER-2 in Prostate Cancer," Seminars in Oncology, 2000, 27:76-100.
Agus, et al., "Targeting ligand-activated ErbB2 signaling inhibits breast and prostate tumor growth," Cancer Cell, 2002, 2:127-137.
Ahram, et al., "Proteomic Analysis of Human Prostate Cancer," Molecular Carcinogenesis, 2002, 33:9-15.
Albanell, et al., "Mechanism of Action of Anti-HER2 Monoclonal Antibodies: Scientific Update on Trastuzumab and 2C4," New Trends in Cancer for the 21st Century, 2003, 253-268.
Alimandi, et al., "Cooperative signaling of ErbB3 and ErbB2 in neoplastic transformation and human mammary carcinomas," Oncogene, 1995, 10:1813-1821.
Andersen, "Determination of Estrogen Receptors in Paraffin-Embedded Tissue," Acta Oncologica, 1992, 31:611-627.

Angers, et al., "Dimerization: An Emerging Concept for G Protein-Coupled Receptor Ontogeny and Function," Annu. Rev. Pharmacol. Toxicol., 2002, 42:409-435.
Antonsson, et al., "An in Vitro 96-Well Plate Assay of the Mitogen-Activated Protein Kinase Cascade," Analytical Biochemistry, 1999, 267:294-299.
Arteaga, "Epidermal Growth Factor Receptor Dependence in Human Tumors: More Than Just Expression?," The Oncologist. 2002, 7:31-39.
Auerbach, et al., "Proteomic approaches for generating comprehensive protein interaction maps," Targets, 2003, 2:85-92.
Baselga, "Anti-EGFR therapy: A new targeted approach to cancer treatment," Oncology Biotherapeutics, 2002, 2:2-36.
Baselga, "A new anti-ErbB2 strategy in the treatment of cancer: Prevention of ligand-dependent ErbB2 receptor heterodimerization," Cancer Cell, 2002, 2:93-95.
Baselga, et al., "Mechanism of action of anti-HER2 monoclonal antibodies," Annals of Oncology, 2001, 12:S35-S41.
Bast, et al., "Coexpression of the HER-2 Gene Product, $p185^{HER-2}$, and Epidermal Growth Factor Receptor, $p170^{EGF-R}$, on Epithelial Ovarian and Normal Tissues," Hybridoma, 1998, 17:313-321.
Beaudet, et al., "Homogenous Assays for Single-Nucleotide Polymorphism Typing Using AlphaScreen," Genome Research, 2001, 11:600-608.
Becker, "Signal transduction inhibitors—a work in progress," Nature Biotechnology, 2004, 22:15-18.
Bei, et al., "Co-localization of multiple ErbB receptors in stratified epithelium of oral squamous cell carcinoma," Journal of Pathology, 2001, 195:343-348.
Bichsel, et al., "Cancer Proteomics: From Biomarker Discovery to Signal Pathway Profiling," The Cancer Journal, 2001, 7:69-78.
Blagoev, et al., "A proteomics strategy to elucidate functional protein-protein interactions applied to EGF signaling," Nature Biotechnology, 2003, 21:315-318.
Blakely, et al., "Epidermal growth factor receptor dimerization monitored in live cells," Nature Biotechnology, 2000, 18:218-222.
Blume-Jensen, et al., "Oncogenic kinase signalling," Nature, 2001, 411:355-365.
Bodey, et al., "Clinical and Prognostic Significance of the Expression of the c-erbB-2 and c-erB-3 Oncoproteins in Primary and Metastatic Malignant Melanomas and Breast Carcinomas," Anticancer Research, 1997 17:1319-1330.
Bohula, et al., "Targeting the type 1 insulin-like growth factor receptor as anti-cancer treatment," Anti-Cancer Drugs, 2003, 14:669-682.
Brandt, et al., "c-erB-2/EGFR as dominant heterodimerization partners determine a motogenic phenotype in human breast cancer cells," The FASEB Journal, 1999, 13:1939-1949.
Brockhoff, et al., "Epidermal Growth Factor Receptor, c-erbB2 and c-erbB3 Receptor Interaction, and Related Cell Cycle Kinetics of SK-BR-3 and BT474 Breast Carcinoma Cells," Cytometry, 2001, 44:338-348.
Chow, et al., "Expression profiles of ErbB Family Receptors and Prognosis in Primary Transitional Cell Carcinoma of the Uminary Bladder," Clinical Cancer Research, 2001, 7:1957-1962.
Clot, et al., "HLA-DR53 molecules are associated with susceptibility to celiac disease and selectively bind gliadin-derived peptides," Immunogenetics, 1999, 49:800-807.
Dahan, et al., "Diffusion Dynamics of Glycine Receptors Revealed by Single-Quantum Dot Tracking," Science, 2003, 302:442-446.
Dean, et al., "Cell Surface Density of $p185^{c-erB-2}$ Determines Susceptibility to Anti-$P185^{c-erB-2}$ Ricin A Chain (RTA) Immunotoxin Therapy Alone and in Combination with Anti-P 170EGFR-RTA in Ovarian Cancer Cells," Clinical Cancer Research, 1998, 4:2545-2550.
DePrimo, et al., "Expression profiling of blood samples from an SU5416 Phase III metastatic colorectal cancer clinical trial: a novel strategy for bionrarker identification," BMC Cancer, 2003, 3:1-12.
Dikic, "CIN85/CMS family of adaptor molecules," FEBS Letters, 2002, 529:110-115.
Fredriksson, et al., "Protein detection using proximity-dependent DNA ligation assays," Nature Biotechnology, 2002, 20:473-477.
Galameau, et al., "∃-Lactamase protein fragment complementation assays as in vivo and in vitro sensors of protein-protein interactions," Nature Biotechnology, 2002, 20:619-622.
Garnett, et al., "Secondary Dimerization between Members of the Epidermal Growth Factor Receptor Family," The Journal of Biological Chemistry, 1997, 272:12051-12056.
Gilbertson, et al., "ERBB Receptor Signaling Promotes Ependymoma Cell Proliferation and Represents a Potential Novel Therapeutic Target for This Disease," Clinical Cancer Research, 2002, 8:3054-3064.
Gilbertson, et al., "Expression of the ErbB-Neuregulin Signaling Network during Human Cerebellar Development: Implications for the Biology of Medulloblastoma," Cancer Research, 1998, 58:3932-3941.
Gilbertson, et al., "Prognostic Significance of HER2 and HER4 Coexpression in Childhood Medullobalstoma," Cancer Research, 1997, 57:3272-3280.
Graham, et al., "Application of p-Galactosidase Enzyme Complementation Technology as a High Throughput Screening format for Antagonists of the Epidermal Growth Factor Receptor," Journal of Biomolecular Screening, 2001, 6:401-411.
Graus-Porta, et al., "ErbB-2, the preferred heterodimerization partner of all ErbB receptors, is a mediator of lateral signaling," The EMBO Journal, 1997, 16:1647-1655.
Gur, et al., "Enlightened receptor dymanics," Nature Biotechnology, 2004, 22:169-170.
Hanash, "Disease Proteomics," Nature, 2003, 422:226-232.
Hanna, et al., "Evaluation of HER-2/neu (erbB-2) Status in Breast Cancer: From Bench to Bedside," Mod. Pathol., 1999, 12:827-834.
Hayes, et al., "Monitoring expression of HER-2 on circulating epithelial cells in patients with advanced breast cancer," International Journal of Oncology, 2002, 21:1111-1117.
Herbst, et al., "Monoclonal Antibodies to Target Epidermal Growth Factor Receptor-Positive Tumors," Cancer, 2002, 94:1593-1611.
Holbro, et al., "Me ErbB receptors and their role in cancer progression," Experimental Cell Research, 2003, 284:99-110.
Hondermarck, et al., "Proteomics of breast cancer for marker discovery and signal pathway profiling," Proteomics, 2001, 1:1216-1232.
Ibrahim, et al., "Expression of c-erbB Proto-Oncogene Family Members in Squamous Cell Carcinoma of the Head and Neck," Anticancer Research, 1997, 17:4539-4546.
Irvine, et al., "A colorimetric bead-binding assay for detection of intermolecular interactions," Experimental Dermatology, 2002, 11:462-467.
Jones, et al., "Proteomic analysis and identification of new biomarkers and therapeutic targets for invasive ovarian cancer," Proteomics, 2002, 2:76-84.
Kanematsu, et al., "Phosphorylation, But Not Overexpression, of Epidermal Growth Factor Receptor Is Associated With Poor Prognosis of Non-Small Cell Lung Cancer Patients," Oncology Research, 2003, 13:289-298.
Karin, et al., "The IKK NF-xB System: A Treasure Trove for Drug Development," Nature Reviews Drug Discovery, 2004, 3:17-26.
Karin, et al., "NF-xB in Cancer: From Innocent Bystander to Major Culprit," Nature Reviews Cancer, 2002, 2:301-310.
Kolch, "Meaningful relationships: the regulation of the Ras/Raf/MEK/ERK pathway by protein interaction," Biochem. J., 2000, 351:289-305.
Krahn, et al., "Coexpression patterns of EGF, HER2, HERS and HER4 in non-melanoma skin cancer," European Journal of Cancer, 2001, 37:251-259.
Lee, et al., "Investigation of the prognostic value of coexpressed erbB family members for the survival of colorectal cancer patients after curative surgery," European Journal of Cancer, 2002, 38: 1065-1071.
Li, et al., "NF-KB Regulation in the Immune System," Nature Reviews Immunology, 2002, 2:725-735.
Lidke, et al., "Quantum dot ligands provide new insights into erbB/HER receptor-mediated signal transduction," Nature Biotechnology, 2004, 22:198-203.
Liotta, et al., "Molecular Profiling of Human Cancer," Nature Reviews, 2000, 1:48-56.

Lund-Johansen, et al., "Flow Cytometric Analysis of Immunoprecipitates: High-Throughput Analysis of Protein Phosphorylation and Protein-Protein Interactions," Cytometry, 2000, 39:250-259.
McDonald, et al., "Expression profiling of medulloblastoma: PDGFRA and the RAS/MAPK pathway as therapeutic targets for metastatic disease," Nature Genetics, 2001, 29:143-152; Nature Genetics, 2003, 35:287.
McDonald, et al., "A Scintillation Proximity Assay for the Raf/MEK/ERK Kinase Cascade: High-Throughput Screening and Identification of Selective Enzyme Inhibitors," Analytical Biochemistry, 1999, 268:318-329.
Madoz-Gurpide, et al., "Molecular Analysis of Cancer Using DNA and Protein Microarrays," Advances in Experimental Medicine and Biology, 2003, 532:51-58.
Mallon, et al., "An Enzyme-Linked Immunosorbent Assay for the Raf/MEKI/MAPK Signaling Cascade," Analytical Biochemistry, 2001, 294:48-54.
Matko, et al., "Energy Transfer Methods for Detecting Molecular Clusters on Cell Surfaces," Methods in Enzymology, 1997, 278:444-462.
Miller, et al., "Antibody microarray profiling of human prostate cancer sera: Antibody screening and identification of potential biomarkers," Proteomics, 2003,3:56-63.
Muthuswamy, et al., "Controlled Dimerization of ErbB Receptors Provides Evidence for Differential Signaling by Homo- and Heterodimers," Molecular Cell Biology, 1999, 6845-6857.
Nagy, et al., "EGF-Induced Redistribution of erbB2 on Breast Tumor Cells: Flow and Image Cytometric Energy Transfer Measurements," Cytometry, 1998, 32:120-131.
Nahta, et al., "Growth Factor Receptors in Breast Cancer: Potential for Therapeutic Intervention," The Oncologist, 2003, 8:5-17.
Nam, et al., "Current Targets for Anticancer Drug Discovery," Current Drug Targets, 2003, 4:159-179.
Navolanic, et al., "EGFR family signaling and its association with breast cancer development and resistance to chemotherapy (Review)," International Journal of Oncology, 2003, 22:237-252.
Nicholson, et al., "The protein kinase B/ Akt signalling pathway in human malignancy," Cellular Signalling, 2002, 14:381-395.
Olayioye, et al., "ErbB-1 and ErbB-2 Acquire Distinct Signaling Properties Dependent upon Their Dimerization Partner," Molecular and Cellular Biology, 1998, 18:5042-5051.
Olayioye, et al., "The ErbB signaling network: receptor heterodimerization in development and cancer," The EMBO Journal, 2000, 19:3159-3167.
Orlowski, et al., "NF-KB as a therapeutic target in cancer," TRENDS in Molecular Medicine, 2002, 8:385-389.
Packard BioScience, "Principles of AlphaScreen," Application Note ASC-001, 2001.
Pawson, et al., "Assembly of Cell Regulatory Systems Through Protein Interaction Domains," Science, 2003, 300:445-452.
Pawson, et al., "Interaction domains: from simple binding events to complex cellular behavior," FEBS Letters, 2002, 513:2-10.
Pawson, "Specificity in Signal Transduction: From Phosphotyrosine-SH2 Domain Interactions to Complex Cellular Systems," Cell, 2004, 116:191-203.
Petricoin, et al., "Clinical Proteomics: Translating Benchside Promise Into Bedside Reality," Nature Reviews, 2002, 1:683-695.
Petricoin, et al., "Use of proteomic patterns in serum to identify ovarian cancer," The Lancet, 2002, 359:572-577.
Pinkas-Kramarski, et al., "Diversification of Neu differentiation factor and epidermal growth factor signaling by combinatorial receptor interactions," The EMBO Journal, 1996, 15:2452-2467.
Press, et al., "Evaluation fo HER-2/neu Gene Amplification and Overexpression: Comparison of Frequently Used Assay Methods in a Molecularly Characterized Cohort of Breast Cancer Specimens," Journal of Clinical Oncology, 2002, 20:3095-3105.
Price, et al., "Methods for the Study of Protein-Protein Interactions in Cancer Cell Biology," Methods in Molecular Biology, 2003, 218:255-267.
Rios, et al., "G-protein-coupled receptor dimerization: modulation of receptor function," Pharmacology & Therapeutics, 2001, 91:71-87.
Rolan, et al., "Use of biomarkers from drug discovery through clinical practice: Report of the Ninth European Federation of Pharmaceutical Sciences Conference on Optimizing Drug Development," Clinical Pharmacology & Theraputics, 2003, 73:284-291.
Ross, et al., "Me HER-2/neu Gene and Protein in Breast Cancer 2003: Biomarker and Target of Therapy," The Oncologist, 2003, 8:307-325.
Rowinsky, "Targeting Signal Transduction: The erbB Receptor Family as a Target for Therapeutic Development," Horizons in Cancer Therapeutics: From Bench to Bedside, 2:3-35 (2001).
Sako, et al., "Single-molecule imaging of EGFR signalling on the surface of living cells," Nature Cell Biology, 2000, 2:168-172.
Schlessinger, et al., "Cell Signaling by Receptor Tyrosine Kinases," Cell, 2000, 103:211-225.
Schlessinger, et al., "Ligand-Induced, Receptor-Mediated Dimerization and Activation of EGF Receptor," Cell, 2002, 110:669-672.
Schroeder, et al., "BrbB-R-Catenin Complexes Are Associated with Human Infiltrating Ductal Breast and Murine Mammary Tumor Virus (MMTV)-Wnt-1 and MMTV-c-Neu Transgenic Carcinomas," The Journal of Biological Chemistry, 2002, 277:22692-22698.
Schutz, et al., "Immunohistochemical Detection of Somatostatin Receptors in Human Ovarian Tumors," Gynecologic Oncology, 2002, 84:235-240.
Seymour, "Epidermal Growth Factor Receptor as a Target: Recent Developments in the Search for Effective New Anti-Cancer Agents," Current Drug Targets, 2001, 2:117-133.
Shackney, et al., "Intracellular Coexpression of Epidermal Growth Factor Receptor, Her-2/neu, and $p21^{ras}$ in Human Breast Cancers: Evidence for the Existence of Distinctive Patterns of Genetic Evolution That Are Common to Tumors from Different Patients," Clinical Cancer Research, 1998, 4:913-928.
Shi, et al., "Antigen Retrieval Immunohistochemistry: Past, Present, and Future," The Journal of Histochemistry & Cytochemis, 1997, 45:327-343.
Sidransky, "Emerging Molecular Markers of Cancer," Nature Reviews Cancer, 2002, 2:210-219.
Simon, "Receptor Tyrosine Kinases: Specific Outcomes from General Signals," Cell, 2000, 103:13-15.
Simpson, et al., "Cancer proteomics: from signaling networks to tumor markers," Trends in Biotechnology, 2001, 19:S40-S48.
Skirnisdottir, et al., "The growth factor receptors Her-2/neu and EGFR, their relationship, and their effects on the prognosis in early stage (FIGO I-II) epithelial ovarian carcinoma," Int J Gynecol Cancer, 2001, 11:119-129.
Sklar, et al., "Flow Cytometric Analysis of Ligand-Receptor Interactions and Molecular Assemblies," Anna Rev. Biomol. Struct., 2002, 31:97-119.
Stagljar, "Finding partners: Emerging Protein Interaction Technologies Applied to Signaling Networks," Sci. STKE, 2003, pe56:1-5.
Stancato, et al., "Fingerprinting of signal transduction pathways using a combination of anti-phosphotyrosine immunoprecipitations and two-dimensional polycrylamide gel electrophoresis," Electrophoresis, 2001, 22:2120-2124.
Szöllösi, et al., "Applications of fluorescence resonance energy transfer for mapping biological membranes," Reviews in Molecular Biotechnology, 2002, 82:251-266.
Traxler, "Tyrosine kinases as targets in cancer therapy—successes and failures," Expert Opin. Ther. Targets, 2003, 7:215-234.
Wallasch, et al., "Heregulin-dependent regulation of HER2/neu oncogenic signaling by heterodimerization with HER3," The EMBO Journal, 1995, 14:4267-4275.
Weng, et al., "Complexity in Biological Signaling Systems," Science, 1999, 284:92-96.
Wu, et al., "Immunoflourescent labeling of cancer marker Her2 and other cellular targets with semiconductor quantum dots," Nature Biotechnology, 2003, 21:4146.
Xenarios, et al., "DIP: the Database of Interacting Proteins," Nucleic Acid Research, 2000, 28:289-291.
Xenarios, et al., "DIP,the Database of Interacting Proteins: a research tool for studying cellular networks of protein interactions," Nucleic Acid Research, 2002, 30:303-305.
Xenarios, et al., "Protein interaction databases," Current Opinion in Biotechnology, 2001, 12:334-339.

Xia, et al, "Combination of EGFR, HER-2/neu, and HER-3 Is a Stronger Predictor for the Outcome of Oral Squamous Cell Carcinoma Than Any Individual Family Members," Clinical Cancer Research, 1999, 5:4164-4174.
Yan, et al., "Analysis of protein interactions using fluorescence technologies," Current Opinion in Chemical Biology, 2003, 7:635-640.
Yarden, "The EGFR family and its ligands in human cancer: signalling mechanisms and therapeutic opportunities," European Journal of Cancer, 2001, 37:S3-S8.
Yarden, et al., "Untangling the ErbB Signalling Network," Molecular Cell Biology, 2001, 2:127-137.
Yarmush, et al., "Advances in Proteomic Technologies," Annu. Rev. Biomed. Eng. 2002, 4:349-373.
Yen, et al., "Differential Regulation of Tumor Angiogenesis by Distinct Erb B Homo- and Heterodimers," Molecular Biology of the Cell, 2002, 13:4029-4044.
Yu, et al., "Ligand-independent Dimer Formation of Epidermal Growth Factor Receptor (EGFR) Is a Step Separable from Ligand-induced EGFR Signaling," Molecular Biology of the Cell, 2002, 13:2547-2557.
Zhang, et al., "Transformation of NIH 3T3 Cells by HER3 or HER4 Receptors Requires the Presence of HERI or HER2," The Journal of Biological Chemistry, 1996, 271:3884-3890.
Fitch et al., "Improved Methods for Encoding and Decoding Dialkylamine-Encoded Combinatorial Libraries," J. Comb. Chem, 1, 1999, pp. 188-194.
Giese, "Electrophoric Release Tags: Ultrasensitive Molecular Labels Providing Multiplicity," Trends in Analytical Chemistry, vol. 2, No. 7, 1983, pp. 166-168.
Kochevar et al., "Photosensitized Production of Singlet Oxygen," Methods in Enzymology, vol. 319, 2000, pp. 20-29.
Liu et al., "Capillary Electrochromatography-laser-induced Fluorescence Method for Separation and Detection of Dansylated Dialkylamine Tags in Encoded Combinatorial Libraries," Journal of Chromatorgraphy, Art. 924, 2001, pp. 323-329.
Lum et al., "Ability of Specific Monoclonal Antibodies and Conventional Antisera Conjugated to Hematoporphyrin to Label and Kill Selected Cell Lines Subsequent to Light Activation," Cancer Research, vol. 45, 1985, pp. 4380-4386.
Ni et al., "Versatile Approach to Encoding Combinatorial Organic Synthesis Using Chemically Robust Secondary Amine Tags," J. Med. Chem., vol. 39, 1996, pp. 1601-1608.
Olejnik et al., "Photocleavable Affinity Tags for Isolation and Detection of Biomolecules," Methods in Enzymology, vol. 291, 1998, pp. 135-154.
Oseroff et al., "Antibody-Targeted Photolysis: Selective photodestruction of Human T-Cell Leukemia Cells Using Monoclonal Antibody-Chlorin $e_6$ Conjugates," Proc. Natl. Acad. Sci. USA, vol. 83, 1986, s. 8744-8748.
Rakestraw et al., "Antibody-Targeted photolysis: In vitro Studies with Sn(IV) Chlorin e6 Covalently Bound to Monoclonal Antibodies Using a Modified Dextran Carrier," Proc. Natl. Acad. Sci. USA vol. 87, 1990, pp. 4217-4221.
Da Ros et al., "DNA-Photocleavage Agents," Current Pharmaceutical Design, vol. 7, 2001, pp. 1781-1821.
Sharman et al., "Role of Activated Oxygen Species in Phothodynamic Therapy," Methods in Enzymology, vol. 319, 2000, pp. 376-400.
Still, "Discovery of Sequence-Selective Peptide Binding by Synthetic Receptors Using Encoded Combinatorial Libraries," Acc. Chem Res., vol. 29, 1996, pp. 155-163.
Strong, "Antibody-Targeted Photolysis," Annals New York Academy of Sciences, vol. 745, 1994, pp. 297-320.
Ullman et al., "Luminescent Oxygen Channeling Immunoassay: Measurement of Particle Binding Kinetics by Chemiluminescence," Proc. Natl. Acad. Sci. USA, vol. 91, 1994, pp. 5426-5430.
Yarmush et al., "Antibody Targeted Photolysis," Critical Reviews in Therapeutic Drug Carrier Systems, vol. 10, 1993, pp. 197-252.
Yemul et al., "Selective Killing of T Lymphocytes by Phototoxic Liposomes," Proc. Natl. Acad. Sci. USA, vol. 84, 1987, pp. 246-250.
X.C. Hu et al., "Immunomagnetic Tumor Cell Enrichment is Promising in Detecting Circulating Breast Cancer Cells," Oncology, 2003; 64:160-165.
Moreno et al, "Changes in Circulating Carcinoma Cells in Patients with Metastatic Prostate Cancer Correlate with Disease Status," Adult Urology, 58 (3), 2001.
Zigeuner et al, "Isolation of Circulating Cancer Cells From Whole Blood by Immumomagne is Cell Enrichment and Unenriched Immunocytochemistry in Vitro," The Journal of Urology, Vo. 169, Feb. 2003, 701-705.
Ghossein et al., "Molecular Detection and Charaterization of Circulating Tumor Cells and Micrometastases in Prostatic, Urothelial, and Renal Cell Carcinomas" Seminars in Surgical Oncology, 2001, 20:304-311.
Bong Kyung Shin, "Proteomics Approaches to Uncover the Repertoire of Circulating Biomarkers for Breast Cancer," Journal of Mammary Gland Biology and Neoplsia, vol. 7, No. 4, Oct. 2002.
Emilian Racila, et al, "Detection and Charaterization of Carcinoma Cells in the Blood," Proc. Natl. Acad. Sci. USA, vol. 95, pp. 4589-4594, Apr. 1998.
Ivo Safarik, et al, "Use of Magnetic Techniques for the Isolation of Cells," Journal of Chromatography B., 722 (1999) 33-53.
Devi, "Heterodimerization of G-protein-coupled receptors: pharmacology, signaling and trafficking," Trends in Pharmacological Sciences, 22: 532-537 (2001).
George et al, "G-protein-coupled receptor oligomerization and its potential for drug discovery," Nature Reviews Drug Discovery, 1:808-820 (2002).
Mellado et al, "Chemokine signaling and functional responses: the role of receptor dimerization and TK pathway activation," Annu. Rev. Immunol., 19: 397-421 (2001).
Rowinsky, "The ErbG Family: Targets for therapeutic development against cancer and therapeutic strategies using monoclonal antibodies and tyrosine kinase inhibitors," Annu. Rev. Med., 55: 433-457 (2004).
Joppich-Kuhn et al, "Release Tags: A new class of analytical reagents," Clin. Chem., 28: 1844-1847 (1982).
Bertino, "Editorial: Target Signal Transduction," Horizons in Cancer Therapeutics: From Bench to Bedside, 2:2 (2001).
McVey et al, "Monitoring receptor oligomerization using time-resolved fluorescence resonance energy transfer and bioluminescence resonance energy transfer," J. Biol. Chem., 276: 14092-14099 (2001).
Gomes et al, "G Protein Coupled Receptor Dimerization: Implications in Modulating Receptor Function," J. Mol. Med., 2001, 79, 226-242.
Salim et al, "Oligomerization of G-protein-coupled Receptors Shown by Selective Co-immunoprecipitation," Journal of Biological Chemistry, 2002, vol. 277, No. 18, Issue of May 3, 2002, 15482-15485.
Angers et al, "Detection of $\exists_2$-Adrenergic Receptor Dimerization in Living Cells Using Bioluminescence Resonance Energy Transfer (BRET)," PNAS, Mar. 28, 2000, vol. 97, No. 7, 3684-3689.
Jordan et al., "G-protein-coupled Receptor heterodimerization Modulates Receptor Function" Nature, Jun. 17, 1999, vol. 399, 697-700.
Hudelist, G. et al., "Co-Expression of erbB-Family Members in Human Breast Cancer: Her-2/neu is the Preferred Candidate in Nodal-Positive Tumors," Breast Cancer Research and Treatment, 2003, pp. 353-361, vol. 80.
Lundy, J. et al., "Expression of neu Protein, Epidermal Growth Factor Receptor, and Transforming Growth Factor Alpha in Breast Cancer," American Journal of Pathology, Jun. 1991, pp. 1527-1534, vol. 138, No. 6.
Yarden, Y., "Biology of HER2 and Its Importance in Breast Cancer," Oncology, 2001, pp. 1-13, vol. 61 (suppl. 2).
Autiero et al., "Role of PIGF in the Intra- and Intermolecular Cross Talk Between VEGF Receptors Flt1 and Flk1 ," Nature Medicine, Jun. 8, 2003, pp. 936-943, vol. 9.
Burmer, G.C. et al., Frequency and Spectrum of c-Ki-ras Mutations in Human Sporadic Colon Carcinoma, Carinomas Arising in Ulcerative Colitis, and Pancreatic Adenocarcinoma, Environmental Health Perspectives, 1991, pp. 27-31, vol. 93.
Buskens, C. et al., "Adenocarcinomas of the Gastro-Esophageal Junction: A Comparative Study of the Gastric Cardia and the Esophagus with Respect to Cycloxygenase-2 Expression," Digestive Disease Week Abstracts and Itinerary Planner, 2003, Abstract No. 850.
Drexler, H.G. et al., "Recent Results on the Biology of Hodgkin and Reed-Sternberg Cells, II. Continuous Cell Lines," Leukemia and Lymphoma, 1993, pp. 1-25, vol. 9.
Embleton, M.J. et al., "Monoclonal Antibodies to Osteogenic Sacroma Antigens," Immunol. Ser., 1984, pp. 181-207, vol. 23.
European Examination Report, European Application EP 03771670.1, Dec. 14, 2007, 4 pages.
European Examination Report, European Application EP 03771670.1, Mar. 8, 2007, 6 pages.
European Search Report, European Application EP 03771670.1, Jul. 18, 2006, 2 pages.
Hsu, T.C., "Karyology of Cells in Culture," Tissue Culture Methods and Applications, Kruse and Patterson, Eds., Academic Press, N.Y., 1973, p. 764.
Kunkel, P. et al., "Expression and Localization of Scatter Factor/Hepatocyte Growth Factor in Human Astrocytomas," Neuro-Oncology, Apr. 2001, pp. 82-88, vol. 3, No. 2.
Montesano, R. et al., "Genetic Alterations in Esophageal Cancer and Their Relevance to Etiology and Pathogenesis: A Review," Intl. J. Cancer, 1996, pp. 225-235, vol. 69, No. 3.
Slamon, D.J. et al., "Human Breast Cancer: Correlation of Relapse and Survival with Amplification of the HER-2/neu Oncogene," Science, Jan. 1987, pp. 177-182, vol. 235. Issue 4785.
Tian, J. et al "The Expression of Native and Cultured RPE Grown on Difference Matrices," Physiol. Genomics, Feb. 24, 2004, pp. 170-182, vol. 17.
Tockman, M.S. et al., "Considerations in Bringing a Cancer Biomarker to Clinical Application," Cancer Research, May 1, 1992 pp. 2711s-2718s, vol. 52.
Van Dyke, D. et al., "Monosomy 21 in Hematologic Diseases," Cancer Genetics and Cytogenetics, 2003, pp. 137-141, vol. 241.
Whitaker, G.B. et al., "Vascular Endothelial Growth Factor Receptor-2 and Neuropilin-1 Form a Receptor Complex That Is Responsible for the Differential Signaling Potency of $VEGF_{165}$ and $VEGF_{121}$," The Journal of Biological Chemistry, Jul. 6, 2001, pp. 25520-25531, vol. 276.
Wildi, S. et al., "Overexpression of Activin A in Stage IV Colorectal Cancer," Gut Online, Spe. 2001, pp. 409-471, vol. 49.
Zaslav, A.L. et al., "Significance of a Prenatally Diagnosed del(10)(q23)," American Journal of Medical Genetics, 2002, pp. 174-176, vol. 107.

* cited by examiner

| Assay | Receptor-Specific Antibody | | | Membrane |
|---|---|---|---|---|
| | 1 | 2 | 3 | |
| I | PS | $T_2$ | $T_3$ | + |
| II | ---- | $T_2$ | $T_3$ | + |
| III | PS | --- | $T_3$ | + |
| IV | PS | $T_2$ | --- | + |
| V | PS | $T_2$ | --- | - |

METHODS FOR DETECTING RECEPTOR COMPLEXES COMPRISING PI3K

Matter enclosed in heavy brackets [ ] appears in the original patent but forms no part of this reissue specification; matter printed in italics indicates the additions made by reissue.

This is a continuation of U.S. patent application Ser. No. 10/813,417, filed Mar. 30, 2004, now abandoned which is a continuation-in-part of U.S. patent application Ser. No. 10/623,057 filed 17 Jul. 2003 now U.S. Pat. No. 7,105,308; benefit of priority is further claimed under U.S. provisional applications Ser. No. 60/459,888 filed 1 Apr. 2003; Ser. No. 60/494,482 filed 11 Aug. 2003; Ser. No. 60/508,034 filed 1 Oct. 2003; Ser. No. 60/512,941 filed 20 Oct. 2003; and Ser. No. 60/523,258 filed 18 Nov. 2003, all of the above of which are incorporated in their entirety by reference.

FIELD OF THE INVENTION

The present invention relates generally to biomarkers, and more particularly, to the use of ErbB cell surface receptor complexes, such as dimers and oligomers, as biomarkers.

BACKGROUND OF THE INVENTION

A biomarker is a characteristic that is objectively measured and evaluated as an indicator of normal biological processes, pathogenic processes, or pharmacological responses to a therapeutic intervention, Atkinson et al, Clin. Pharmacol. Ther., 69: 89-95 (2001). Biomarkers vary widely in nature, ease of measurement, and correlation with physiological states of interest, e.g. Frank et al, Nature Reviews Drug Discovery, 2: 566-580 (2003). It is widely believed that the development of new validated biomarkers will lead both to significant reductions in healthcare and drug development costs and to significant improvements in treatment for a wide variety of diseases and conditions. Thus, a great deal of effort has been directed to using new technologies to find new classes of biomarkers, e.g. Petricoin et al, Nature Reviews Drug Discovery, 1: 683-695 (2002); Sidransky, Nature Reviews Cancer, 2: 210-219 (2002).

The interactions of cell surface membrane components play crucial roles in transmitting extracellular signals to a cell in normal physiology, and in disease conditions. In particular, many types of cell surface receptors undergo dimerization, oligomerization, or clustering in connection with the transduction of an extracellular event or signal, e.g. ligand-receptor binding, into a cellular response, such as proliferation, increased or decreased gene expression, or the like, e.g. George et al, Nature Reviews Drug Discovery, 1: 808-820 (2002); Mellado et al, Ann. Rev. Immunol., 19: 397-421 (2001); Schlessinger, Cell, 103: 211-225 (2000); Yarden, Eur. J. Cancer, 37: S3-S8 (2001). The role of such signal transduction events in diseases, such as cancer, has been the object of intense research and has led to the development of several new drugs and drug candidates, e.g. Herbst and Shin, Cancer, 94: 1593-1611 (2002); Yarden and Sliwkowski, Nature Reviews Molecular Cell Biology, 2: 127-137 (2001); McCormick, Trends in Cell Biology, 9: 53-56 (1999); Blume-Jensen and Hunter, Nature, 411: 355-365 (2001).

Expression levels of individual cell surface receptors have been used successfully as biomarkers, e.g. Slamon et al, U.S. Pat. No. 4,968,603 (Her2 expression). However, individual receptor expression level alone is not always a reliable indicator of a disease status or condition, e.g. Chow et al, Clin. Cancer Res., 7: 1957-1962 (2001) (EGFR, or Her1, expression). Despite the important role that receptor dimerization plays in cellular and disease processes, receptor dimer expression has not been employed as a biomarker, in part due to the inconvenience and lack of sensitivity of current measurement technologies and the inability or impracticality of using such technologies to carry out measurements on patient samples, which may be formalin fixed and/or in too small a quantity for analysis, e.g. Price et al, Methods in Molecular Biology, 218: 255-267 (2003); Stagljar, Science STKE 2003, pe56 (2003); Koll et al, International patent publication WO 2004/008099; Golemis, editor, Protein-Protein Interactions (Cold Spring Harbor Laboratory Press, New York, 2002); Sorkin et al, Curr. Biol., 10: 1395-1398 (2000); McVey et al, J. Biol. Chem., 17: 14092-14099 (2001); Salim et al, J. Biol. Chem., 277: 15482-15485 (2002); Angers et al, Annu. Rev. Pharmacol. Toxicol., 42: 409-435 (2002); Szollosi et al, Reviews in Molecular Biotechnology, 82: 251-266 (2002); Matko et al, Meth. in Enzymol., 278: 444-462 (1997); Reed-Gitomer, U.S. Pat. No. 5,192,660.

In view of the above, the availability of a new class of biomarkers in patient samples based on the presence, absence, and/or profile or ratios of cell surface receptor dimers or complexes involved with key intracellular processes, such as signal transduction, would advance the field of medicine by providing a new tool for diagnosis, prognosis, patient stratification, and drug development.

SUMMARY OF THE INVENTION

The invention is directed to biomarkers comprising ErbB receptor complexes in cell surface membranes of patient cell or tissue samples, particularly samples preserved by conventional procedures, such as freezing or fixation. In one aspect, the invention includes a method of determining the status of a disease or healthful condition by correlating such condition to amounts of one or more ErbB receptor complexes in cell surface membranes in a cell or tissue sample from an individual. In another aspect, the invention includes a method of determining a status of a cancer in a specimen from an individual by correlating measurements of amounts of one or more ErbB surface receptor complexes in the specimen to such status. The invention additionally provides a method of predicting the effectiveness of ErbB-dimer-acting drugs, for example, in cancer therapy, by relating numbers and types of drug-responsive ErbB dimers to efficacy, or a likelihood of patient responsiveness.

In one aspect, the invention permits the determination of a disease status of a patient suffering from a disease characterized by aberrant expression of one or more ErbB cell surface receptor complexes by the following steps: (i) measuring an amount of each of one or more ErbB cell surface receptor complexes in a patient sample; (ii) comparing each such amount to its corresponding amount in a reference sample; and (iii) correlating differences in the amounts from the patient sample and the respective corresponding amounts from the reference sample to the disease status the patient. A patient sample may be fixed or frozen; however, preferably, a patient sample is fixed using conventional protocols.

In a particular aspect, the invention provides a method of determining from measurements on patient samples, especially fixed samples, the disease status of a patient suffering from a cancer, wherein such measurement are of the types and/or amounts of ErbB receptor complexes, which are also referred to herein as "Her receptor complexes." Such receptor complexes include, but are not limited to, one or more of Her1-Her1 homodimers, Her2-Her2 homodimers, Her1-Her2 receptor dimers, Her2-Her3 receptor dimers, Her1-Her3 receptor dimers, Her2-Her4 receptor dimers, Her1-PI3K complexes, Her2-PI3K complexes, Her3-PI3K complexes, Her1-SHC complexes, Her2-SHC complexes, Her3-SHC complexes, Her1-IGF-1R receptor dimers, Her2-IGF-1R receptor dimers, Her3-IGF-1R receptor dimers, Her1-PDGFR receptor dimers, Her2-PDGFR receptor dimers, Her3-PDGFR receptor dimers, p95Her2-Her3 receptor dimers, p95Her2-Her2 receptor dimers, p95Her2-Her1 receptor dimers, EGFRvIII-Her1 receptor dimers, EGFRvIII-Her2 receptor dimers, and EGFRvIII-Her3 receptor dimers. In other embodiments, such Her receptor complexes are selected from the group consisting of Her1-Her2 receptor dimers and Her2-Her3 receptor dimers; or the group consisting of Her1-Her2 receptor dimers, Her2-Her3 receptor dimers, and Her1-Her3 receptor dimers. In another embodiment, the invention includes measurement of complexes comprising a Her receptor and an intracellular adaptor molecule, particularly, intracellular adaptor molecules that form complexes with a Her receptor in response to phosphorylation of such receptor. Exemplary receptor complexes of Her receptors and intracellular adaptor molecules include complexes selected from the group consisting of Her1-PI3K complexes, Her2-PI3K complexes, Her3-PI3K complexes, Her1-SHC complexes, Her2-SHC complexes, and Her3-SHC complexes. The invention further includes the association of receptor heterodimers comprising a Her receptor and another receptor tyrosine kinase to a disease status. Exemplary receptor complexes of Her receptors and other receptor tyrosine kinases include receptor complexes selected from the group consisting of Her1-IGF-1R receptor dimers, Her2-IGF-1R receptor dimers, Her3-IGF-1R receptor dimers, Her1-PDGFR receptor dimers, Her2-PDGFR receptor dimers, and Her3-PDGFR receptor dimers. The invention further includes the association of receptor dimers comprising a full-length Her receptor and a truncated Her receptor to a disease status. Exemplary receptor complexes of full-length Her receptors and truncated Her receptors include receptor complexes selected from group consisting of p95Her2-Her3 receptor dimers, EGFRvIII-Her1 receptor dimers, EGFRvIII-Her2 receptor dimers, and EGFRvIII-Her3 receptor dimers. In another aspect, such method of determining disease status includes determining the effectiveness of, or the responsiveness of a patient to, dimer-acting drugs for treating cancer, the dimer-acting drug acting on Her receptor complexes as described above.

In another aspect the invention includes improved determinations of a disease status by measuring expression of Her1-Her3 receptor complexes in a patient sample, as well as expression of Her1-Her2 and Her2-Her3 receptor complexes.

In another aspect, the invention provides a method of determining a status of a cancer in a patient by determining amounts of one or more dimers of ErbB cell surface membrane receptors or relative amounts of a plurality of dimers of cell surface membrane receptors in a cell or tissue sample from such patient. In one embodiment, such dimers are measured using at least two reagents, referred to herein as reagent pairs, that are specific for different members of each dimer: one reagent, referred to herein as a cleaving probe, has a cleavage-inducing moiety that may be induced to cleave susceptible bonds within its immediate proximity; and the other reagent, referred to herein as a binding compound, has one or more molecular tags attach by linkages that are cleavable by the cleavage-inducing moiety. In accordance with the embodiment, whenever such different members form a dimer, the cleavable linkages are brought within the effective cleaving proximity of the cleavage-inducing moiety so that molecular tags are released. The released molecular tags are then separated from the reaction mixture and quantified to provide a measure of dimer formation.

In another aspect of the invention, ErbB receptor dimers in a patient sample are measured ratiometrically; that is, the amount of an ErbB dimer is given as a ratio of a measure of one component present in the dimer to a measure of the total amount of the other component of the dimer, whether it is present in the dimer or in monomeric form. In one embodiment, typical measures include peak height or peak area of peaks in an electropherogram that are correlated to particular molecular tags.

In a particular embodiment of this aspect, the invention provides a method of determining a status of a cancer in a patient by simultaneously determining amounts of a plurality of Her receptor dimers in a fixed tissue sample from the patient. Such dimers may be measured using at least two reagents that are specific for different members of each dimer: one reagent, referred to herein as a cleaving probe, has a cleavage-inducing moiety that may be induced to cleave susceptible bonds within its immediate proximity; and the other reagent, referred to herein as a binding compound, has one or more molecular tags attach by linkages that are cleavable by the cleavage-inducing moiety. In accordance with the embodiment, whenever Her receptor dimers form, the cleavable linkages of the binding compounds are brought within the effective cleaving proximity of the cleavage-inducing moiety so that molecular tags are released. The molecular tags are then separated from the reaction mixture and quantified to provide a measure of Her receptor dimer populations. In another embodiment of this aspect, relative amounts of a plurality of Her receptor dimers are measured and related to a status of a cancer in a patient. Exemplary cancers include, but are not limited to, breast cancer, ovarian cancer, and prostate cancer. Exemplary Her receptor dimers include, but are not limited to, Her1-Her2 receptor dimers, Her1-Her3 receptor dimers, Her2-Her3 receptor dimers, and Her2-Her4 receptor dimers, as well as those listed above.

The present invention provides biomarkers comprising measures of the amounts of ErbB receptor complexes in patient samples. In particular, profiles of ErbB receptor complex populations may be correlated to disease status of a patient, and in some embodiments, to prognosis, efficacy of ErbB dimer-acting drugs, and likelihood of patient responsiveness to therapy. In accordance with the invention, short comings in the art are overcome by enabling the direct measurement of ErbB receptor complexes in patient samples without the need to culture or otherwise process the cell or tissue samples by methodologies, such as xenografting, that increase cost and labor as well as introducing sources of noise and potential artifacts into the final assay readouts. The present invention also provides a surrogate measurement for intracellular receptor phosphorylation, or other modifications that are easily destroyed in sample preparation procedures. Such surrogate measurements are based on the measurement of complexes, such as PI3K or SHC-receptor complexes, and the like, that depend on the above modifications for their formation and that are less affected by sample preparation procedures.

DEFINITIONS

Figure 1A:
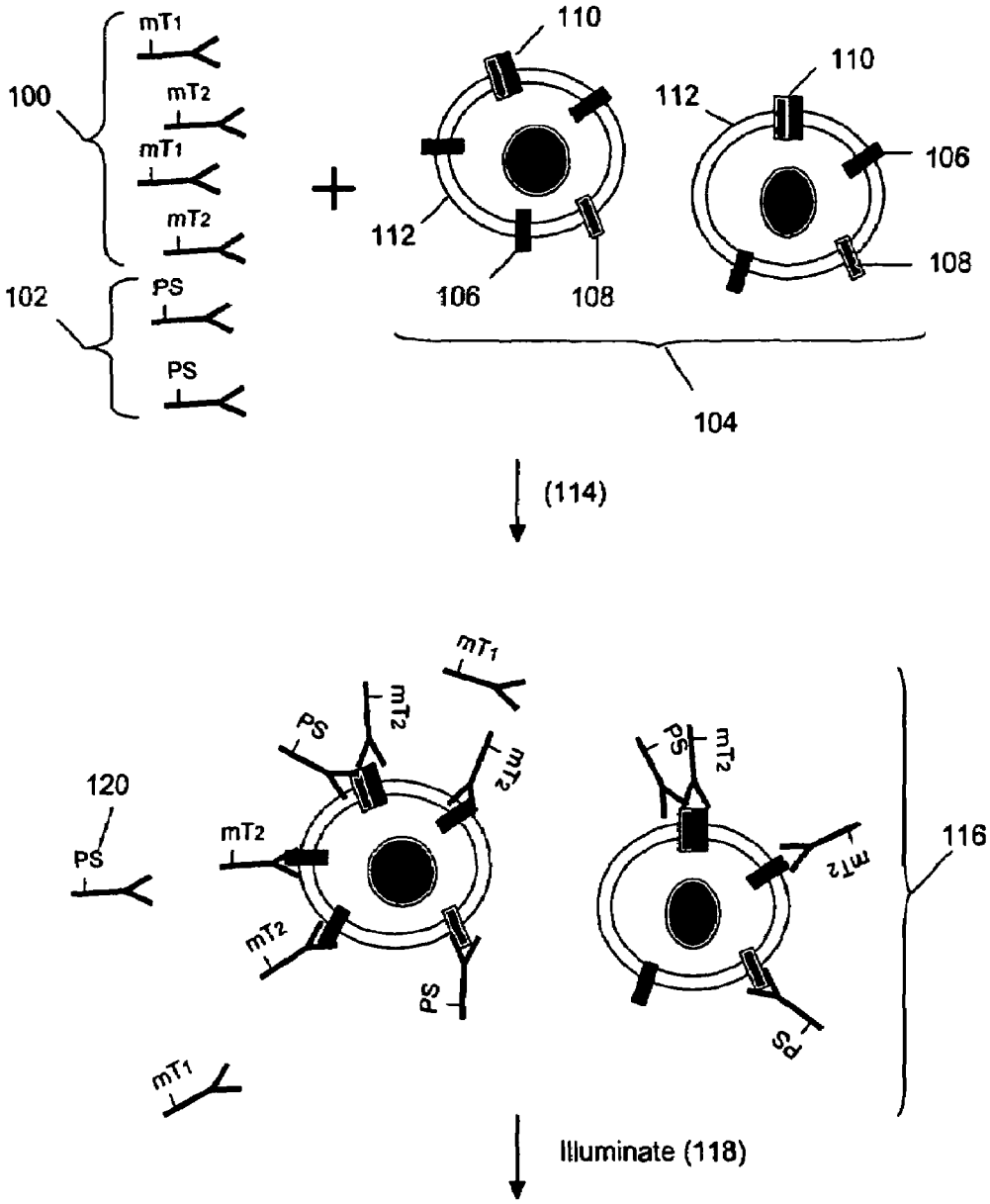
FIGS. 1A-1F illustrate diagrammatically the use of releasable molecular tags to measure receptor dimer populations.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained. Guidance in the production and selection of antibodies for use in immunoassays, including such assays employing releasable molecular tag (as described below) can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antibody binding composition" means a molecule or a complex of molecules that comprises one or more antibodies, or fragments thereof, and derives its binding specificity from such antibody or antibody fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photo sensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids, and organic molecules having a molecular weight of up to 1000 daltons and consisting of atoms selected from the group consisting of hydrogen, carbon, oxygen, nitrogen, sulfur, and phosphorus. Preferably, binding moieties are antibodies or antibody binding compositions.

"Cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer.

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins, and is equivalently referred to as a "protein-protein complex." Most typically, a "complex" refers to a stable aggregate of two proteins.

"Dimer" in reference to cell surface membrane receptors means a complex of two or more membrane-bound receptor proteins that may be the same or different. Dimers of identical receptors are referred to as "homodimers" and dimers of different receptors are referred to as "heterodimers." Dimers usually consist of two receptors in contact with one another. Dimers may be created in a cell surface membrane by passive processes, such as Van der Waal interactions, and the like, as described above in the definition of "complex," or dimers may be created by active processes, such as by ligand-induced dimerization, covalent linkages, interaction with intracellular components, or the like, e.g. Schlessinger, Cell, 103: 211-225 (2000). As used herein, the term "dimer" is understood to refer to "cell surface membrane receptor dimer," unless understood otherwise from the context.

"Disease status" includes, but is not limited to, the following features: likelihood of contracting a disease, presence or absence of a disease, prognosis of disease severity, and likelihood that a patient will respond to treatment by a particular therapeutic agent that acts through a receptor complex. In regard to cancer, "disease status" further includes detection of precancerous or cancerous cells or tissues, the selection of patients that are likely to respond to treatment by a therapeutic agent that acts through one or more receptor complexes, such as one or more receptor dimers, and the ameliorative effects of treatment with such therapeutic agents. In one aspect, disease status in reference to Her receptor complexes means likelihood that a cancer patient will respond to treatment by a Her, or ErbB, dimer-acting drug. Preferably, such cancer patient is a breast or ovarian cancer patient and such Her dimer-acting drugs include Omnitarg™ (2C4), Herceptin, ZD-1839 (Iressa), and OSI-774 (Tarceva).

"ErbB receptor" or "Her receptor" is a receptor protein tyrosine kinase which belongs to the ErbB receptor family and includes EGFR ("Her1"), ErbB2 ("Her2"), ErbB3 ("Her3") and ErbB4 ("Her4") receptors. The ErbB receptor generally comprises an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor. In one aspect, ErbB receptor includes truncated versions of Her receptors, including but not limited to, EGFRvIII and p95Her2, disclosed in Chu et al, Biochem. J., 324: 855-861 (1997); Xia et al, Oncogene, 23: 646-653 (2004); and the like.

The terms "ErbB1", "epidermal growth factor receptor" and "EGFR" and "Her1" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. Examples of antibodies which bind to EGFR include MAb 579 (ATCC CRL RB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

"Her2", "ErbB2" "c-Erb-B2" are used interchangeably. Unless indicated otherwise, the terms "ErbB2" "c-Erb-B2" and "Her2" when used herein refer to the human protein. The human ErbB2 gene and ErbB2 protein are, for example, described in Semba et al., PNAS (USA) 82:6497-650 (1985) and Yamamoto et al. Nature 319:230-234 (1986) (Genebank accession number X03363). Examples of antibodies that specifically bind to Her2 are disclosed in U.S. Pat. Nos. 5,677,171; 5,772,997; Fendly et al, Cancer Res., 50: 1550-1558 (1990); and the like.

"ErbB3" and "Her3" refer to the receptor polypeptide as disclosed, for example, in U.S. Pat. Nos. 5,183,884 and 5,480,968 as well as Kraus et al. PNAS (USA) 86:9193-9197 (1989), including variants thereof. Examples of antibodies which bind Her3 are described in U.S. Pat. No. 5,968,511, e.g. the 8B8 antibody (ATCC HB 12070).

The terms "ErbB4" and "Her4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993), including variants thereof such as the Her4 isoforms disclosed in WO 99/19488.

"Insulin-like growth factor-1 receptor" or "IGF-1R" means a human receptor tyrosine kinase substantially identical to those disclosed in Ullrich et al, EMBO J., 5: 2503-2512 (1986) or Steele-Perkins et al, J. Biol. Chem., 263: 11486-11492 (1988).

"Isolated" in reference to a polypeptide or protein means substantially separated from the components of its natural environment. Preferably, an isolated polypeptide or protein is a composition that consists of at least eighty percent of the polypeptide or protein identified by sequence on a weight basis as compared to components of its natural environment; more preferably, such composition consists of at least ninety-five percent of the polypeptide or protein identified by sequence on a weight basis as compared to components of its natural environment; and still more preferably, such composition consists of at least ninety-nine percent of the polypeptide or protein identified by sequence on a weight basis as compared to components of its natural environment. Most preferably, an isolated polypeptide or protein is a homogenous composition that can be resolved as a single spot after conventional separation by two-dimensional gel electrophoresis based on molecular weight and isoelectric point. Protocols for such analysis by conventional two-dimensional gel electrophoresis are well known to one of ordinary skill in the art, e.g. Hames and Rickwood, Editors, Gel Electrophoresis of Proteins: A Practical Approach (IRL Press, Oxford, 1981); Scopes, Protein Purification (Springer-Verlag, New York, 1982); Rabilloud, Editor, Proteome Research: Two-Dimensional Gel Electrophoresis and Identification Methods (Springer-Verlag, Berlin, 2000).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Percent identical," or like term, used in respect of the comparison of a reference sequence and another sequence (i.e. a "candidate" sequence) means that in an optimal alignment between the two sequences, the candidate sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms described by Needleman and Wunsch, J. Mol. Biol., 48: 443-453 (1970) ("GAP" program of Wisconsin Sequence Analysis Package, Genetics Computer Group, Madison, Wis.). Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polypeptide having an amino acid sequence at least 95 percent identical to a reference amino acid sequence, up to five percent of the amino acid residues in the reference sequence many be deleted or substituted with another amino acid, or a number of amino acids up to five percent of the total amino acid residues in the reference sequence may be inserted into the reference sequence. These alterations of the reference sequence many occur at the amino or carboxy terminal positions of the reference amino acid sequence or anywhere between those terminal positions, interspersed either individually among residues in the reference sequence of in one or more contiguous groups with in the references sequence. It is understood that in making comparisons with reference sequences of the invention that candidate sequence may be a component or segment of a larger polypeptide or polynucleotide and that such comparisons for the purpose computing percentage identity is to be carried out with respect to the relevant component or segment.

"Phosphatidylinositol 3 kinase protein," or equivalently a "PI3K protein," means a human intracellular protein of the set of human proteins describe under NCBI accession numbers NP_852664, NP_852556, and NP_852665, and proteins having amino acid sequences substantially identical thereto.

"Platelet-derived growth factor receptor" or "PDGFR" means a human receptor tyrosine kinase protein that is substantially identical to PDGFRα or PDGFRβ, or variants thereof, described in Heldin et al, Physiological Reviews, 79: 1283-1316 (1999). In one aspect, the invention includes determining the status of cancers, pre-cancerous conditions, fibrotic or sclerotic conditions by measuring one or more dimers of the following group: PDGFRα homodimers, PDGFRβ homodimers, and PDGFRα-PDGFRβ heterodimers. In particular, fibrotic conditions include lung or kidney fibrosis, and sclerotic conditions include atherosclerosis. Cancers include, but are not limited to, breast cancer, colorectal carcinoma, glioblastoma, and ovarian carcinoma. Reference to "PDGFR" alone is understood to mean "PDGFRα" or "PDGFRβ."

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, farnesylation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1-12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, and the like.

"Reference sample" means one or more cell, xenograft, or tissue samples that are representative of a normal or non-diseased state to which measurements on patient samples are compared to determine whether a receptor complex is present in excess or is present in reduced amount in the patient sample. The nature of the reference sample is a matter of design choice for a particular assay and may be derived or determined from normal tissue of the patient him- or herself, or from tissues from a population of healthy individuals. Preferably, values relating to amounts of receptor complexes in reference samples are obtained under essentially identical experimental conditions as corresponding values for patient samples being tested. Reference samples may be from the same kind of tissue as that the patient sample, or it may be from different tissue types, and the population from which reference samples are obtained may be selected for characteristics that match those of the patient, such as age, sex, race, and the like. Typically, in assays of the invention, amounts of receptor complexes on patient samples are compared to corresponding values of reference samples that have been previously tabulated and are provided as average ranges, average values with standard deviations, or like representations.

"Receptor complex" means a complex that comprises at least one cell surface membrane receptor. Receptor complexes may include a dimer of cell surface membrane receptors, or one or more intracellular proteins, such as adaptor proteins, that form links in the various signaling pathways. Exemplary intracellular proteins that may be part of a receptor complex includes, but is not limit to, PI3K proteins, Grb2 proteins, Grb7 proteins, Shc proteins, and Sos proteins, Src proteins, Cb1 proteins, PLCγ proteins, Shp2 proteins, GAP proteins, Nck proteins, Vav proteins, and Crk proteins. In one aspect, receptor complexes include PI3K or Shc proteins.

"Receptor tyrosine kinase," or "RTK," means a human receptor protein having intracellular kinase activity and being selected from the RTK family of proteins described in Schlessinger, Cell, 103: 211-225 (2000); and Blume-Jensen and Hunter (cited above). "Receptor tyrosine kinase dimer" means a complex in a cell surface membrane comprising two receptor tyrosine kinase proteins. In some aspects, a receptor tyrosine kinase dimer may comprise two covalently linked receptor tyrosine kinase proteins. Exemplary RTK dimers are listed in Table I. RTK dimers of particular interest are Her receptor dimers and VEGFR dimers.

"Sample" or "tissue sample" or "patient sample" or "patient cell or tissue sample" or "specimen" each means a collection of similar cells obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. In one aspect of the invention, tissue samples or patient samples are fixed, particularly conventional formalin-fixed paraffin-embedded samples. Such samples are typically used in an assay for receptor complexes in the form of thin sections, e.g. 3-10 μm thick, of fixed tissue mounted on a microscope slide, or equivalent surface. Such samples also typically undergo a conventional re-hydration procedure, and optionally, an antigen retrieval procedure as a part of, or preliminary to, assay measurements.

"Separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Electropherograms may be analyzed to associate features in the data with the presence, absence, or quantities of molecular tags using analysis programs, such as disclosed in Williams et al, U.S. patent publication 2003/0170734 A1.

"SHC" (standing for "Src homology 2/α-collagen-related") means any one of a family of adaptor proteins (66, 52, and 46 kDalton) in RTK signaling pathways substantially identical to those described in Pelicci et al, Cell, 70: 93-104 (1992). In one aspect, SHC means the human versions of such adaptor proteins.

"Signaling pathway" or "signal transduction pathway" means a series of molecular events usually beginning with the interaction of cell surface receptor with an extracellular ligand or with the binding of an intracellular molecule to a phosphorylated site of a cell surface receptor that triggers a series of molecular interactions, wherein the series of molecular interactions results in a regulation of gene expression in the nucleus of a cell. "Ras-MAPK pathway" means a signaling pathway that includes the phosphorylation of a MAPK protein subsequent to the formation of a Ras-GTP complex. "PI3K-Akt pathway" means a signaling pathway that includes the phosphorylation of an Akt protein by a PI3K protein.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21-76, in Flow Cytometry: Instrumentation and Data Analysis (Academic Press, New York, 1985).

"Substantially identical" in reference to proteins or amino acid sequences of proteins in a family of related proteins that are being compared means either that one protein has an amino acid sequence that is at least fifty percent identical to the other protein or that one protein is an isoform or splice variant of the same gene as the other protein. In one aspect, substantially identical means one protein, or amino acid sequence thereof, is at least eighty percent identical to the other protein, or amino acid sequence thereof.

DETAILED DESCRIPTION OF THE INVENTION

The invention provides a method of using ErbB cell surface receptor complexes as biomarkers for the status of a disease or other physiological conditions in a biological organism, particularly a cancer status in a human. In one aspect, ErbB receptor complexes are measured directly from patient samples; that is, measurements are made without culturing, formation of xenografts, or the use of like techniques, that require extra labor and expense and that may introduce artifacts and/or noise into the measurement process. In a particular aspect of the invention, measurements of one or more receptor complexes are made directly on tissue lysates of frozen patient samples or on sections of fixed patient samples. In a preferred embodiment, one or more ErbB receptor complexes are measured in sections of formalin-fixed paraffin-embedded (FFPE) samples.

In another aspect, the invention provides an indirect measurement of ErbB receptor phosphorylation through the measurement of complexes that depend on such posttranslational modifications for their formation.

In one aspect, a plurality of ErbB receptor complexes, such as receptor dimers, are simultaneously measured in the same assay reaction mixture. Preferably, such complexes are measured using binding compounds having one or more molecular tags releasably attached, such that after binding to a protein in a complex, the molecular tags may be released and separated from the reaction, or assay, mixture for detection and/or quantification.

In one aspect, the invention provides a method for determining a disease status of a patient comprising the following steps: measuring an amount of each of one or more ErbB receptor dimers in a patient sample; comparing each such amount to its corresponding amount from a reference sample; and correlating differences in the amounts from the patient sample and the respective corresponding amounts from the reference sample to the presence or severity of a disease condition in the patient. In a preferred embodiment, the step of measuring comprising the steps of: (i) providing one or more binding compounds specific for a protein of each of the one or more receptor dimers, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (ii) mixing the binding compounds and the one or more complexes such that binding compounds specifically bind to their respective receptor dimers to form detectable complexes; (iii) cleaving the cleavable linkage of each binding compound forming detectable complexes, and (iv) separating and identifying the released molecular tags to determine the presence or absence or the amount of the one or more receptor dimers.

In another aspect, the step of measuring the amounts of one or more types of ErbB receptor dimer comprising the following steps: (i) providing for each of the one or more types of receptor dimer a cleaving probe specific for a first receptor in each of the one or more receptor dimers, each cleaving probe having a cleavage-inducing moiety with an effective proximity; (ii) providing one or more binding compounds specific for a second receptor of each of the one or more receptor dimers, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probes, the binding compounds, and the one or more types of receptor dimers such that cleaving probes specifically bind to first receptors of the receptor dimers and binding compounds specifically bind to the second receptors of the receptor dimers and such that cleavable linkages of the binding compounds are within the effective proximity of cleavage-inducing moieties of the cleaving probes so that molecular tags are released; and (iv) separating and identifying the released molecular tags to determine the presence or absence or the amount of the one or more types of receptor dimers. Preferably, receptor dimers and first and second receptors are selected from the receptor dimers listed in Table 1.

In another aspect of the invention, a biological specimen, which comprises a mixed cell population suspected of containing the rare cell of interest is obtained from a patient. A sample is then prepared by mixing the biological specimen with magnetic particles which are coupled to a biospecific ligand specifically reactive with an antigen on the rare cell that is different from or not found on blood cells (referred to herein as a "capture antigen"), so that other sample components may be substantially removed. The sample is subjected to a magnetic field which is effective to separate cells labeled with the magnetic particles, including the rare cells of interest, if any are present in the specimen. The cell population so isolated is then analyzed using molecular tags conjugated to binding moieties specific for biomarkers to determine the presence and/or number of rare cells. In a preferred embodiment the magnetic particles used in this method are colloidal magnetic nanoparticles. Preferably, such rare cell populations are circulating epithelial cells, which may be isolated from patient's blood using epithelial-specific capture antigens, e.g. as disclosed in Hayes et al, International J. of Oncology, 21: 1111-1117 (2002); Soria et al, Clinical Cancer Research, 5: 971-975 (1999); Ady et al, British J. Cancer, 90: 443-448 (2004); which are incorporated by reference. In particular, monoclonal antibody BerEP4 (Dynal A. S., Oslo, Norway) may be used to capture human epithelial cells with magnetic particles.

In another aspect, the invention provides a method for determining a cancer status of a patient comprising the following steps: (i) immunomagnetically isolating a patient sample comprising circulating epithelial cells by contacting a sample of patient blood with one or more antibody compositions, each antibody composition being specific for a capture antigen and being attached to a magnetic particle; (ii) measuring an amount of each of one or more ErbB receptor complexes in the patient sample; comparing each such amount to its corresponding amount from a reference sample; and correlating differences in the amounts from the patient sample and the respective corresponding amounts from the reference sample to the presence or severity of a cancer condition in the patient. In a preferred embodiment, the step of measuring comprises the steps of: (i) providing one or more binding compounds specific for a protein of each of the one or more ErbB receptor complexes, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (ii) mixing the binding compounds and the one or more ErbB receptor complexes such that binding compounds specifically bind to their respective proteins of the one or more ErbB receptor complexes to form detectable complexes; (iii) cleaving the cleavable linkage of each binding compound forming detectable complexes, and (iv) separating and identifying the released molecular tags to determine the presence or absence or the amount of the one or more ErbB receptor complexes.

In another aspect, the step of measuring the amounts of one or more ErbB receptor complexes comprising the following steps: (i) providing for each of the one or more ErbB receptor complexes a cleaving probe specific for a first protein in each of the one or more ErbB receptor complexes, each cleaving probe having a cleavage-inducing moiety with an effective proximity; (ii) providing one or more binding compounds specific for a second protein of each of the one or more ErbB receptor complexes, such that each binding compound has one or more molecular tags each attached thereto by a cleavable linkage, and such that the one or more molecular tags attached to different binding compounds have different separation characteristics so that upon separation molecular tags from different binding compounds form distinct peaks in a separation profile; (iii) mixing the cleaving probes, the binding compounds, and the one or more complexes such that cleaving probes specifically bind to first proteins of the ErbB receptor complexes and binding compounds specifically bind to the second proteins of the ErbB receptor complexes and such that cleavable linkages of the binding compounds are within the effective proximity of cleavage-inducing moieties of the cleaving probes so that molecular tags are released; and (iv) separating and identifying the released molecular tags to determine the presence or absence or the amount of the one or more ErbB receptor complexes.

Exemplary Receptor Dimer Biomarkers and Dimer-Acting Drugs

Biomarkers of the invention include dimers and oligomers of the following receptors.

TABLE I

Exemplary Receptor Complexes of Cell Surface Membranes

| Dimer |
|---|
| Her1-Her1 |
| Her1-Her2 |
| Her1-Her3 |
| Her1-Her4 |
| Her2-Her2 |
| Her2-Her3 |
| Her2-Her4 |
| Her3-Her4 |
| Her4-Her4 |
| Her2-PDGFR heterodimers |
| IGF-1R-Her2 heterodimer |
| IGF-1R-Her1 heterodimer |
| IGF-1R-Her3 heterodimer |
| Her1-PDGFR heterodimers |
| Her3-PDGFR heterodimers |
| Her2-P13K |
| Her1-SHC |
| Her3-SHC |
| Her2-SHC |
| Her3-P13K |
| Her1-P13K |

The mechanisms of action of many drugs that are in use or are under development require the inhibition of one or more functions of ErbB receptor dimers, such as the association of component receptors into a dimer structure, or a function, such as an enzymatic activity, e.g. kinase activity, or autophosphorylation, that depends on dimerization. Such drugs are referred to herein as "dimer-acting" drugs, or "ErbB dimer-acting" drugs. The number, type, formation, and/or dissociation of receptor dimers in the cells of a patient being treated, or whose treatment is contemplated, have a bearing on the effectiveness or suitability of using a particular ErbB dimer-acting drug. The following ErbB receptor dimers are biomarkers related to the indicated drugs. In one aspect, the invention provides biomarkers for monitoring the effect on disease status of an ErbB dimer-acting drug,

TABLE II

Drugs Associated with Dimers of Cell Surface Membranes

| Dimer | Drug(s) |
|---|---|
| Her1-Her1, Her1-Her2, Her1-Her3, Her1-Her4, Her1-IGF-1R, Her2-IGF-1R | Cetuximab (Erbitux), Trastuzumab (Herceptin), h-R3 (TheraCIM), ABX-EGF, MDX-447, ZD-1839 (Iressa), OSI-774 (Tarceva), PKI 166, GW572016, CI-1033, EKB-569, EMD 72000 |
| Her2-Her1, Her2-Her3, Her2-Her2, Her2-Her4 | 4D4 Mab, Trastuzumab (Herceptin), 2C4, GW572016 |

The following references describe the dimer-acting drugs listed in Table II: Traxler, Expert Opin. Ther. Targets, 7: 215-234 (2002); Baselga, editor, Oncology Biotherapeutics, 2: 1-36 (2002); Nam et al, Current Drug Targets, 4: 159-179 (2003); Seymour, Current Drug Targets, 2: 117-133 (2001); and the like.

TABLE III

P13K-Associated Receptor Complexes

| Dimer |
|---|
| Her1-Her1 |
| Her1-Her2 |
| Her1-Her3 |
| Her1-Her4 |
| Her2-Her2 |
| IGF-1R-Her2 heterodimer |
| Her3-PDGFR heterodimers |
| Her2-PDGFR heterodimers |
| IGF-1R-Her1 heterodimer |
| Her4-Her4 |
| Her3-Her4 |
| Her2-Her4 |
| Her2-Her3 |
| IGF-1R-Her3 heterodimer |
| Her1-PDGFR heterodimers |
| Her2-XX-P13K* |

*"XX" refers to any receptor Her2 is capable of forming a dimer with.

Preparation of Samples

Samples containing molecular complexes may come from a wide variety of sources for use with the present invention to relate receptor complexes populations to disease status or health status, including cell cultures, animal or plant tissues, patient biopsies, or the like. Preferably, samples are human patient samples. Samples are prepared for assays of the invention using conventional techniques, which may depend on the source from which a sample is taken.

A. Solid Tissue Samples. For biopsies and medical specimens, guidance is provided in the following references: Bancroft J D & Stevens A, eds. Theory and Practice of Histological Techniques (Churchill Livingstone, Edinburgh, 1977);

Pearse, Histochemistry. Theory and applied. 4th ed. (Churchill Livingstone, Edinburgh, 1980).

In the area of cancerous disease status, examples of patient tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, assays of the invention are carried out on tissue samples that have been fixed and embedded in paraffin or the like; therefore, in such embodiments a step of deparaffination is carried out. A tissue sample may be fixed (i.e. preserved) by conventional methodology [See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may have a thickness in a range from about three microns to about twelve microns, and preferably, a thickness in a range of from about 5 microns to about 10 microns. In one aspect, a section may have an area of from about 10 $mm^2$ to about 1 $cm^2$. Once cut, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De® (CMS, Houston, Tex.) may be used.

For mammalian tissue culture cells, fresh tissues, or like sources, samples may be prepared by conventional cell lysis techniques (e.g. 0.14 M NaCl, 1.5 mM $MgCl_2$, 10 mM Tris-Cl (pH 8.6), 0.5% Nonidet P-40, and protease and/or phosphatase inhibitors as required). For fresh mammalian tissues, sample preparation may also include a tissue disaggregation step, e.g. crushing, mincing, grinding, sonication, or the like.

B. Magnetic Isolation of Cells. In some applications, such as measuring dimers on rare metastatic cells from a patient's blood, an enrichment step may be carried out prior to conducting an assay for surface receptor dimer populations. Immunomagnetic isolation or enrichment may be carried out using a variety of techniques and materials known in the art, as disclosed in the following representative references that are incorporated by reference: Terstappen et al, U.S. Pat. No. 6,365,362; Terstappen et al, U.S. Pat. No. 5,646,001; Rohr et al, U.S. Pat. No. 5,998,224; Kausch et al, U.S. Pat. No. 5,665,582; Kresse et al, U.S. Pat. No. 6,048,515; Kausch et al, U.S. Pat. No. 5,508,164; Miltenyi et al, U.S. Pat. No. 5,691,208; Molday, U.S. Pat. No. 4,452,773; Kronick, U.S. Pat. No. 4,375,407; Radbruch et al, chapter 23, in Methods in Cell Biology, Vol, 42 (Academic Press, New York, 1994); Uhlen et al, Advances in Biomagnetic Separation (Eaton Publishing, Natick, 1994); Safarik et al, J. Chromatography B, 722: 33-53 (1999); Miltenyi et al, Cytometry, 11: 231-238 (1990); Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

Assays Using Releasable Molecular Tags

Many advantages are provided by measuring dimer populations using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: Singh et al, U.S. Pat. No. 6,627,400; U.S. patent publications Singh et al, 2002/0013126; and 2003/0170915, and Williams et al, 2002/0146726; and Chan-Hui et al, International patent publication WO 2004/011900, all of which are incorporated herein by reference. For example, a wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Sets of molecular tags are provided that are separated into distinct bands or peaks by a separation technique after they are released from binding compounds. Identification and quantification of such peaks provides a measure or profile of the kinds and amounts of receptor dimers. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality for measuring populations of receptor dimers is in the range of from 2 to 10. In other aspects, the size of the plurality may be in the range of from 2 to 8, 2 to 6, 2 to 4, or 2 to 3.

Receptor dimers may be detected in assays having homogeneous formats or a non-homogeneous, i.e. heterogeneous, formats. In a homogeneous format, no step is required to separate binding compounds specifically bound to target complexes from unbound binding compounds. In a preferred embodiment, homogeneous formats employ reagent pairs comprising (i) one or more binding compounds with releasable molecular tags and (ii) at least one cleaving probe that is capable of generating an active species that reacts with and releases molecular tags within an effective proximity of the cleaving probe.

Receptor dimers may also be detected by assays employing a heterogeneous format. Heterogeneous techniques normally involve a separation step, where intracellular complexes having binding compounds specifically bound are separated from unbound binding compounds, and optionally, other sample components, such as proteins, membrane fragments, and the like. Separation can be achieved in a variety of ways, such as employing a reagent bound to a solid support that distinguishes between complex-bound and unbound binding compounds. The solid support may be a vessel wall, e.g., microtiter well plate well, capillary, plate, slide, beads, including magnetic beads, liposomes, or the like. The primary characteristics of the solid support are that it (1) permits segregation of the bound and unbound binding compounds and (2) does not interfere with the formation of the binding complex, or the other operations in the determination of receptor dimers. Usually, in fixed samples, unbound binding compounds are removed simply by washing.

With detection using molecular tags in a heterogeneous format, after washing, a sample may be combined with a solvent into which the molecular tags are to be released. Depending on the nature of the cleavable bond and the method of cleavage, the solvent may include any additional reagents for the cleavage. Where reagents for cleavage are not required, the solvent conveniently may be a separation buffer, e.g. an electrophoretic separation medium. For example, where the cleavable linkage is photolabile or cleavable via an active species generated by a photosensitizer, the medium may be irradiated with light of appropriate wavelength to release the molecular tags into the buffer.

In either format, if the assay reaction conditions interfere with the separation technique employed, it may be necessary to remove, or exchange, the assay reaction buffer prior to cleavage and separation of the molecular tags. For example, in some embodiments, assay conditions include salt concentrations (e.g. required for specific binding) that degrade separation performance when molecular tags are separated on the basis of electrophoretic mobility. In such embodiments, an assay buffer is replaced by a separation buffer, or medium, prior to release and separation of the molecular tags.

Assays employing releasable molecular tags and cleaving probes can be made in many different formats and configurations depending on the complexes that are detected or measured. Based on the present disclosure, it is a design choice for one of ordinary skill in the art to select the numbers and specificities of particular binding compounds and cleaving probes.

Figure 1B:
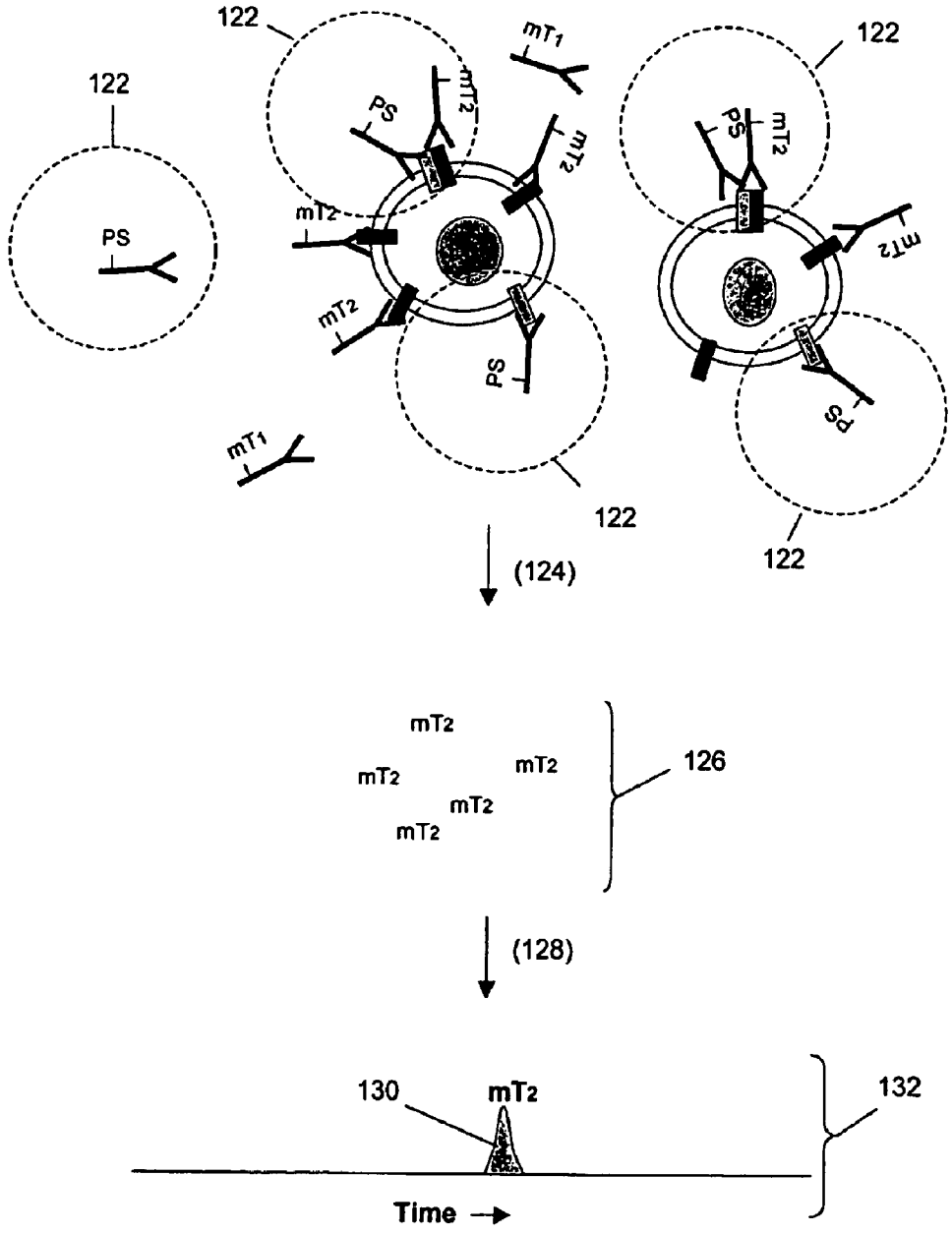

In one aspect of the invention, the use of releasable molecular tags to measure dimers of cell surface membranes is shown diagramnatically in FIGS. 1A and 1B. Binding compounds (100) having molecular tags "$mT_1$" and "$mT_2$" and cleaving probe (102) having photosensitizer "PS" are combined with biological cells (104). Binding compounds having molecular tag "$mT_1$" are specific for cell surface receptors $R_1$ (106) and binding compounds having molecular tag "$mT_2$" are specific for cell surface receptors $R_2$ (108). Cell surface receptors $R_1$ and $R_2$ are present as monomers, e.g. (106) and (108), and as dimers (110) in cell surface membrane (112). After these assay components are incubated in a suitable binding buffer to permit the formation (114) of stable complexes between binding compounds and their respective receptor targets and between the cleaving probe and its receptor target. As illustrated, preferably binding compounds and cleaving probes each comprise an antibody binding composition, which permits the molecular tags and cleavage-inducing moiety to be specifically targeted to membrane components. In one aspect, such antibody binding compositions are monoclonal antibodies. In such embodiments, binding buffers may comprise buffers used in conventional ELISA techniques, or the like. After binding compounds and cleaving probes for stable complexes (116), the assay mixture is illuminated (118) to induce photosensitizers (120) to generate singlet oxygen. Singlet oxygen rapidly reacts with components of the assay mixture so that its effective proximity (122) for cleaving cleavable linkages of molecular tags is spatially limited so that only molecular tags that happen to be within the effective proximity are released (124). As illustrated, the only molecular tags released are those on binding compounds that form stable complexes with $R_1$-$R_2$ dimers and a cleaving probe. Released molecular tags (126) are removed from the assay mixture and separated (128) in accordance with a separation characteristic so that a distinct peak (130) is formed in a separation profile (132). In accordance with the invention, such removal and separation may be the same step. Optionally, prior to illumination the binding buffer may be removed and replaced with a buffer more suitable for separation, i.e. a separation buffer. For example, binding buffers typically have salt concentrations that may degrade the performance of some separation techniques, such as capillary electrophoresis, for separating molecular tags into distinct peaks. In one embodiment, such exchange of buffers may be accomplished by membrane filtration.

Figure 1C:
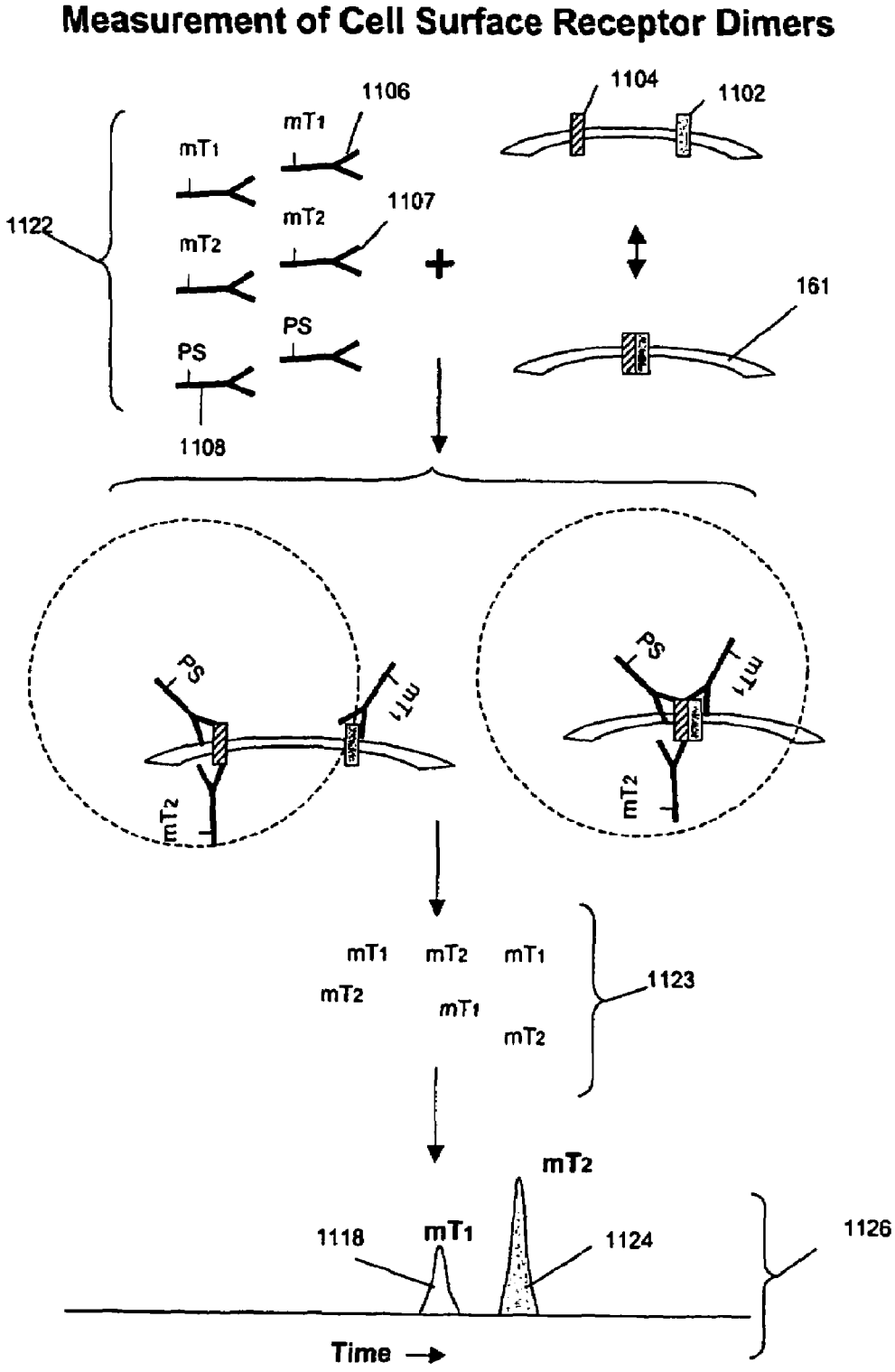

An embodiment that illustrates ratiometric measurement of heterodimers is illustrated in FIG. 1C, in which an additional binding compound is employed to give a measure of the total amount of protein (1104) in a sample. Reagents (1122) of the invention comprise (i) cleaving probes (1108), first binding compound (1106), and second binding compound (1107), wherein first binding compound (1106) is specific for protein (1102) and second binding compound (1107) is specific for protein (1104) at a different antigenic determinant than that cleaving probe (1108) is specific for. After binding of the reagents, cleaving probe (1108) is activated to produce active species that cleave the cleavable linkages of the molecular tags within the effective proximity of the photosensitizer. In this embodiment, molecular tags are released from monomers of protein (1104) that have both reagents (1107) and (1108) attached and from heterodimers that have reagent (1108) attached and either or both of reagents (1106) and (1107) attached. Released molecular tags (1123) are separated, and peaks (1118 and 1124) in a separation profile (1126) are correlated to the amounts of the released molecular tags. In this embodiment, relative peak heights, or areas, may reflect (i) the differences in affinity of the first and second binding compounds for their respective antigenic determinants, and/or (ii) the presence or absence of the antigenic determinant that the binding compound is specific for. The later situation is important whenever a binding compound is used to monitor the post-translational state of a protein, e.g. phosphorylation state.

Figure 1D:
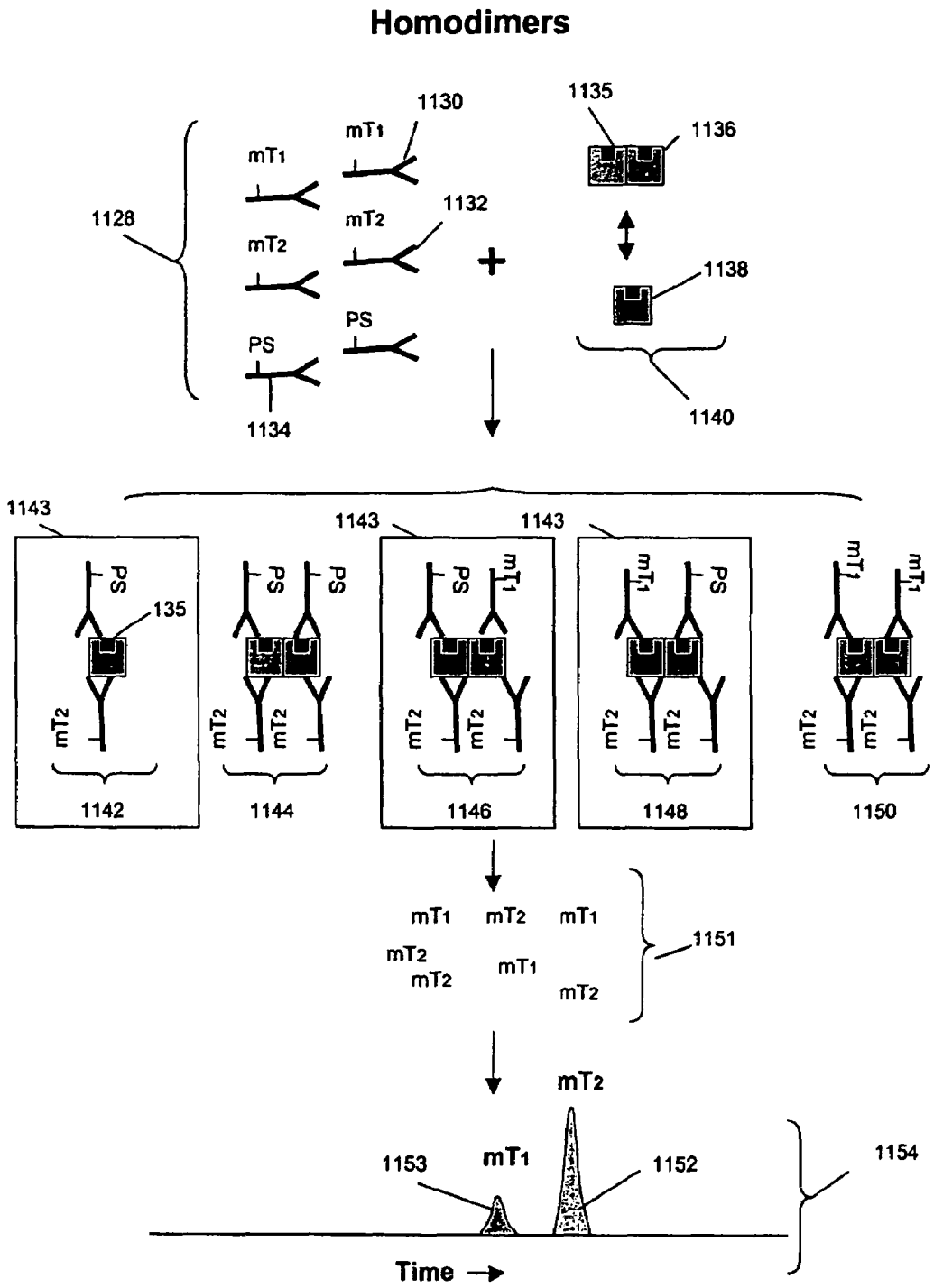
Figure 1E:
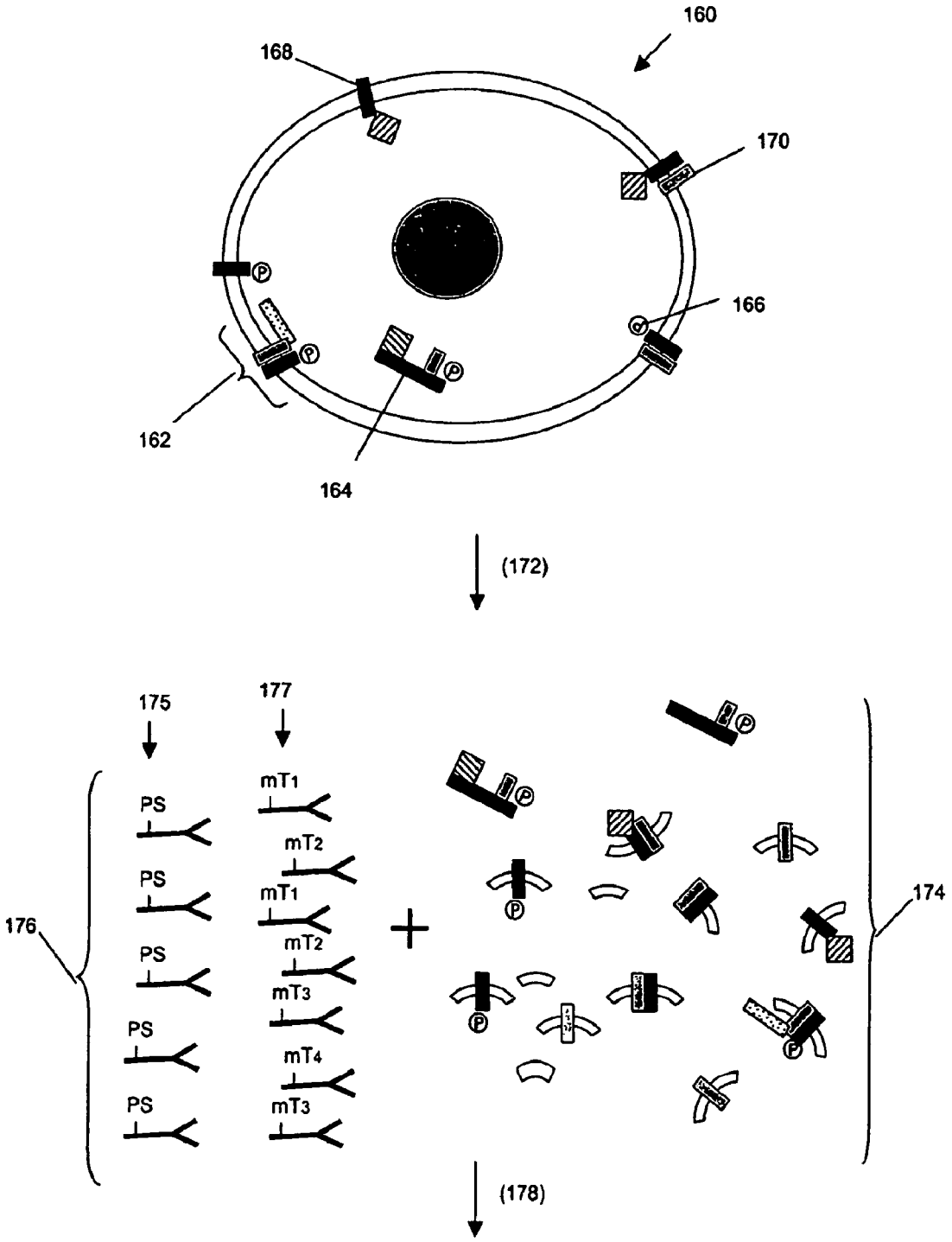

Homodimers may be measured as illustrated in FIG. 1D. As above, an assay may comprise three reagents (1128): cleaving probes (1134), first binding compound (1130), and second binding compound (1132). First binding compound (1130) and cleaving probe (1134) are constructed to be specific for the same antigenic determinant (1135) on protein (1138) that exists (1140) in a sample as either a homodimer (1136) or a monomer (1138). After reagents (1128) are combined with a sample under conditions that promote the formation of stable complexes between the reagents and their respective targets, multiple complexes (1142 through 1150) form in the assay mixture. Because cleaving probe (1134) and binding compound (1130) are specific for the same antigenic determinant (1135), four different combinations (1144 through 1150) of reagents may form complexes with homodimers. Of the complexes in the assay mixture, only those (1143) with both a cleaving probe (1134) and at least one binding compound will contribute released molecular tags (1151) for separation and detection (1154). In this embodiment, the size of peak (1153) is proportional to the amount of homodimer in the assay mixture, while the size of peak (1152) is proportional to the total amount of protein (1138) in the assay mixture, both in monomeric form (1142) or in homodimeric form (1146 and 1148). FIG. 1E illustrates the analogous measurements for cell surface receptors that form heterodimers in cell surface membrane (1161). One skilled in the art would understand that dimers may be measured in either lysates of cells or tissues, or in fixed samples whose membranes have been permeabilized or removed by the fixing process. In such cases, binding compounds may be specific for either extracellular or intracellular domains of cell surface membrane receptors.

Figure 1F:
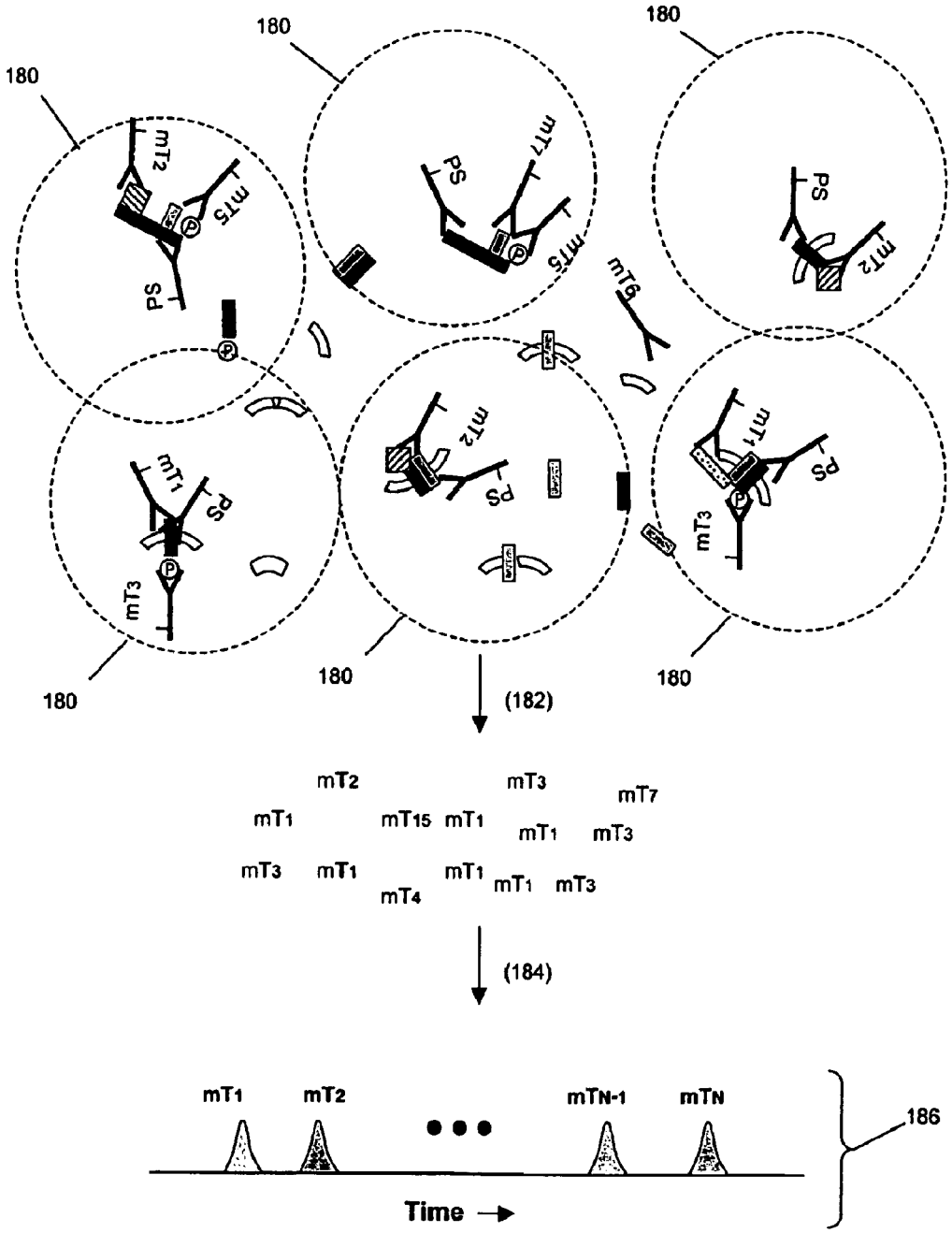

As illustrated in FIGS. 1E and 1F, releasable molecular tags may also be used for the simultaneous detection or measurement of multiple dimers and intracellular complexes in a cellular sample. Cells (160), which may be from a sample from in vitro cultures or from a specimen of patient tissue, are lysed (172) to render accessable molecular complexes associated with the cell membrane, and/or post-translational modification sites, such as phosphorylation sites, within the cytoplasmic domains of the membrane molecules. After lysing, the resulting lysate (174) is combined with assay reagents (176) that include multiple cleaving probes (175) and multiple binding compounds (177). Assay conditions are selected (178) that allow reagents (176) to specifically bind to their respective targets, so that upon activation cleavable linkages within the effective proximity (180) of the cleavage-inducing moieties are cleaved and molecular tags are released (182). As above, after cleavage, the released molecular tags are separated (184) and identified in a separation profile (186), such as an electropherogram, and based on the number and quantities of molecular tags measured, a profile is obtained of the selected molecular complexes in the cells of the sample.

Figure 1G:
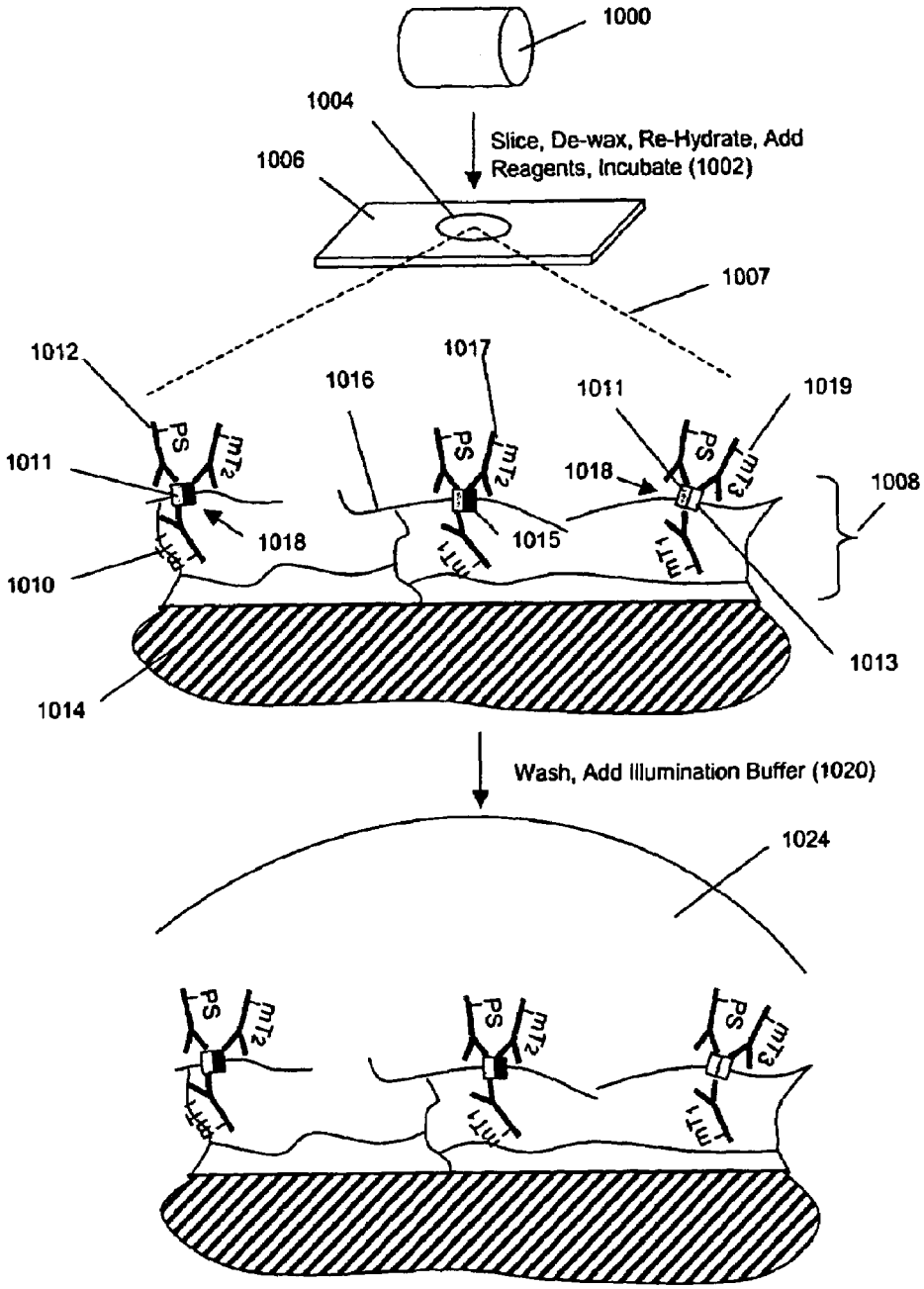
FIGS. 1G-1H illustrate diagrammatically the use of releasable molecular tags to measure cell surface receptor complexes in fixed tissue specimens.
Figure 1H:
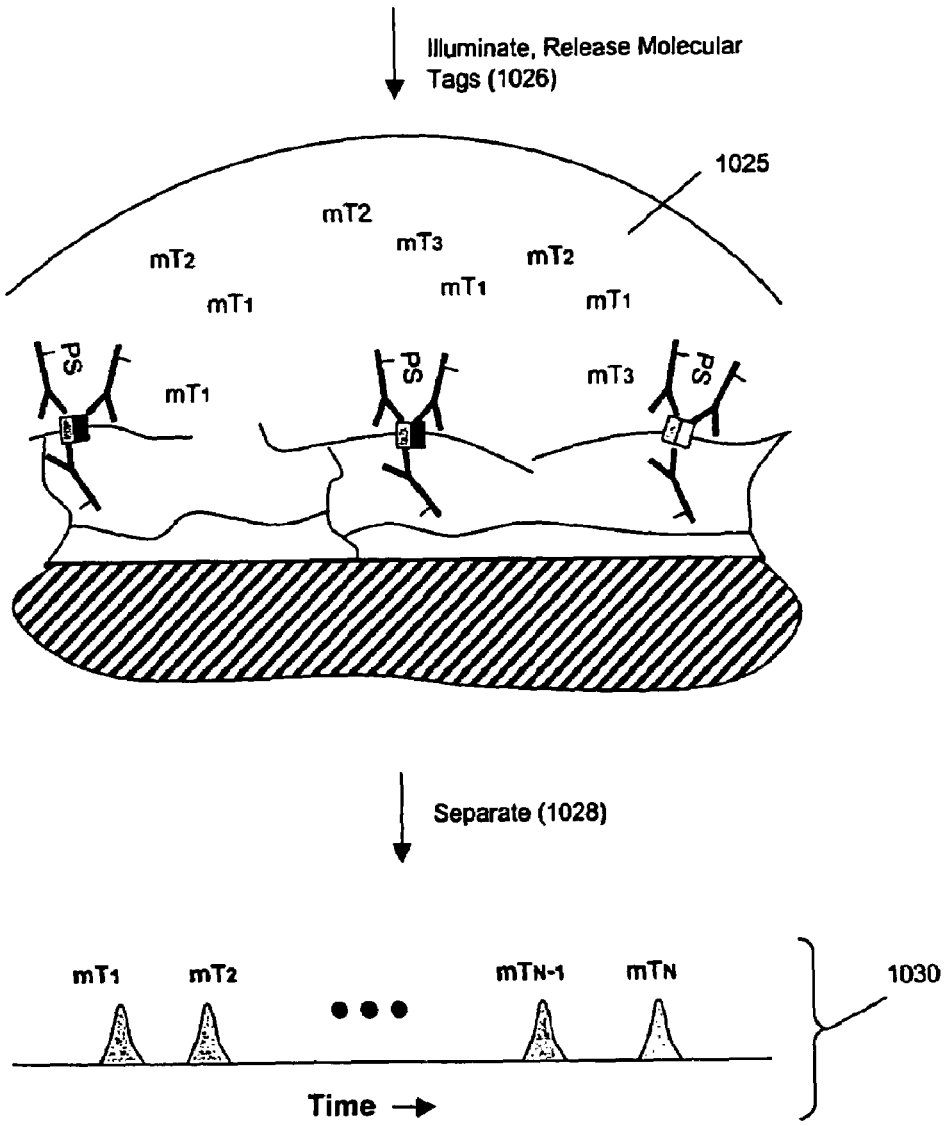

FIGS. 1G and 1H illustrate an embodiment of the invention for measuring receptor complexes in fixed or frozen tissue samples. Fixed tissue sample (1000), e.g. a formalin-fixed paraffin-embedded sample, is sliced to provide a section (1004) using a microtome, or like instrument, which after placing on surface (1006), which may be a microscope slide, it is de-waxed and re-hydrated for application of assay reagents. Enlargement (1007) shows portion (1008) of section (1004) on portion (1014) of microscope slide (1006). Receptor dimer molecules (1018) are illustrated as embedded in the remnants of membrane structure (1016) of the fixed sample. In accordance with this aspect of the invention, cleaving probe and binding compounds are incubated with the fixed sample so that they bind to their target molecules. For example, cleaving probes (1012) (illustrated in the figure as an antibody having a photosensitizer ("PS") attached) and first binding compound (1010) (illustrated as an antibody having molecular tag "$mT_1$" attached) specifically bind to receptor (1011) common to all of the dimers shown, second binding compound (1017)(with "$mT_2$") specifically binds to receptor (1015), and third binding compound (1019)(with "$mT_3$") specifically binds to receptor (1013). After washing to remove binding compounds and cleaving probe that are not specifically bound to their respective target molecules, buffer (1024) (referred to as "illumination buffer" in the figure) is added. For convenience, buffer (1024) may be contained on section (1004), or a portion thereof, by creating a hydrophobic barrier on slide (1006), e.g. with a wax pen. After illumination of photosensitizers and release of molecular tags (1026), buffer (1024) now containing release molecular tags (1025) is transferred to a separation device, such as a capillary electrophoresis instrument, for separation (1028) and identification of the released molecular tags in, for example, electropherogram (1030).

Measurements made directly on tissue samples, particularly as illustrated in FIGS. 1G and 1H, may be normalized by including measurements on cellular or tissue targets that are representative of the total cell number in the sample and/or the numbers of particular subtypes of cells in the sample. Such tissue targets are referred to herein as "tissue indicators." The additional measurement may be preferred, or even necessary, because of the cellular and tissue heterogeneity in patient samples, particularly tumor samples, which may comprise substantial fractions of normal cells. For example, in FIG. 1H, values for the total amount of receptor (1011) may be given as a ratio of the following two measurements: area of peak (1032) of molecular tag ("$mT_1$") and the area of a peak corresponding to a molecular tag correlated with a cellular or tissue component common to all the cells in the sample, e.g. tubulin, or the like. In some cases, where all the cells in the sample are epithelial cells, cytokeratin may be used. Accordingly, detection methods based on releasable molecular tags may include an additional step of providing a binding compound (with a distinct molecular tag) specific for a normalization protein, such as tubulin.

Figure 2A:
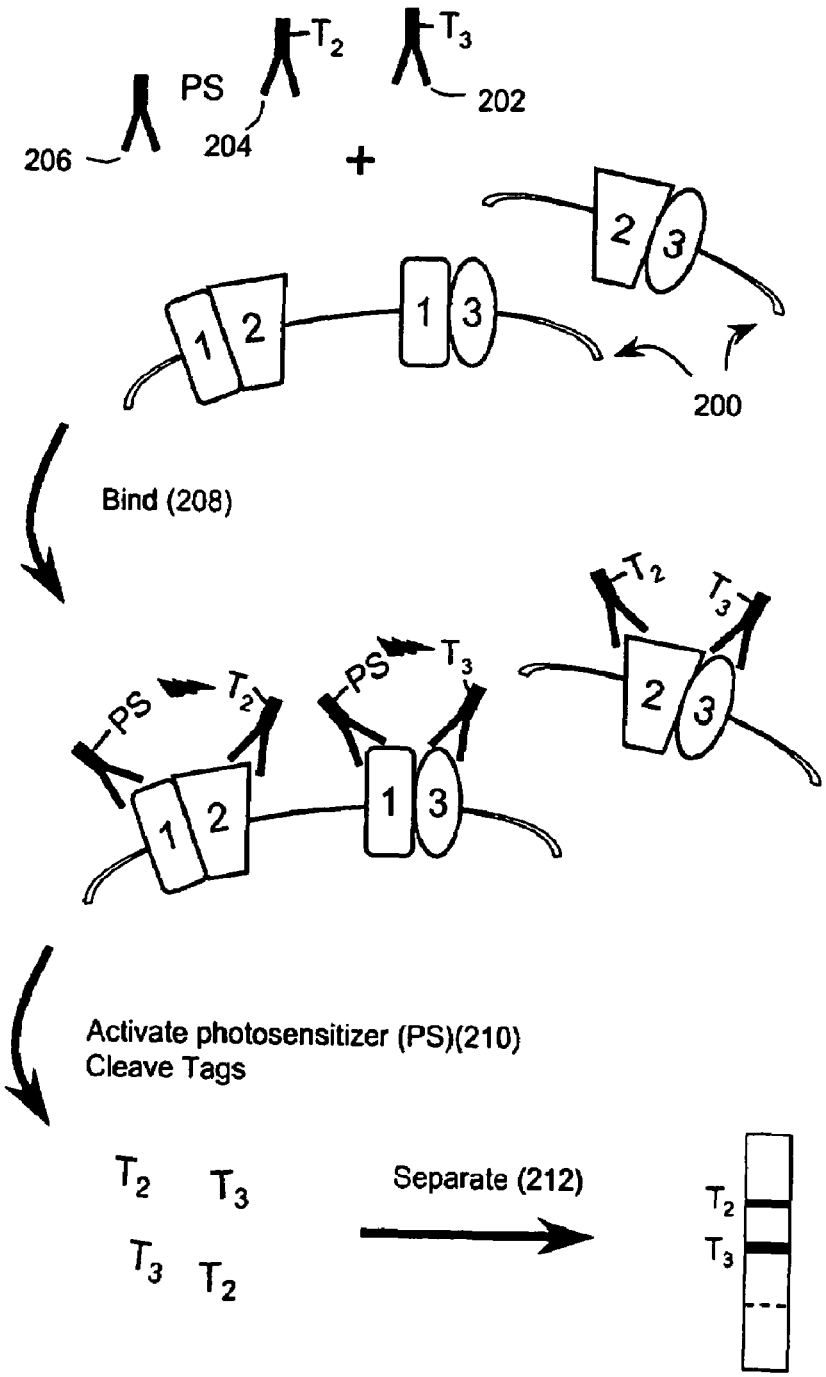
FIGS. 2A-2F illustrate diagrammatically an embodiment of the method of the invention for profiling relative amounts of dimers of a plurality of receptor types.

FIGS. 2A-2F illustrate another embodiment of the invention for profiling dimerization among a plurality of receptor types. FIG. 2A outlines the basic steps of such an assay. Cell membranes (200) that are to be tested for dimers of cell surface receptors are combined with sets of binding compounds (202) and (204) and cleaving probe (206). Membrane fractions (200) contain three different types of monomer receptor molecules ("1," "2," and "3") in its cell membrane which associate to form three different heterodimers: 1-2, 1-3, and 2-3. Three antibody reagents (202) and (204) are combined with membrane fraction (200), each of the antibody reagents having binding specificity for one of the three receptor molecules, where antibody (206) is specific for receptor molecule 1, antibody (204) is specific for receptor molecule 2, and antibody (202) is specific for receptor molecule 3. The antibody for the first receptor molecule is covalently coupled to a photo sensitizer molecule, labeled PS. The antibodies for the second and third receptor molecules are linked to two different tags, labeled $T_2$ and $T_3$, respectively, through a linkage that is cleavable by an active species generated by the photosensitizer moiety.

After mixing, the antibodies are allowed to bind (208) to molecules on the surface of the membranes. The photosensitizer is activated (210), cleaving the linkage between tags and antibodies that are within an actionable distance from a sensitizer molecule, thereby releasing tags into the assay medium. Material from the reaction is then separated (212), e.g., by capillary electrophoresis, as illustrated. As shown at the bottom of FIG. 2A, the tags $T_2$ and $T_3$ are released, and separation by electrophoresis will reveal two bands corresponding to these tags. Because the tags are designed to have a known electrophoretic mobility, each of the bands can be uniquely assigned to one of the tags used in the assay.

Figures 2B, 2C:
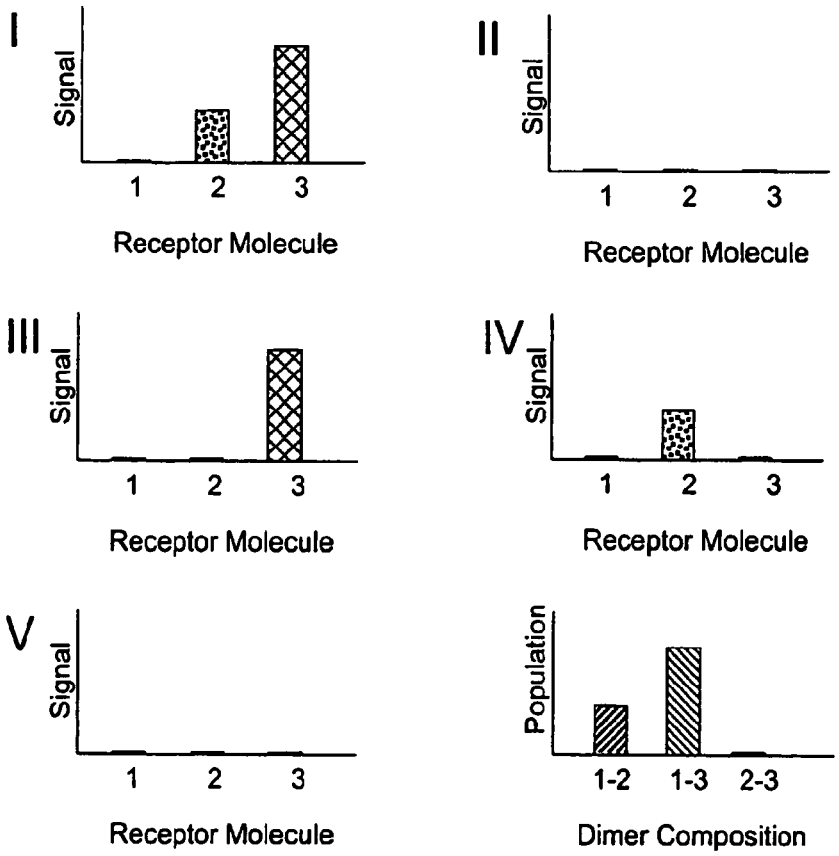

As shown in FIG. 2A, only two of the three different heterodimers that are present in the cell membrane will bind both a photo sensitizer-containing antibody and a tag-containing antibody, and thus only these two species should give rise to released tags. However, multiple experiments are required to measure the relative amounts of the different dimers. FIG. 2B provides a table listing five different assay combinations. In FIG. 2C are the illustrative results for each assay composition. Assay I represents the results from the complete assay, as described in FIG. 2A. In Assay II, the antibody specific for receptor molecule 1, which is linked to the photo sensitizer, is omitted. This assay yields no signal, indicating that the $T_2$ and $T_3$ signals obtained in Assay I require the photosensitizer reagent. Similarly, Assay V shows that the tag signals require the presence of the membranes. Assays III and IV show that each tagged reagent does not require the presence of the other to be cleaved. These results, when considered together, allow one to draw conclusions regarding the presence and composition of receptor heterodimers present in the membrane, as given in FIG. 2C, i.e., that both the 1-2 and the 1-3 heterodimer are present. Furthermore, the relative signal intensities from each tag allow one to estimate the relative abundance of each of the heterodimers.

Figure 2D:
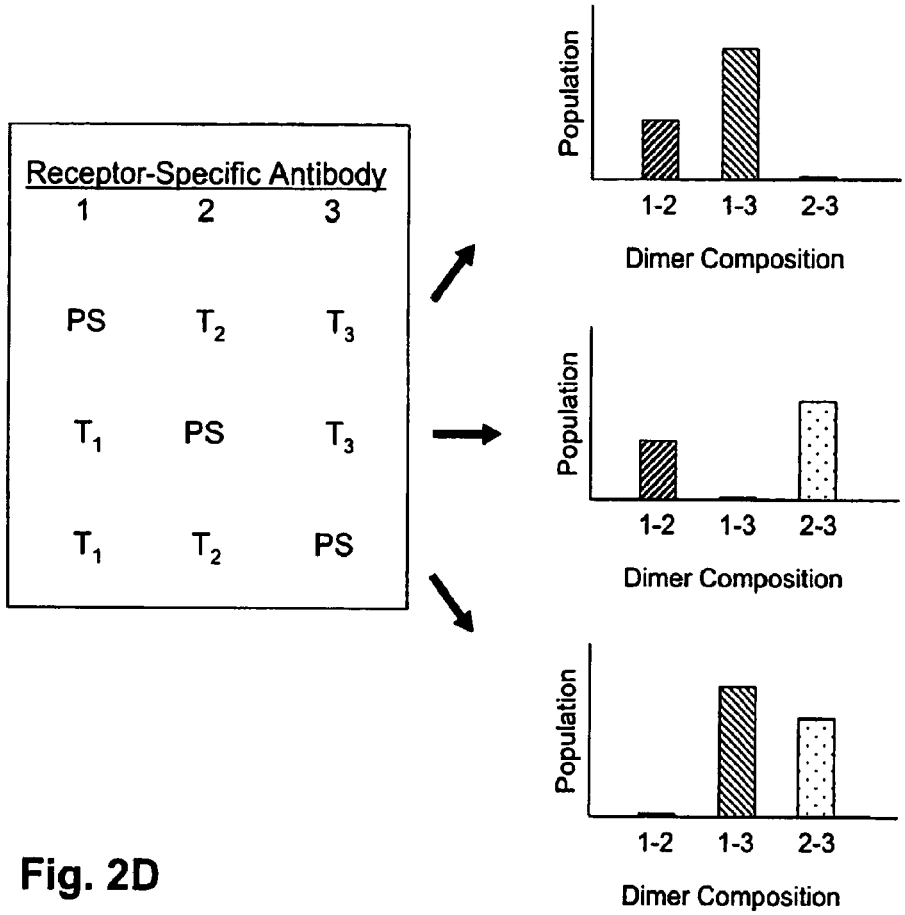
Figure 2E:
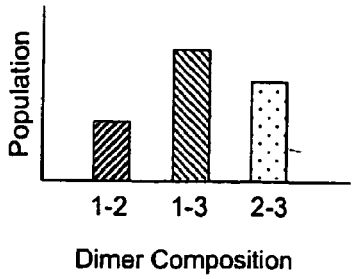

A conclusion regarding existence of the 2-3 heterodimer cannot be made with the combination of reagents used in this assay, however. No signal representing this complex will be obtained, whether or not the complex is present, because it will not have a photosensitizer reagent bound to it. In order to draw conclusions regarding every possible dimeric combination of the three monomers, either a fourth reagent must be used that can be localized to every possible oligomer comprising monomers 1, 2, and/or 3, or the three binding agents used in this experiment must be coupled in different combinations to tags and sensitizer molecules. The later strategy is illustrated in FIGS. 2D and 2E. Three possible combinations of photosensitizer and tag distribution among the three antibody reagents are listed in the table on the left of FIG. 2D. The first combination comprises a photosensitizer coupled to the antibody specific for monomer number 1, and is the same combination used in the illustration of FIGS. 2A-2C, and has the same dimer population as in FIG. 2C. The second combination comprises a photosensitizer coupled to the antibody specific for monomer number 2, and the population profile yields the same number for heterodimer 1-2, plus a value for heterodimer 2-3. The third combination comprises a photosensitizer coupled to the antibody specific for monomer number 3, and the population profile yields the same number for heterodimer 1-3 and 2-3 as obtained from the first two combinations. These results can be combined to yield the overall heterodimer population profile given in FIG. 2E.

Figure 2F:
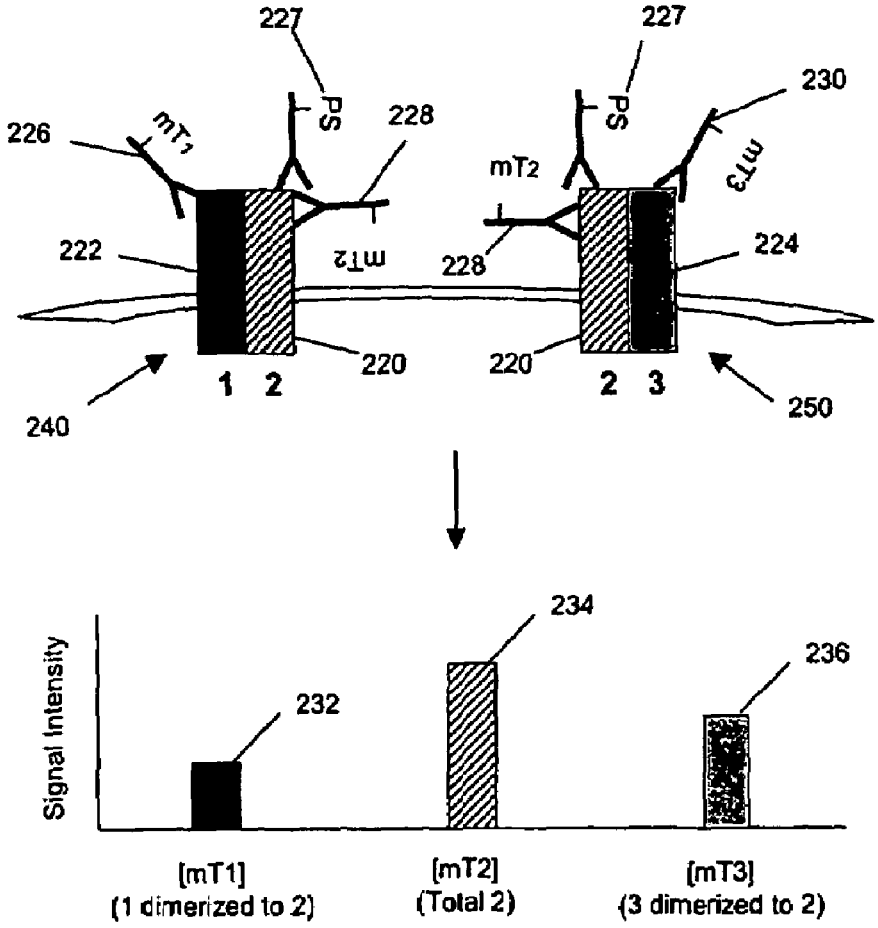

A preferred embodiment for measuring relative amounts of receptor dimers containing a common component receptor is illustrated in FIG. 2F. In this assay design, two different receptor dimers ("1-2" (240) and "2-3" (250)) each having a common component, "2," may be measured ratiometrically with respect to the common component. An assay design is shown for measuring receptor heterodimer (240) comprising receptor "1" (222) and receptor "2" (220) and receptor heterodimer (250) comprising receptor "2" (220) and receptor "3" (224). A key feature of this embodiment is that cleaving probe (227) be made specific for the common receptor of the pair of heterodimers. Binding compound (228) specific for receptor "2" provides a signal (234) related to the total amount of receptor "2" in the assay, whereas binding compound (226) specific for receptor "1" and binding compound (230) specific for receptor "3" provide signals (232 and 236, respectively) related only to the amount of receptor "1" and receptor "3" present as heterodimers with receptor "2," respectively. The design of FIG. 2F may be generalized to more than two receptor complexes that contain a common component by simply adding binding compounds specific for the components of the additional complexes.

A. Binding Compounds

As mentioned above, mixtures containing pluralities of different binding compounds may be provided, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins. In one aspect, a binding compound, which can be represented by the formula below, comprises one or more molecular tags attached to a binding moiety.

$$B\text{-}(L\text{-}E)_k$$

wherein B is binding moiety; L is a cleavable linkage; and E is a molecular tag. In homogeneous assays, cleavable linkage, L, may be an oxidation-labile linkage, and more preferably, it is a linkage that may be cleaved by singlet oxygen. The moiety "$\text{-}(L\text{-}E)_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition that specifically binds to a target, such as a predetermined antigenic determinant of a target protein, such as a cell surface receptor. Such compositions are readily formed from a wide variety of commercially available antibodies, either monoclonal and polyclonal, specific for proteins of interest. In particular, antibodies specific for epidermal growth factor receptors are disclosed in the following patents, which are incorporated by references: U.S. Pat. Nos. 5,677,171; 5,772,997; 5,968,511; 5,480,968; 5,811,098. U.S. Pat. No. 6,488,390, incorporated herein by reference, discloses antibodies specific for a G-protein coupled receptor, CCR4. U.S. Pat. No. 5,599,681, incorporated herein by reference, discloses antibodies specific for phosphorylation sites of proteins. Commercial vendors, such as Cell Signaling Technology (Beverly, Mass.), Biosource International (Camarillo, Calif.), and Upstate (Charlottesville, Va.), also provide monoclonal and polyclonal antibodies specific for many receptors.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety," which is discussed more fully below.

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al, U.S. Pat. No. 5,565,324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio)propionate (SPDP), succinimidyloxycarbonyl-α-methyl-α-(2-pyridyldithio)toluene (SMPT), or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol, sodium borohydride, or the like. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST) (available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g. 0.1 N hydroxylamine, pH 8.5, for 3-6 hours at 37° C. Such spacers can be introduced by a homo bifunctional cross-linking agent such as ethylene glycol bis(succinimidylsuccinate)(EGS) available from Pierce (Rockford, Ill.). A base labile linkage can be introduced with a sulfone group. Homobifunctional crosslinking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages include those disclosed in Rothschild et al, U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in Singh et al, U.S. Pat. No. 6,627,400; and U.S. patent publications Singh et al, 2002/0013126; and 2003/0170915, and in Willner et al, U.S. Pat. No. 5,622,929, all of which are incorporated herein by reference.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002-1012 (2002); Giese, Anal. Chem., 2: 165-168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical migration, or retention, times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent. Molecular tags are identified and quantified by analysis of a separation profile, or more specifically, an electropherogram, and such values are correlated with the amounts and kinds of receptor dimers present in a sample. For example, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). Preferably, the presence, absence, and/or amounts of molecular tags are measured by using one or more standards as disclosed by Williams et al, U.S. patent publication 2003/10170734A1, which is incorporated herein by reference.

Pluralities of molecular tags may also be designed for separation by chromatography based on one or more physical characteristics that include but are not limited to molecular weight, shape, solubility, pKa, hydrophobicity, charge, polarity, or the like, e.g. as disclosed in U.S. patent publication 2003/0235832, which is incorporated by reference. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386-392 (2000); Outinen et al, Eur. J. Pharm. Sci., 6: 197-205 (1998); Lewis et al, J. Chromatogr., 592:183-195 and 197-208 (1992); and the like. An exemplary HPLC instrumentation system suitable for use with the present invention is the Agilent 1100 Series HPLC system (Agilent Technologies, Palo Alto, Calif.).

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8$^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816-2822 (1997); Hobb, Jr., U.S. Pat. No. 4,997,928; Khanna et al., U.S. Pat. No. 4,318,846; and the like. Preferably, D is a fluorescein or a fluorescein derivative.

Figure 3A:
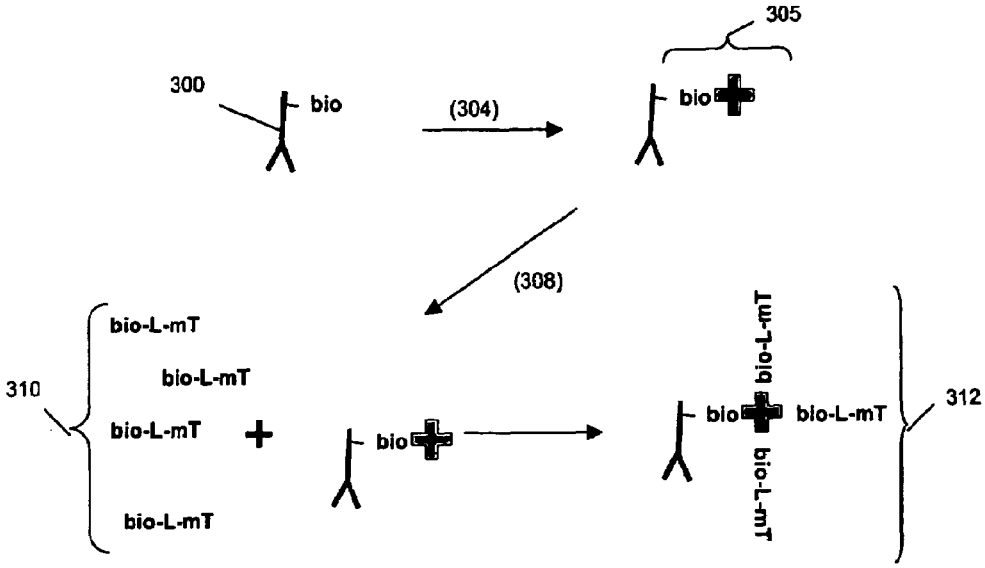
FIGS. 3A-3E illustrate diagrammatically methods for attaching molecular tags to antibodies.

In an embodiment illustrated in FIG. 3A, binding compounds comprise a biotinylated antibody (300) as a binding moiety. Molecular tags are attached to binding moiety (300) by way of avidin or streptavidin bridge (306). Preferably, in operation, binding moiety (300) is first reacted with a target complex, after which avidin or streptavidin is added (304) to form antibody-biotin-avidin complex (305). To such complexes (305) are added (308) biotinylated molecular tags (310) to form binding compound (312).

Figure 3B:
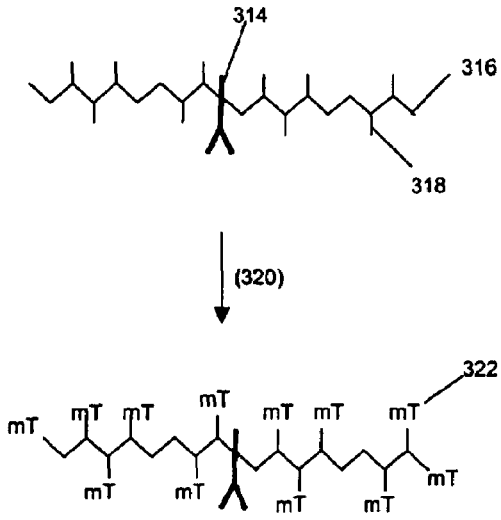

In still another embodiment illustrated in FIG. 3B, binding compounds comprise an antibody (314) derivatized with a multi-functional moiety (316) that contains multiple functional groups (318) that are reacted (320) molecular tag precursors to give a final binding compound having multiple molecular tags (322) attached. Exemplary multi-functional moieties include aminodextran, and like materials.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

B. Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

An important consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one aspect, cleavable linkages preferably are within 1000 nm, and preferably within 20-200 nm, of a bound cleavage-inducing moiety. More preferably, for photosensitizer cleavage-inducing moieties generating singlet oxygen, cleavable linkages are within about 20-100 nm of a photo sensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art recognizes that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J. Biol. Chem. 258: 5991-5993 (1983) (lactoperoxidase); Pierlot et al, Meth. Enzymol., 319: 3-20 (2000) (thermal lysis of endoperoxides); and the like. Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970).

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al, Ann. New York Acad. Sci., 745: 297-320 (1994); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251, 581; McCapra, U.S. Pat. No. 5,516,636; and the like.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photo sensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like. By way of example, a photoactivation device disclosed in Bjornson et al, International patent publication WO 03/051669 is employed. Briefly, the photoactivation device is an array of light emitting diodes (LEDs) mounted in housing that permits the simultaneous illumination of all the wells in a 96-well plate. A suitable LED for use in the present invention is a high power GaAIAs IR emitter, such as model OD-880W manufactured by OPTO DIODE CORP. (Newbury Park, Calif.).

Examples of photosensitizers that may be utilized in the present invention are those that have the above properties and are enumerated in the following references: Singh and Ullman, U.S. Pat. No. 5,536,834; Li et al, U.S. Pat. No. 5,763, 602; Martin et al, Methods Enzymol., 186: 635-645 (1990); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; Thetford, European patent publ. 0484027; Sessler et al, SPIE, 1426: 318-329 (1991); Magda et al, U.S. Pat. No. 5,565,552; Roelant, U.S. Pat. No. 6,001,673; and the like.

As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically.

Figure 3C:
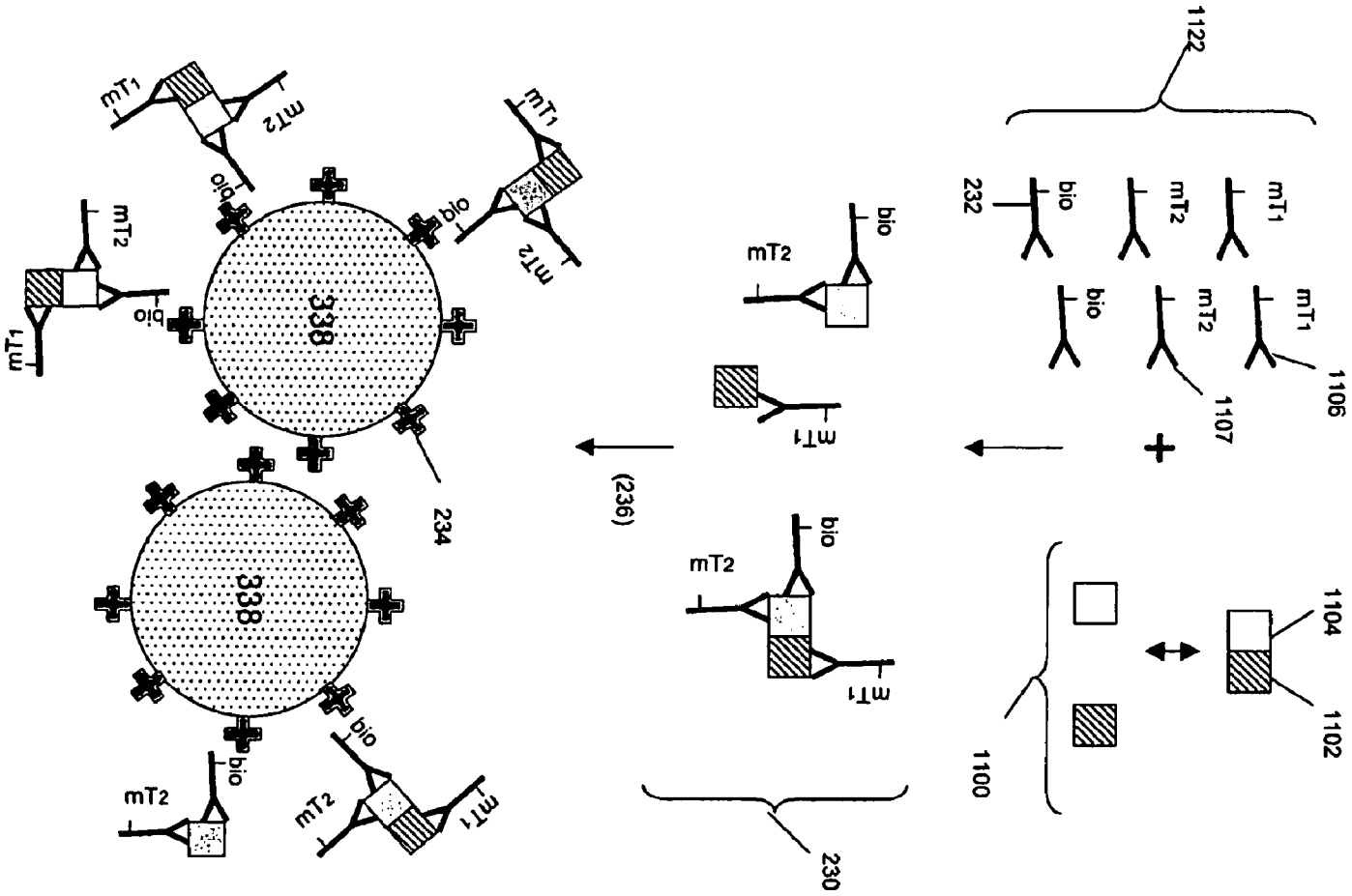
Figure 3D:
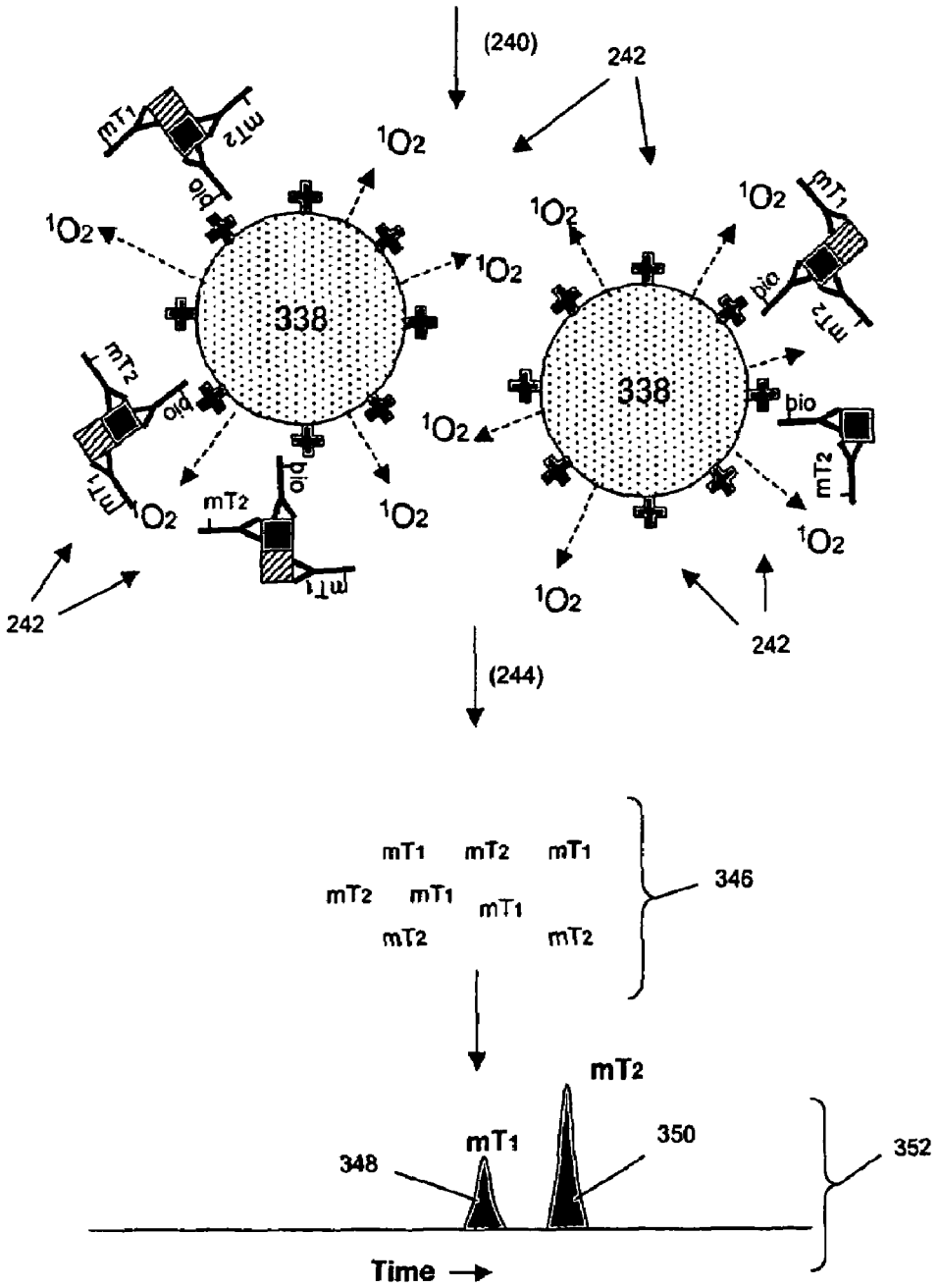

In one embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al, PCT publication WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in J. Amer. Chem. Soc., 97: 3741 (1975). Use of such photosensitizer beads is illustrated in FIG. 3C. As described in FIG. 1C for heteroduplex detection, complexes (330) are formed after combining reagents (1122) with a sample. This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different that the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis. In this embodiment, instead of attaching a photosensitizer directly to a binding compound, such as an antibody, a cleaving probe comprises two components: antibody (332) derivatized with a capture moiety, such as biotin (indicated in FIG. 3C as "bio") and photo sensitizer bead (338) whose surface is derivatized with an agent (334) that specifically binds with the capture moiety, such as avidin or streptavidin. Complexes (330) are then captured (335) by photosensitizer beads by way of the capture moiety, such as biotin (336). Conveniently, if the pore diameter of the filter membrane is selected so that photosensitizer beads (338) cannot pass, then a buffer exchange also serves to remove unbound binding compounds, which leads to an improved signal. After an appropriate buffer for separation has been added, if necessary, photosensitizer beads (338) are illuminated so that singlet oxygen is generated (342) and molecular tags are released (344). Such released molecular tags (346) are then separated to form separation profile (352) and dimers are quantified ratiometrically from peaks (348) and (350). Photosensitizer beads may be used in either homogeneous or heterogeneous assay formats.

Figure 3E:
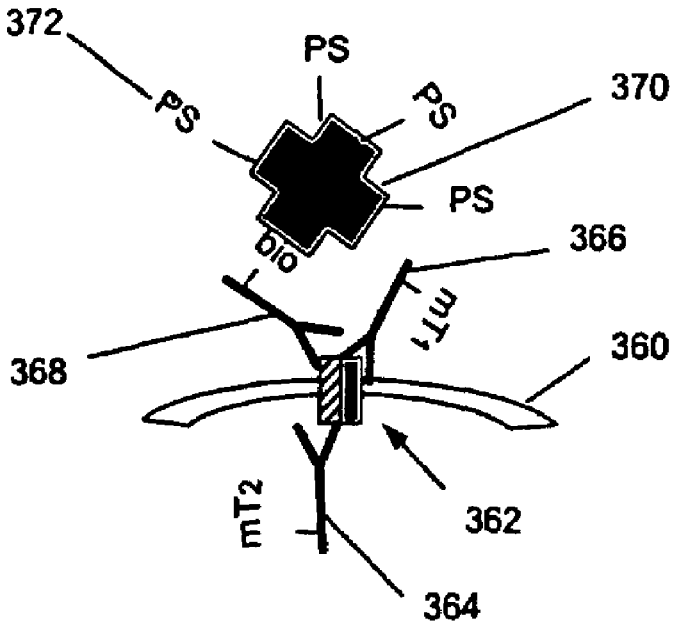

Preferably, when analytes, such as cell surface receptors, are being detected or antigen in a fixed sample, a cleaving probe may comprise a primary haptenated antibody and a secondary anti-hapten binding protein derivatized with multiple photosensitizer molecules. A preferred primary haptenated antibody is a biotinylated antibody, and preferred secondary anti-hapten binding proteins may be either an antibiotin antibody or streptavidin. Other combinations of such primary and secondary reagents are well known in the art, e.g. Haugland, Handbook of Fluorescent Probes and Research Reagents, Ninth Edition (Molecular Probes, Eugene, Oreg., 2002). An exemplary combination of such reagents is illustrated in FIG. 3E. There binding compounds (366 and 368) having releasable tags ("$mT_1$" and "$mT_2$" in the Figure), and primary antibody (368) derivatized with biotin (369) are specifically bound to different epitopes of receptor dimer (362) in membrane (360). Biotin-specific binding protein (370), e.g. streptavidin, is attached to biotin (369) bringing multiple photosensitizers (372) into effective proximity of binding compounds (366 and 368). Biotin-specific binding protein (370) may also be an anti-biotin antibody, and photosensitizers may be attached via free amine group on the protein by conventional coupling chemistries, e.g. Hermanson (cited above). An exemplary photo sensitizer for such use is an NHS ester of methylene blue prepared as disclosed in Shimadzu et al, European patent publication 0510688.

Assay Conditions

The following general discussion of methods and specific conditions and materials are by way of illustration and not limitation. One of ordinary skill in the art will understand how the methods described herein can be adapted to other applications, particularly with using different samples, cell types and target complexes.

In conducting the methods of the invention, a combination of the assay components is made, including the sample being tested, the binding compounds, and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The amount of sample used in an assay will be determined by the predicted number of target complexes present and the means of separation and detection used to monitor the signal of the assay. In general, the amounts of the binding compounds and the cleaving probe are provided in molar excess relative to the expected amount of the target molecules in the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually 25° to 37° C.

After assembly of the assay mixture and incubation to allow the probes to bind to cell surface molecules, the mixture is treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photo sensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g. prior to cleavage of molecular tags, and replaced with another buffer suitable for electrophoretic separation through filtration, aspiration, dilution, or other means.

EXAMPLES

Sources of Materials Used in Examples

Antibodies specific for Her receptors, adaptor molecules, and normalization standards are obtained from commercial vendors, including Labvision, Cell Signaling Technology, and BD Biosciences. All cell lines were purchased from ATCC. All human snap-frozen tissue samples were purchased from either William Bainbridge Genome Foundation (Seattle, Wash.) or Bio Research Support (Boca Raton, Fla.) and were approved by Institutional Research Board (IRB) at the supplier.

The molecular tag-antibody conjugates used below are formed by reacting NHS esters of the molecular tag with a free amine on the indicated antibody using conventional procedures. Molecular tags, identified below by their "Pro_N" designations, are disclosed in the following references: Singh et al, U.S. patent publications, 2003/017915 and 2002/0013126, which are incorporated by reference. Briefly, binding compounds below are molecular tag-monoclonal antibody conjugates formed by reacting an NHS ester of a molecular tag with free amines of the antibodies in a conventional reaction.

Example 1

Analysis of Cell Lysates for Her-2 Heterodimerization and Receptor Phosphorylation In this example, Her1-Her2 and Her2-Her3 heterodimers and phosphorylation states are measured in cell lysates from several cell lines after treatment with various concentrations of epidermal growth factor (EGF) and heregulin (HRG). Measurements are made using three binding compounds and a cleaving probe as described below.

Sample Preparation:

1. Serum-starve breast cancer cell line culture overnight before use.
2. Stimulate cell lines with EGF and/or HRG in culture media for 10 minutes at 37° C. Exemplary doses of EGF/HRG are 0, 0.032, 0.16, 0.8, 4, 20, 100 nM for all cell lines (e.g. MCF-7, T47D, SKBR-3) except BT20 for which the maximal dose is increased to 500 nM because saturation is not achieved with 100 nM EGF.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay:

Assay design: As illustrated diagrammatically in FIG. 4A, Her2-Her3 heterodimers (900) are quantified ratiometrically based on the binding of cleaving probe (902) and binding compounds (904), (906), and (908). A photosensitizer indicated by "PS" is attached to cleaving probe (902) via an avidin-biotin linkage, and binding compounds (904), (906), and (908) are labeled with molecular tags Pro14, Pro10, and Pro11, respectively. Binding compound (904) is specific for a phosphorylation site on Her3.

The total assay volume is 40 ul. The lysate volume is adjusted to 30 ul with lysis buffer. The antibodies are diluted in lysis buffer up to 10 ul. Typically ~5000 to 15000 cell-equivalent of lysates is used per reaction. The detection limit is ~1000 cell-equivalent of lysates.

Procedure: Final concentrations of pre-mixed binding compounds (i.e. molecular tag- or biotin-antibody conjugates) in reaction:

Pro4_anti-Her-2: 0.1 ug/ml
Pro10_anti-Her-1: 0.05-0.1 ug/ml
Pro11_anti-Her-3: 0.1 ug/ml
Pro2_anti-phospho-Tyr: 0.1 ug/ml
Biotin_anti-Her-2: 1-2 ug/ml 1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 600 sec, 30° C.).

Assay Buffers are as Follows:

| Lysis Buffer (made fresh and stored on ice) | | |
|---|---|---|
| Final | ul | Stock |

-continued

| Lysis Buffer (made fresh and stored on ice) | | |
|---|---|---|
| 1% Triton X-100 | 1000 | 10% |
| 20 mM Tris-HCl (ph 7.5) | 200 | 1M |
| 100 mM NaCl | 200 | 5M |
| 50 mM NaF | 500 | 1M |
| 50 mM Na beta-glycerophosphate | 1000 | 0.5M |
| 1 mM $Na_3VO_4$ | 100 | 0.1M |
| 5 mM EDTA | 100 | 0.5M |
| 10 ug/ml pepstatin | 100 | 1 mg/ml |
| 1 tablet (per 10 ml) | N/A | N/A |
| Roche Complete protease inhibitor (#1836170) | | |
| Water | 6500 | N/A |
| | 10 ml Total | |

| Wash buffer (stored at 4° C.) Final | ml | Stock |
|---|---|---|
| 1% NP-40 | 50 | 10% |
| 1xPBS | 50 | 10 x |
| 150 mM NaCl | 15 | 5M |
| 5 mM EDTA | 5 | 0.5M |
| Water | 380 | N/A |
| | 500 ml Total | |

| Illumination buffer: Final | ul | Stock |
|---|---|---|
| 0.005x PBS | 50 | 1 x |
| CE std | 3 | 100 x |
| 10 mM Tris-HCl (pH 8.0) | | 0.1M |
| 10 pM A160 | | 1 mM |
| 10 pM A315 | | 1 mM |
| 10 pM HABA | | 1 mM |
| Water | 10,000 | N/A |
| | 10 ml Total | |

Data Analysis:

1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.
3. Report heterodimerization for Her-1 or Her-3 as the corresponding RFU ratiometric to RFU from Pro4_anti-Her-2 from assay wells using biotin-anti-Her-2.
4. Report receptor phosphorylation for Her-1,2,3 as RFU from Pro2_PT100 anti-phospho-Tyr ratiometric to RFU from Pro4_anti-Her-2 from assay wells using biotin-anti-Her-2.

Figure 4A:
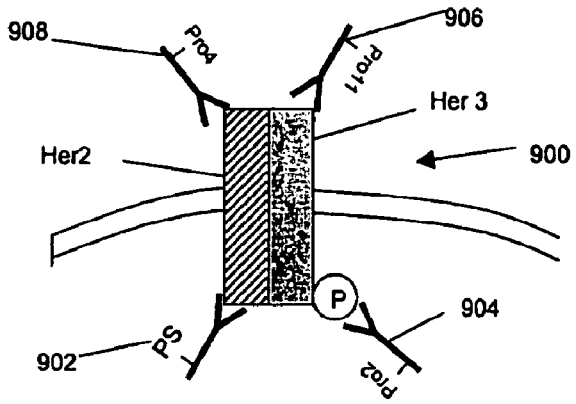
FIGS. 4A-4E illustrate data from assays on SKBR-3 and BT-20 cell lysates for receptor heterodimers using a method of the invention.
Figure 4B:
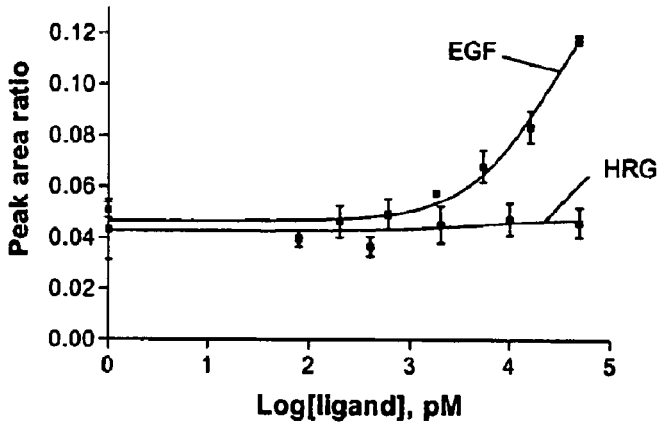
Figure 4C:
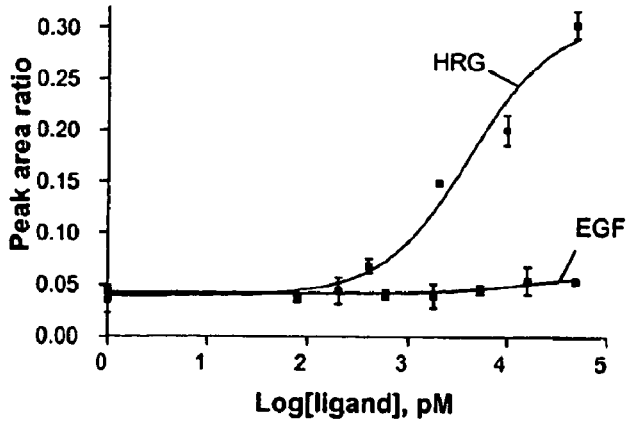
Figure 4D:
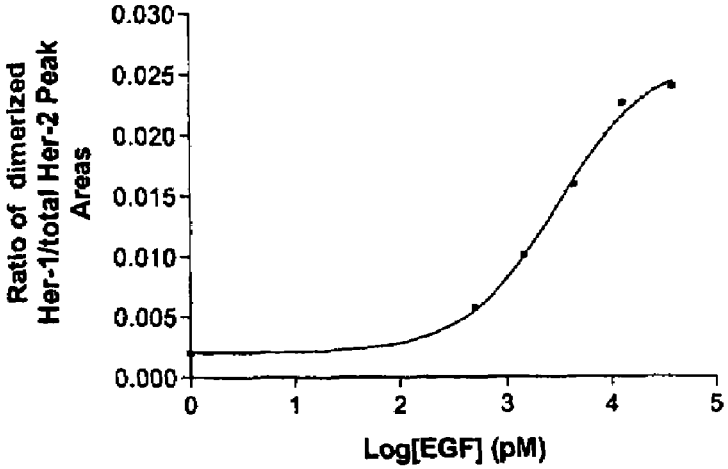
Figure 4E:
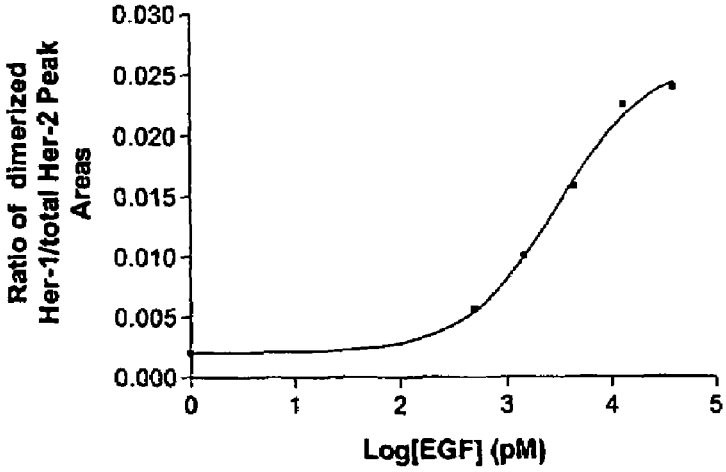

Results of the assays are illustrated in FIGS. 4B-4H. FIG. 4B shows the quantity of Her1-Her2 heterodimers increases on MCF-7 cells with increasing concentrations of EGF, while the quantity of the same dimer show essentially no change with increasing concentrations of HRG. FIG. 4C shows the opposite result for Her2-Her3 heterodimers. That is, the quantity of Her2-Her3 heterodimers increases on MCF-7 cells with increasing concentrations of HRG, while the quantity of the same dimer show essentially no change with increasing concentrations of EGF. FIGS. 4D and 4E show the quantity of Her1-Her2 heterodimers increases on SKBR-3 cells and BT-20 cells, respectively, with increasing concentrations of EGF.

Example 2

Analysis of Tissue Lysates for Her2 Heterodimerization and Receptor Phosphorylation In this example, Her1-Her2 and Her2-Her3 heterodimers and phosphorylation states are measured in tissue lysates from human breast cancer specimens.

Sample Preparation:

1. Snap frozen tissues are mechanically disrupted at the frozen state by cutting.
2. Transfer tissues to microfuge tube and add 3× tissue volumes of lysis buffer (from appendix I) followed by vortexing to disperse tissues in buffer.
3. Incubate on ice for 30 min with intermittent vortexing to mix.
4. Centrifuge at 14,000 rpm, 4° C., for 20 min.
5. Collect supernatants as lysates and determine total protein concentration with BCA assay (Pierce) using a small aliquot.
6. Aliquot the rest for storage at −80° C. until use.

Assay Design:

1. The total assay volume is 40 ul.
2. The lysates are tested in serial titration series of 40, 20, 10, 5, 2.5, 1.25, 0.63, 0.31 ug total-equivalents and the volume is adjusted to 30 ul with lysis buffer. Data from the titration series confirm the specificity of the dimerization or phosphorylation signals.
3. A universal antibody mix comprising all eTag-antibodies diluted in lysis buffer is used at the following concentrations.
4. Individual biotin-antibody for each receptor is added separately to the reactions.
5. Three eTag assays are conducted with each tissue lysate, each using a different biotin-antibody corresponding to specific receptor dimerization to be measured.
6. Expression level of each receptor is determined from different assay containing the biotin-antibody specific to the receptor.
7. Dimerization and phosphorylation signals are determined ratiometrically only in the assay containing the biotin-anti-Her-2.

Assay controls: MCF-10A and MCF-7 cell lines are used as qualitative negative and positive controls, respectively. Cell lines are either unstimulated or stimulated with 100 nM EGF or 100 nM HRG. Lysis buffer is included as a background control when replacing the tissue samples.

Final Concentrations of Pre-Mixed Antibodies in Reactions:

Universal Antibody Mix:

Pro4_anti-Her-2: 0.1 ug/ml
Pro10_anti-Her-1: 0.05 ug/ml
Pro11_anti-Her-3: 0.1 ug/ml
Pro2_anti-phospho-Tyr: 0.01 ug/ml Individual Biotin Antibody:

Biotin_anti-Her-1: 2 ug/ml
Biotin_anti-Her-2: 2 ug/ml
Biotin_anti-Her-3: 2 ug/ml Procedure:

1. Prepare antibody reaction mix by adding antibody to universal antibody mix.
2. To assay 96-well, add 10 ul universal reaction mix to 30 ul lysate and incubate for 1 hour at RT.
3. Add 2 ul streptavidin-derivatized cleaving probe (final 2 ug/well) to assay well and incubate for 45 min.
4. Add 150 ul of PBS with 1% BSA to 96-well filter plate (Millipore MAGVN2250) and incubate for 1 hr at RT for blocking.

5. Empty filter plate by vacuum suction. Transfer assay reactions to filter plate and apply vacuum to empty.
6. Add 200 ul wash buffer and apply vacuum to empty. Repeat one time.
7. Add 200 ul illumination buffer and apply vacuum to empty. Repeat one time.
8. Add 30 ul illumination buffer and illuminate for 20 min.
9. Transfer 10 ul of each reaction to CE assay plate for analysis using ABI3100 capillary electrophoresis instrument with a 22 cm capillary (injection conditions: 5 kV, 75 sec, 30° C.; run conditions: 600 sec, 30° C.)

Data Analysis:

1. Normalize RFU signal of each molecular tag against CE reference standard A315.
2. Determine the cut-off values of RFU (each for dimerization or phosphorylation) below which ratios are not calculated because the signals are too low to be reliable. Below the cut-off values, the RFU signals are not titratable in the series of lysate dilution tested. The values can be determined with a large set of normal tissues where dimerization and phosphorylation signals are expected to be absent or at the lowest. These values also represent the basal level of dimerization or phosphorylation on the normal tissues to which tumor tissues will be compared.
3. For the minority of normal tissues, if present, with RFU values above the cut-off, determine the individual RFU level and ratiometric readouts of Her-1 or Her-3 heterodimerization or phosphorylation peaks detected. These samples represent outliers that should be used as matched donor controls for the corresponding tumor tissue samples while scoring.
4. For all tumor samples showing titratable RFU signals, use the lowest signal of each of Her-1, Her-2, Her-3, or phosphorylation from the tissue lysate titration series as the background. Subtract this background from the molecular tag signals of the high dose lysates (e.g. 40 ug) to yield the specific RFU signals. If there is no signal dose response in the titration series, all signals (which are usually very low) are considered background and no specific signals can be used for ratiometric analysis.
5. Report heterodimerization for Her-1 or Her-3 as the corresponding specific RFU ratiometric to the specific RFU from Pro4_anti-Her-2. If no specific RFU is obtained, the dimerization is negative.
6. Report receptor phosphorylation for Her-1,2,3 as specific RFU from Pro2_anti-phospho-Tyr ratiometric to the specific RFU from Pro4_anti-Her-2. If no specific RFU is obtained, the phosphorylation is negative.

Figure 5A:
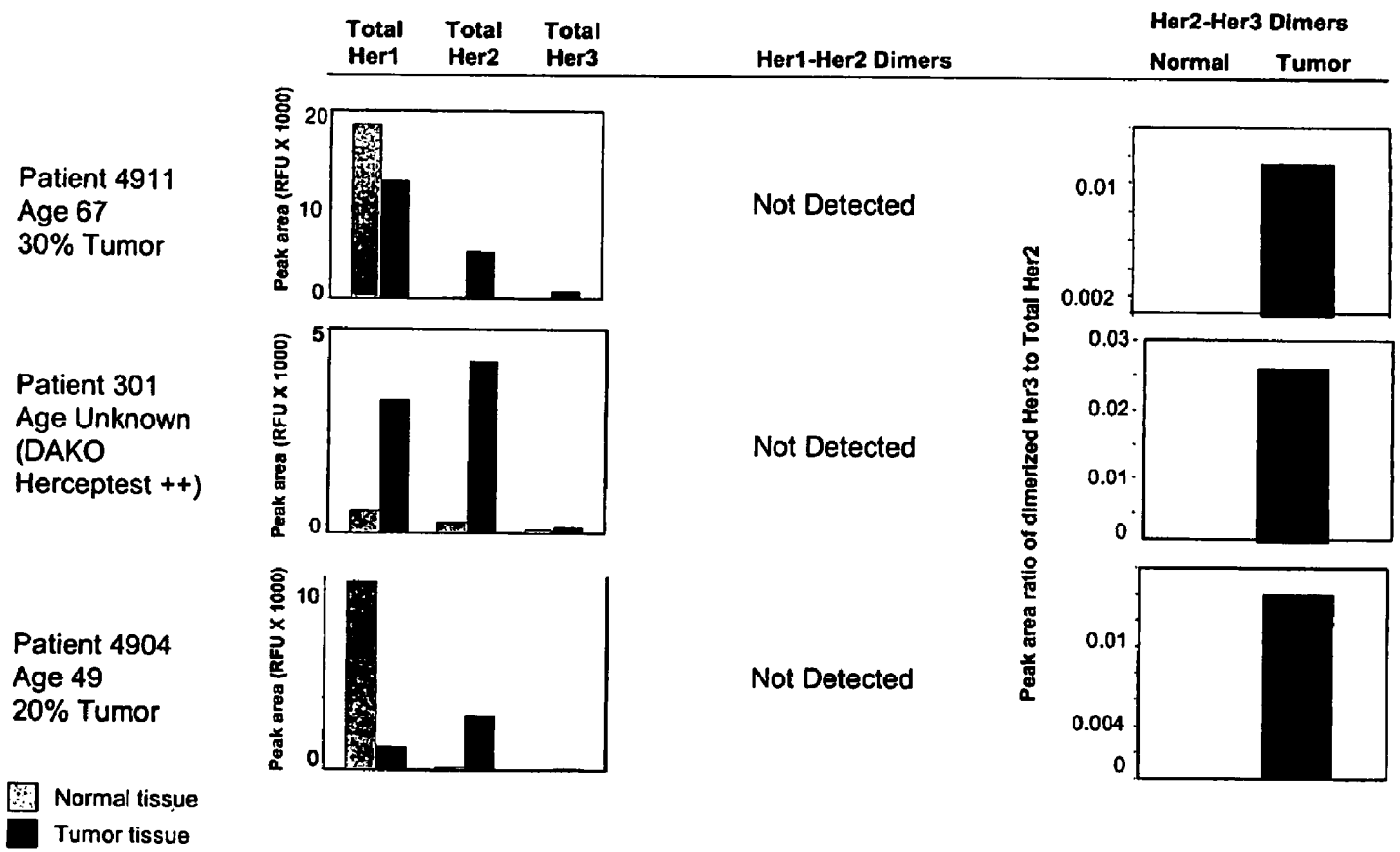
FIGS. 5A-5C illustrate data from assays for receptor heterodimers on human normal and tumor breast tissue samples using a method of the invention.
Figure 5B:
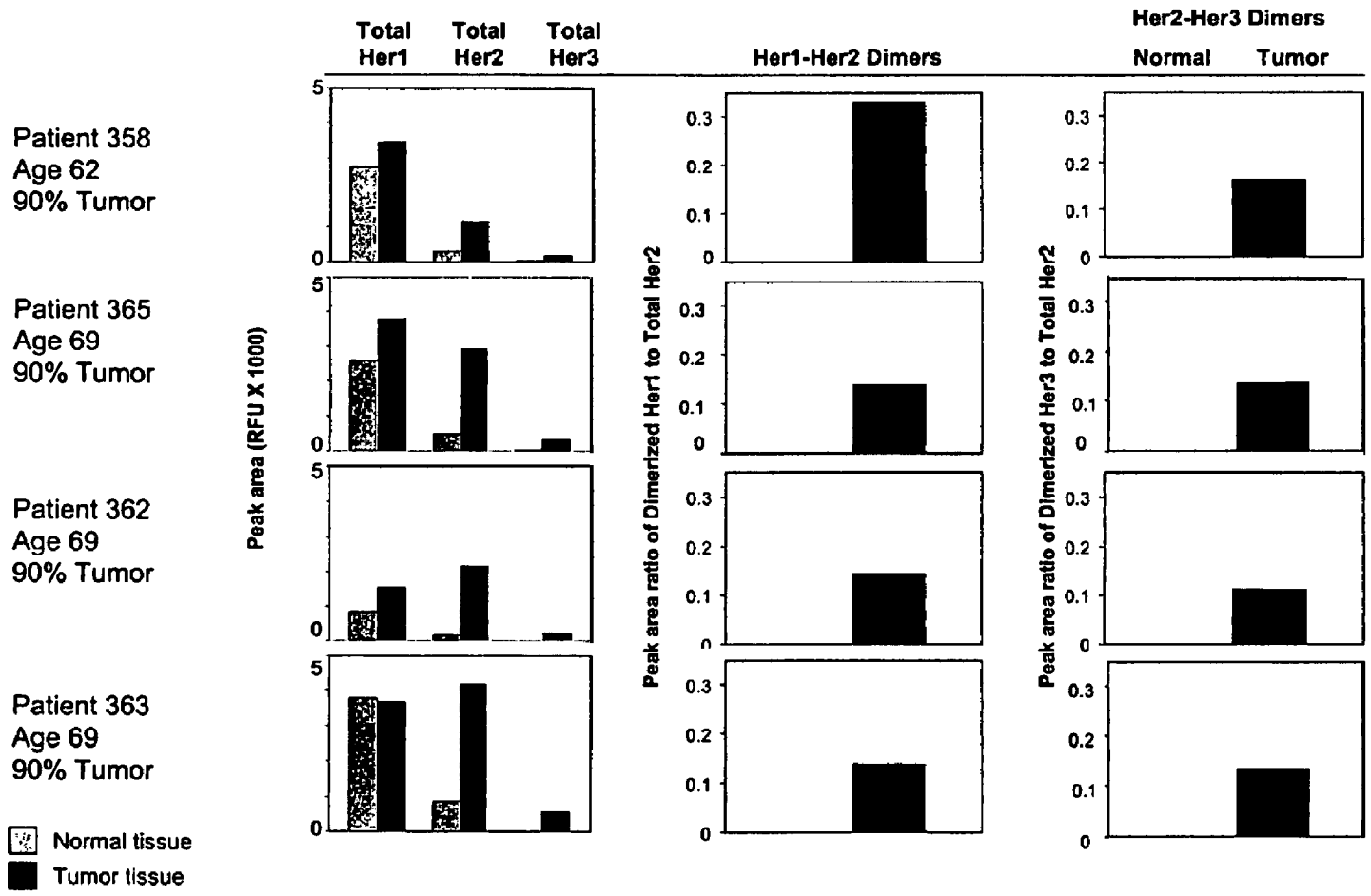
Figure 5C:
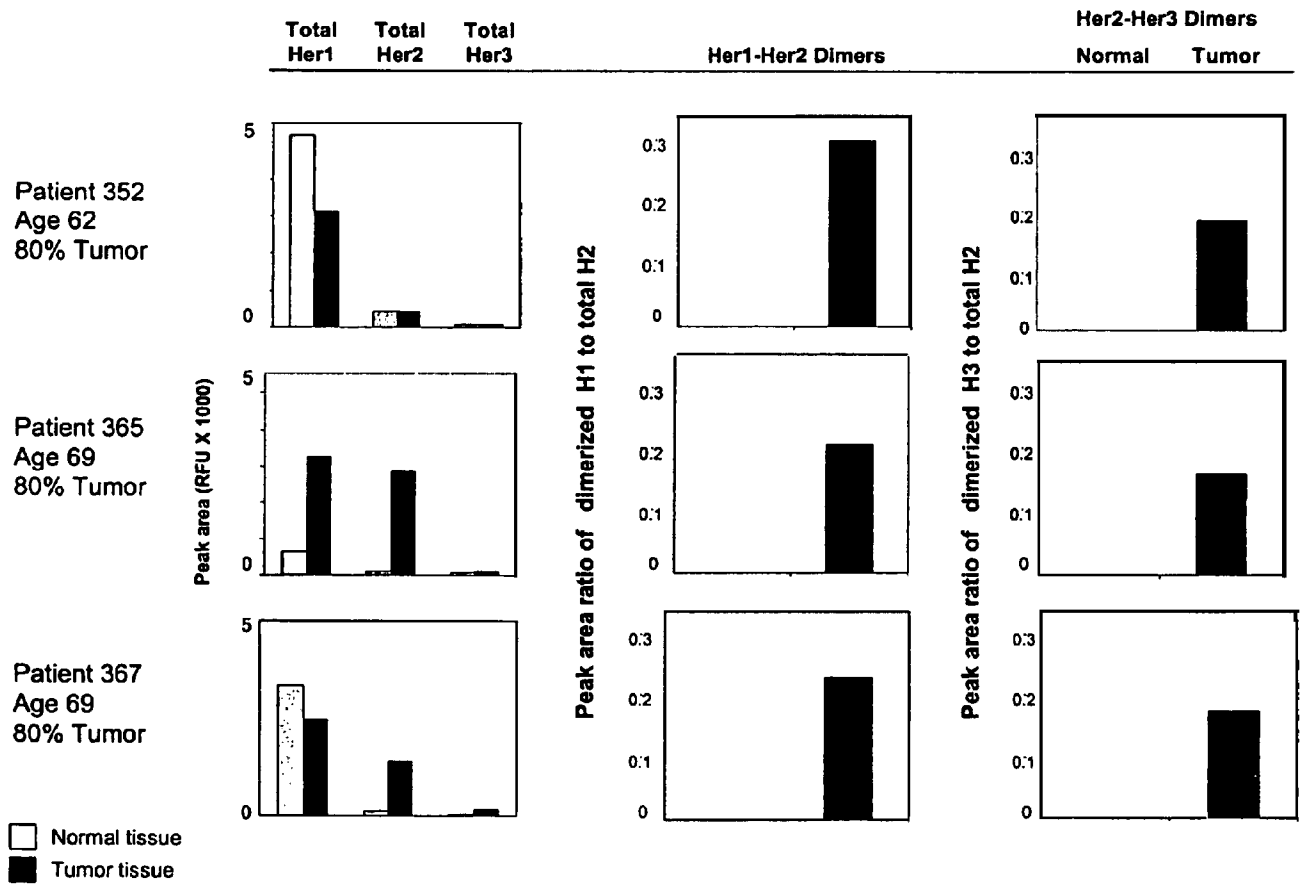

In FIGS. 5A-5C data shown are representative of multiple patients' breast tissue samples tested with assays of the invention. The clinical Her-2 status from immunohistochemistry (DAKO Herceptest) of 9 out of 10 tumor samples was negative, indicative of either undetectable Her-2 staining, or staining of less than 10% of the tumor cells, or a faint and barely perceptible staining on part of the cell membrane of more than 10% tumor cells. The assays of the invention determined the expression of Her-1, Her-2, and Her-3 on both normal and tumor tissues. The heterodimerization of Her1 and Her2 and of Her2 and Her3 was detected only in tumor tissues but not in any normal tissues.

Example 3

Analysis of Cell Lysates for Her1 or Her2 Homodimerization and Receptor Phosphorylation Sample preparation was carried out essentially as described in Example 2. Her1 homodimerization was induced by treating the cell lines with EGF or TGFα. For homodimerization of Her2 which does not have a ligand, unstimulated SKBR-3 or MDA-MD-453 cells that overexpress Her2 are compared to unstimulated MCF-7 cells that express a low level of Her2.

Assay design: A monoclonal antibody specific to the receptor is separately conjugated with either a molecular tag or biotin (that is then linked to a photosensitizer via an avidin bridge), so that the cleaving probe and a binding compound compete to bind to the same epitope in this example. Another binding compound is used that consists of a second antibody recognizing an overlapping epitope on the receptor, so that a ratiometric signal can be generated as a measure of homodimerization. The signal derived from the second antibody also provides a measure of the total amount of receptor in a sample. The total amount of receptor is determined in a separate assay well. Receptor phosphorylation can be quantified with either homodimerization or total receptor amount.

Procedure: The assay volume is 40 ul and the general procedure is similar to that of Example 2. Two assay wells, A and B, are set up for each sample to quantify homodimerization and total amount of receptor separately.

For Quantification of Her1-Her1 Homodimers:

Final Concentrations in Antibody Mix in Assay Well A:
- Pro12_anti-Her-1: 0.05-0.1 ug/ml
- Biotin_anti-Her-1: 1-2 ug/ml Final Concentrations in Antibody Mix in Assay Well B:
- Pro10_anti-Her-1: 0.05-0.1 ug/ml
- Pro2_anti-phospho-Tyr: 0.1 ug/ml
- Biotin_anti-Her-1: 1-2 ug/ml For Quantification of Her2-Her2 Homodimers:

Final Concentrations in Antibody Mix in Assay Well A:
- Pro4_anti-Her-1: 0.05-0.1 ug/ml
- Biotin_anti-Her-1: 1-2 ug/ml Final Concentrations in Antibody Mix in Assay Well B:
- Pro4_anti-Her-1: 0.05-0.1 ug/ml
- Pro2_anti-phospho-Tyr: 0.1 ug/ml
- Biotin_anti-Her-1: 1-2 ug/ml Data Analysis:

1. Normalize RFU signal of each molecular tag against CE reference standard A315.
2. Subtract RFU of "no lysate" background control from corresponding molecular tag signals.
3. Report homodimerization for Her-1 or Her-2 as the corresponding normalized RFU from assay well A as ratiometric to normalized RFU of total receptor amount from the corresponding assay well B.
4. Report receptor phosphorylation for Her-1 or Her-2 homodimer as normalized RFU from Pro2_PT100 anti-phospho-Tyr from assay well B as ratiometric to normalized RFU from total receptor amount from the same assay well B.

Figure 6A:
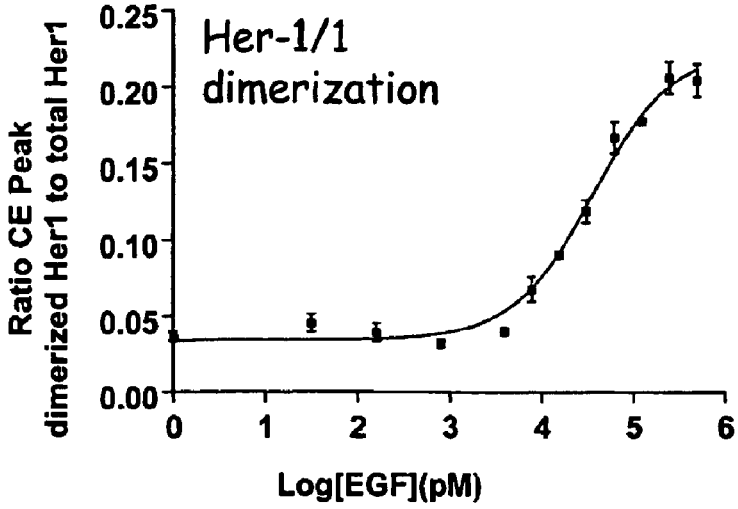
FIGS. 6A and 6B illustrate data from assays of the invention for detecting homodimers and phosphorylation of Her1 in lysates of BT-20 cells.
Figure 6B:
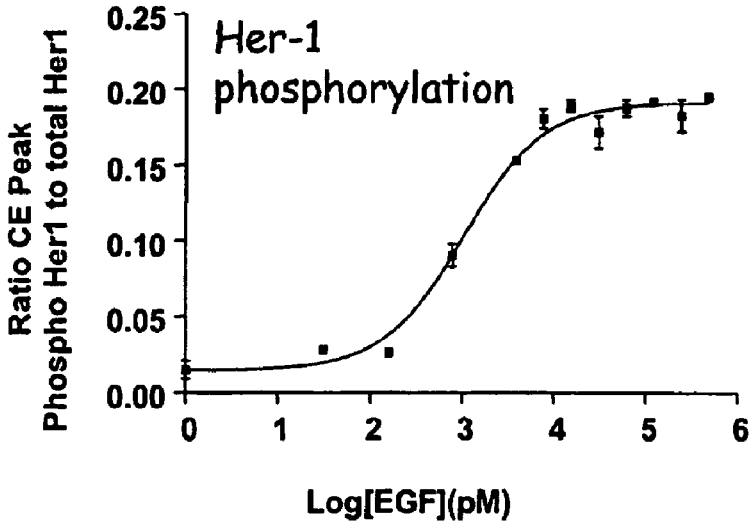
Figure 7:
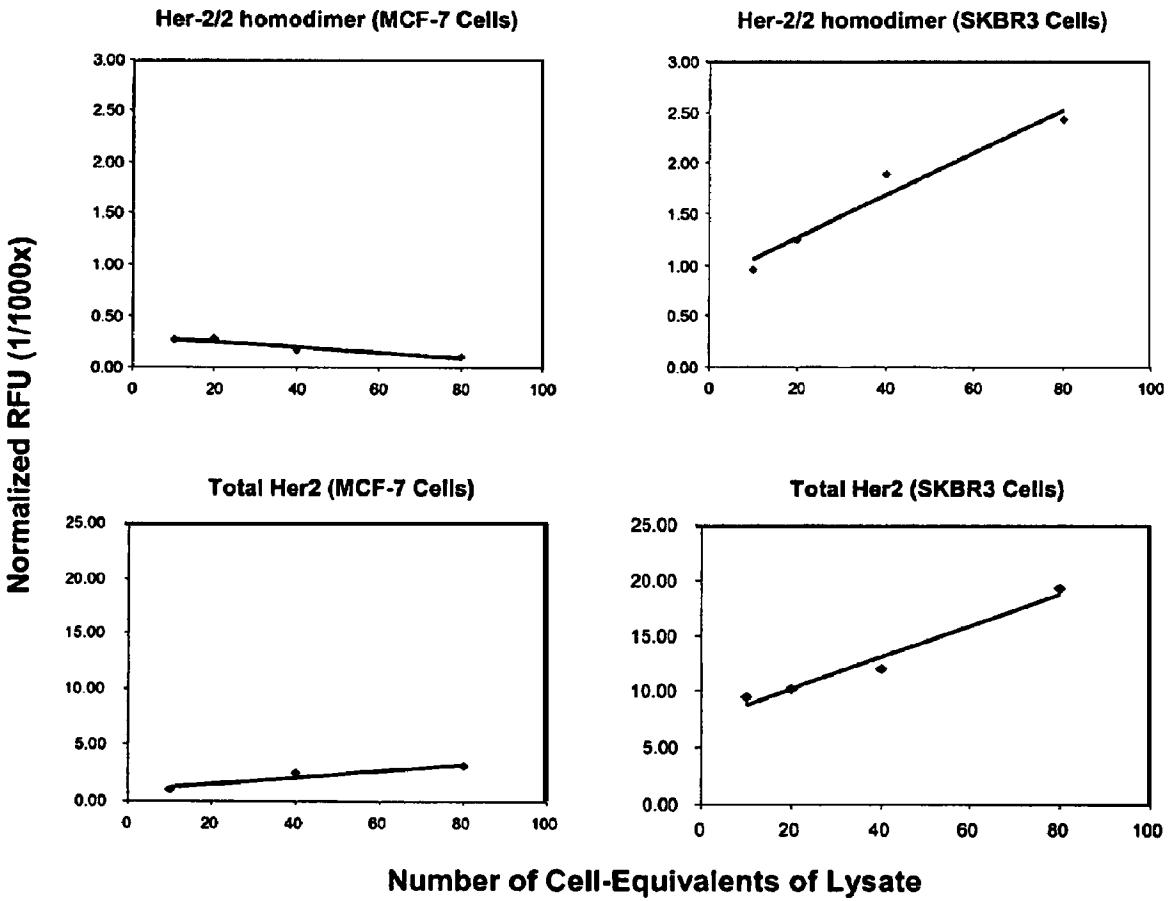
FIG. 7 shows data from assays of the invention that show Her2 homodimer populations on MCF-7 and SKBR-3 cell lines.

Results of the assays are illustrated in FIGS. 6A-6B and FIG. 7. FIG. 6A shows that the quantity of Her1-Her1 homodimers on BT-20 cells increases with increasing concentration of EGF. FIG. 6B shows that the quantity of Her1 phosphorylation in BT-20 cells increases with increasing EGF concentration. The detection of Her2-Her2 homodimers was demonstrated by comparison of signals from SKBR-3 cells expressing Her2 with signals from MCF-7 cells that express reduced level of Her2 on the cell surface. As shown in the charts of FIG. 7, no specific titratable Her2-Her2 homodimer signals were detected with MCF-7 cells whereas Her2-Her2 homodimer signals from SKBR-3 cells were clearly above the signals from MCF-7 cells Example 4

Analysis of Cell Lysates for Her1-Her3 Heterodimerization and Receptor Phosphorylation Samples are Prepared as Follows:

1. Serum-starve breast cancer cell line culture overnight before use.
2. Stimulate cell lines with HRG in culture media for 10 minutes at 37° C. Exemplary doses of HRG are 0, 0.032, 0.16, 0.8, 4, 20, 100 nM for T47D cells.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay design: The total assay volume is 40 ul. The lysate volume is adjusted to 30 ul with lysis buffer. The antibodies are diluted in lysis buffer up to 5 ul. Typically ~5000 to 50000 cell-equivalent of lysates is used per reaction. Final concentrations of pre-mixed antibodies in reaction:

Pro10_anti-Her-1: 0.05-0.1 ug/ml
Pro11_anti-Her-3: 0.1 ug/ml
Pro2_anti-phospho-Tyr: 0.1 ug/ml
Biotin_anti-Her-3: 1-2 ug/ml 1. To assay 96-well, add 5 ul antibody mix to 30 ul lysate and incubate for 1 hour at RT.
2. Add 5 ul streptavidin-derivatized molecular scissor (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using ABI3100 capillary electrophoresis instrument with a 22 cm capillary (injection conditions: 5 kV, 425 sec, 30° C.; run conditions: 600 sec, 30° C.).

Data Analysis:

1. Normalize RFU signal of each eTag reporter against CE reference standard A315.
2. Subtract RFU of "no lysate" background control from corresponding eTag reporter signals.
3. Report heterodimerization as the Her-1 derived Pro10 RFU ratiometric to Pro11 RFU from anti-Her-3.
4. Report receptor phosphorylation for Her-1/3 as RFU from Pro2_PT100 anti-phospho-Tyr ratiometric to RFU from Pro11_anti-Her-3 from assay wells using biotin-anti-Her-3.

Figure 8B:
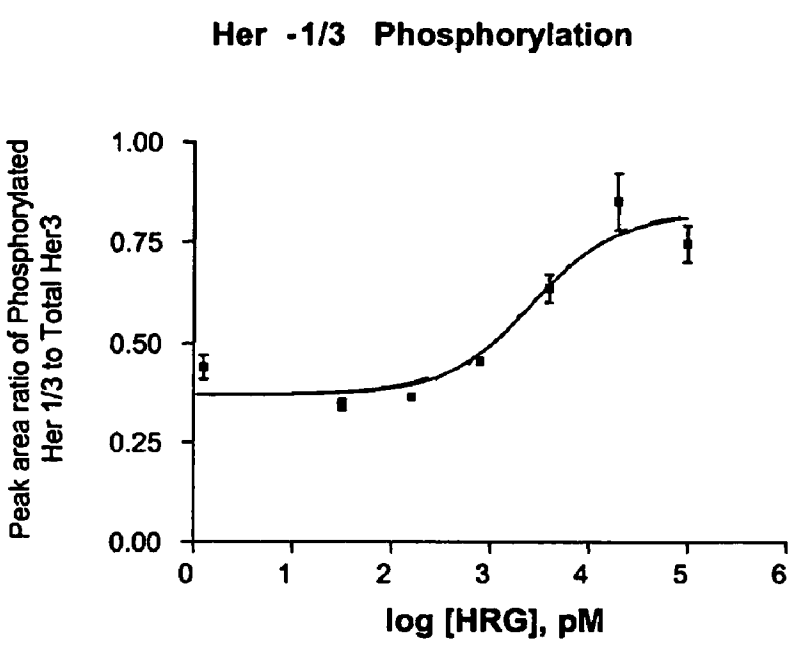
FIGS. 8A-8B show data from assays of the invention that detect heterodimers of Her1 and Her3 on cells in response to increasing concentrations of heregulin (HRG).
Figure 8A:
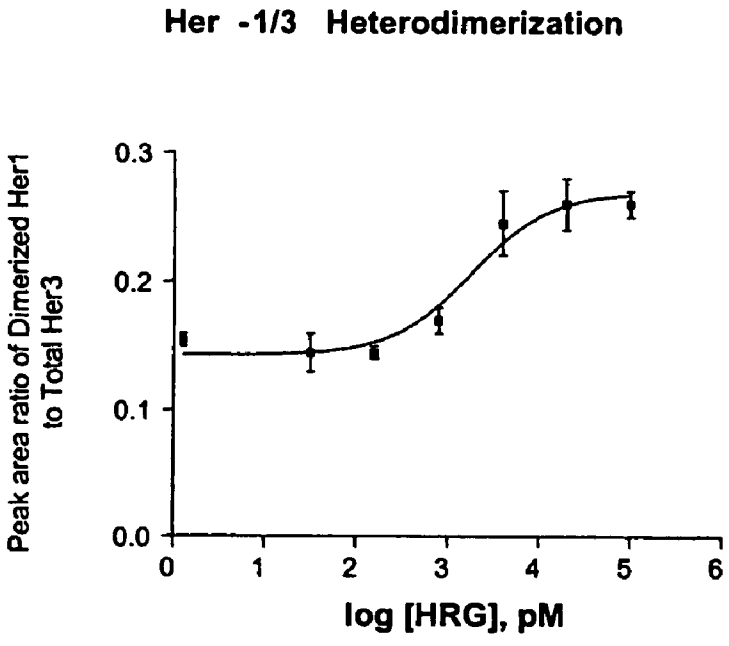

Results of the assay are illustrated in FIGS. 8A and 8B. The data show that both Her1-Her3 heterodimerization and dimer phosphorylation increase with increasing concentrations of HRG.

Example 5

Increase in Her1-Her3 Receptor Dimer Expression in Cancer Cell Lines in Response to Increase in Epidermal Growth Factor In this example, Her1-Her3 heterodimers are measured in cell lysates from cancer cell lines 22Rv1 and A549 after treatment with various concentrations of epidermal growth factor (EGF). Measurements are made using three binding compounds and a cleaving probe as described below.

Sample Preparation:

1. Serum-starve breast cancer cell line culture overnight before use.
2. Stimulate cell lines with EGF in culture media for 10 minutes at 37° C. Exemplary doses of EGF applied to both cell lines varied between 0-100 nM.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.) Determine protein concentration.
5. Collect supernatants as lysates and aliquot for storage at −80° C. until use.

The assay design is essentially the same as illustrated in FIG. 4A, with the following exceptions: binding compounds (904), (906), and (908) are labeled with molecular tags Pro10, Pro11, and Pro 2, respectively. The total assay volume is 40 ul. The lysate volume is adjusted to 30 ul with lysis buffer. The antibodies are diluted in lysis buffer up to 5 ul. Typically ~5000 to 15000 cell-equivalent of lysates is used per reaction. The detection limit is ~1000 cell-equivalent of lysates. Procedure: Final concentrations of pre-mixed binding compounds (i.e. molecular tag- or biotin-antibody conjugates) in reaction:

Pro10_anti-Her-1: 0.05-0.1 ug/ml
Pro11_anti-Her-3: 0.1 ug/ml
Pro2_anti-phospho-Tyr: 0.1 to 0.2 ug/ml
Biotin_anti-Her-3: 1-2 ug/ml 1. To assay 96-well, add 5 ul antibody mix to 30 ul lysate and incubate for 1 hour at RT.
2. Add 5 ul streptavidin-derivatized cleaving probe (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 70 sec, 30° C.; run conditions: 425 sec, 30° C.).

Assay buffers are as follows:
Lysis Buffer (made fresh and stored on ice)

| Final | ul | Stock |
|---|---|---|
| 1% TritonX-100 | 1000 | 10% |
| 20 mM Tris-HCl (ph 7.5) | 500 | 1M |
| 100 mM NaCl | 200 | 5M |
| 50 mM NaF | 500 | 1M |
| 50 mM Na beta-glycerophosphate | 500 | 1.0M |
| 1 mM $Na_3VO_4$ | 100 | 0.1M |
| 5 mM EDTA | 100 | 0.5M |
| 10 ug/ml pepstatin | 100 | 1 mg/ml |
| 1 tablet (per 10 ml) | N/A | N/A |
| Roche Complete protease inhibitor (#1836170) | | |
| Water | 7 ml | N/A |

-continued

| Assay buffers are as follows: Lysis Buffer (made fresh and stored on ice) | | |
|---|---|---|
| Final | ul | Stock |
| | 10 ml Total | |
| Wash buffer (stored at 40 C.): 0.5% Triton X100 in lx PBS. illumination buffer: | | |
| 0.005x PBS | 50 | 1 X |
| CE std 1 (A27, ACLARA Biosciences, Inc. Mountain View, CA) | 4 | 5000 x |
| CE std 2 (fluorescein) | 4 | 5000 x |
| Water | 9942 | N/A |
| | 10 ml Total | |

Data Analysis:

1. Normalize relative fluorescence units (RFU) signal of each molecular tag against CE reference standard 2.
2. Subtract RFU of "no lysate" background control from corresponding molecular tag signals.
3. Report heterodimerization for Her-1 as the corresponding RFU ratiometric to RFU from Pro11_anti-Her-3 from assay wells using biotin-anti-Her-3.
4. Report receptor phosphorylation for Her-1,2,3 as RFU from Pro2_PT100 anti-phospho-Tyr ratiometric to RFU from Pro11_anti-Her-3 from assay wells using biotin-anti-Her-3 (data not shown).

Figure 9A:
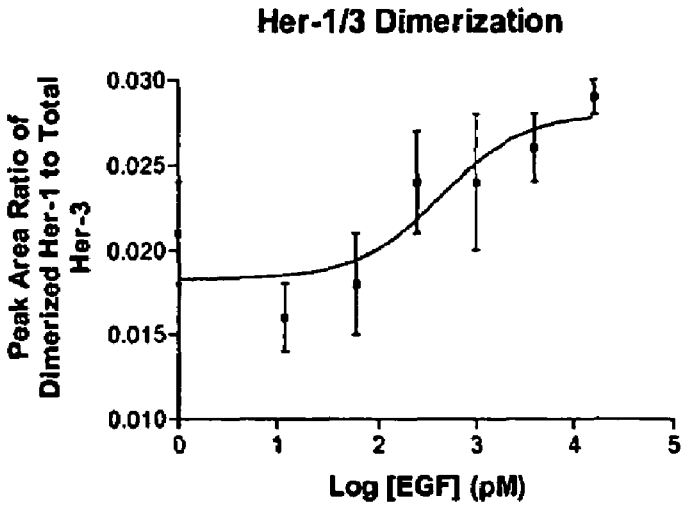
FIGS. 9A and 9B show data on the increases in the numbers of Her1-Her3 heterodimers on 22Rv1 and A549 cells, respectively, with increasing concentrations of epidermal growth factor (EGF).
Figure 9B:
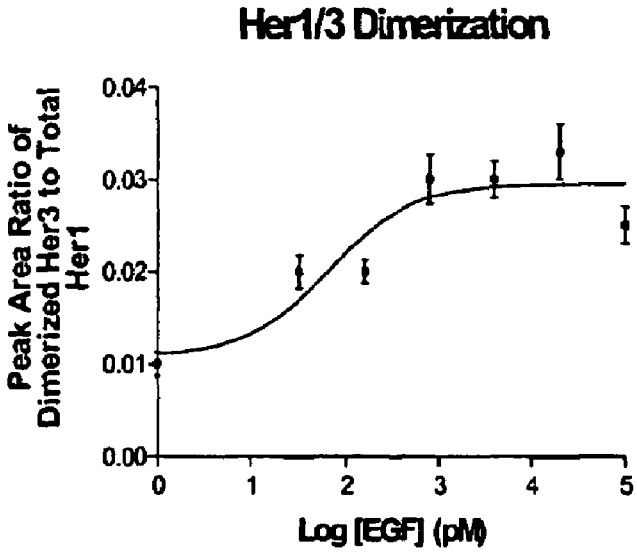

FIGS. 9A and 9B show the increases in the numbers of Her1-Her3 heterodimers on 22Rv1 and A549 cells, respectively, with increasing concentrations of EGF.

Example 6

Occurrence of IGF-1R Heterodimers with Her1, Her2, and Her3 in Breast Tumor Tissue Lysates In this example, cells from 12 different human breast tumor tissues were assayed for the presence of Her1-IGF-1R, Her2-IGF-1R, and Her3-IGF-1R dimers using assays essentially the same as that illustrated in FIG. 4A. Sample Preparation was carried out as follows:

1. Snap frozen tissues are mechanically disrupted at the frozen state by cutting.
2. Transfer tissues to microfuge tube and add 3× tissue volumes of lysis buffer followed by vortexing to disperse tissues in buffer.
3. Incubate on ice for 30 min with intermittent vortexing to mix.
4. Centrifuge at 14,000 rpm, 4° C., for 20 min.
5. Collect supernatants as lysates and determine total protein concentration with BCA assay (Pierce) using a small aliquot.
6. Aliquot the rest for storage at −80° C. until use.

The Assay was Set Up as Follows.

1. The total assay volume is 40 ul.
2. The lysates are tested in serial titration series of 40, 20, 10, 5, 2.5, 1.25, 0.63, 0.31 ug total-equivalents and the volume is adjusted to 30 ul with lysis buffer. Data from the titration series confirm the specificity of the dimerization.
3. A universal antibody mix comprising of all binding compounds and biotin antibody diluted in lysis buffer is used at concentrations given below.

Final Concentrations of Pre-Mixed Antibodies in Reactions:

Pro10_anti-Her-2: 0.1 ug/ml
Pro14_anti-Her-1: 0.1 ug/ml
Pro11_anti-Her-3: 0.1 ug/ml
Pro7_anti-IGF-1R: 0.1 ug/ml
Pro2_anti-phospho-Tyr: 0.2 ug/ml
Biotin_anti-Her-2: 2 ug/ml Procedure:

1. To assay 96-wells, add 5 ul universal reaction mix to 30 ul lysate and incubate for 1 hour at RT.
2. Add 5 ul strepatvidin-derivatized molecular scissor, i.e. cleaving probe (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using: (i) CE equipment: ABI3100, 22 cm capillary, (ii) CE injection conditions: 5 kV, 70 sec, 30° C., and (iii) CE run conditions: 425 sec, 30° C.

Data Analysis:

1. Normalize RFU signal of each molecular tag against CE reference standard 1.
2. Look for titratable signals for each molecular tag. Signals that do not titrate are assumed to be non-specific signals and are not used for data interpretation. A cut off value is determined based on the values from a large set of normal tissues where dimerization signals are expected to be absent or at the lowest. These values also represent the basal level of dimerization on the normal tissues to which tumor tissues are compared.
3. Heterodimerizaion is reported for IGF-1 R with Her-1 or Her-2 or Her-3 as the corresponding specific RFU.

Figure 10A:
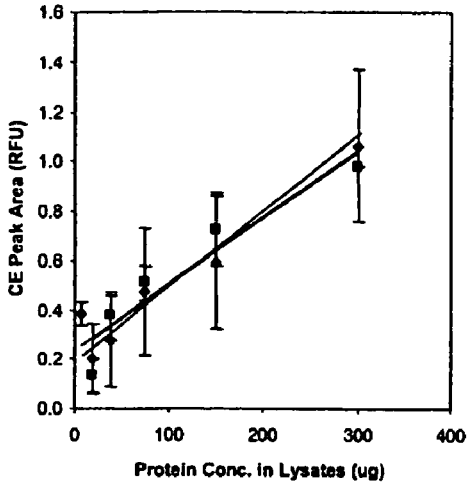
FIGS. 10A-10C show data on the expression of heterodimers of IGF-1R and various Her receptors in frozen samples from human breast tissue.
Figure 10B:
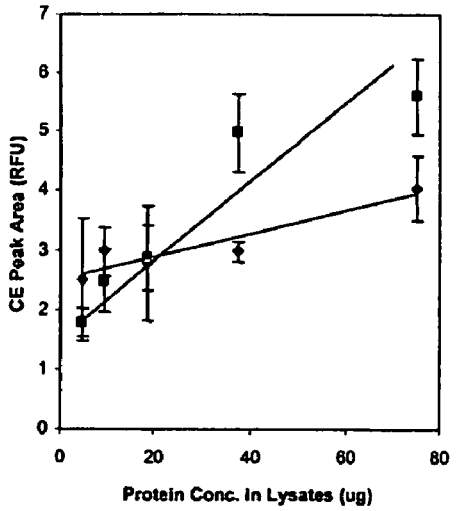
Figure 10C:
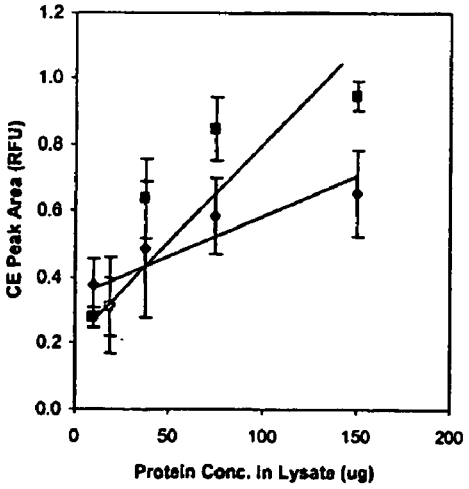

Two out of the twelve breast tumors assayed expressed Her1-IGF-1R, Her2-IGF-1R, and Her3-IGF-1R heterodimers, as shown in FIGS. 10A-C. The lines in each figure panel shows the trend between receptor heterodimer quantity measured and amount of lysate assayed for the two breast tumor samples that were positive for the indicated heterodimers.

Example 7

PI3K/Her-3 Receptor Activation Complex

Figure 11A:
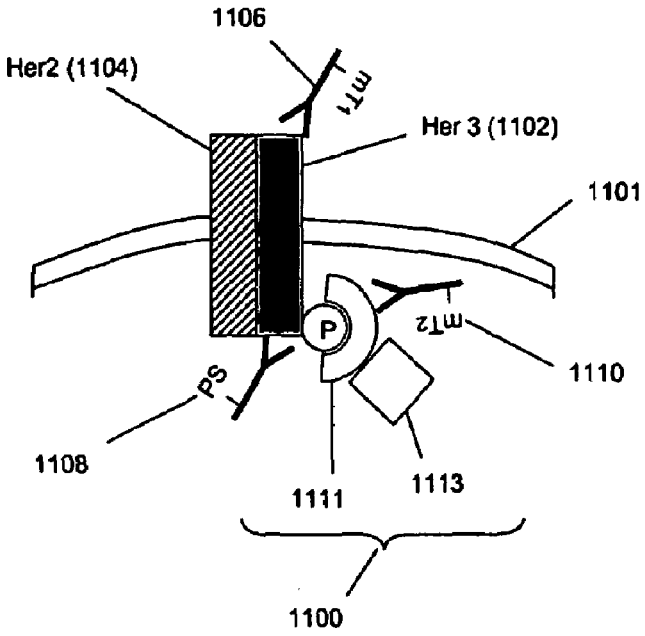
FIGS. 11A-11D illustrate the assay design and experimental results for detecting a PI3 kinase-Her3 receptor activation complex.
Figure 11B:
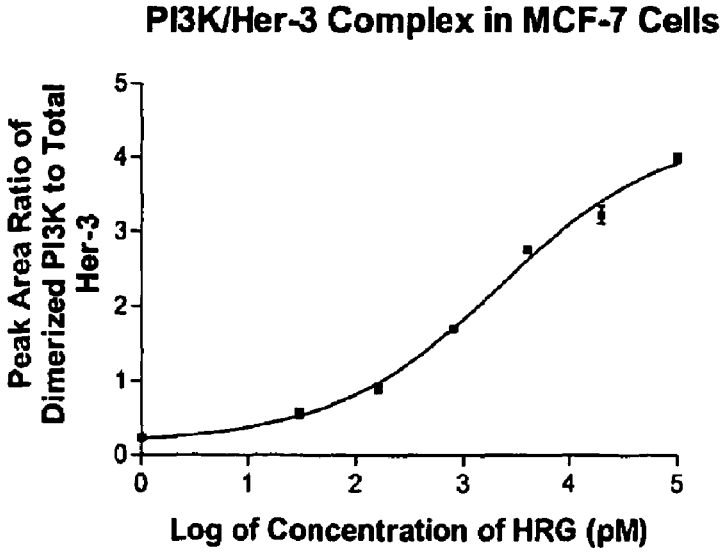
Figure 11C:
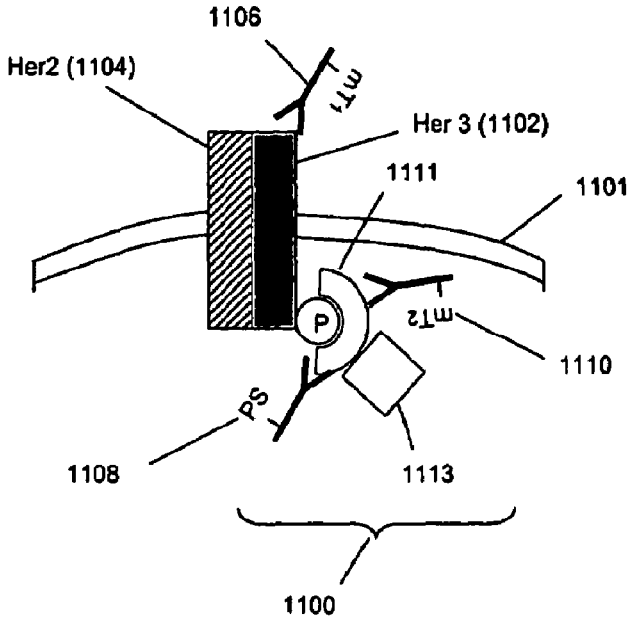

In this example, assays were designed as shown in FIGS. 11A and 11C to measure a receptor complex comprising Her2, Her3, and PI3K in breast cancer cell line, MCF-7. Binding compound (1106) having a first molecular tag ("$mT_1$" in the figure and "eTag1" below) is specific for the extracellular domain of Her3 receptor (1102), binding compound (1110) having a second molecular tag ("mT2" in the figure and "eTag2" below) is specific for the p185 component (1111) of PI3K protein (1100), and cleaving probe (1108) having a photo sensitizer attached (is specific for the intracellular domain of Her3 receptor (1102) where "H2" indicates a Her2 receptor (1104), "H3" indicates a Her3 receptor (1102), "p85" and "p110" are components of PI3 kinase (1100), which binds to a phosphorylation site of H3 (denoted by "P") through its p85 moiety. The two assay designs are similar, except that in the design of FIG. 11A the cleaving probe is specific for the Her3 receptor, and in the design of FIG. 11C, the cleaving probe is specific for the p85 component of PI3 kinase. The assays were carried out as follows.

Sample Preparation:

1. Serum-starve breast cancer cell line culture overnight before use.
2. Stimulate cell lines with HRG in culture media for 10 minutes at 37° C. Exemplary doses of HRG are 0, 0.032, 0.16, 0.8, 4, 20, 100 nM for MCF-7 cells.
3. Aspirate culture media, transfer onto ice, and add lysis buffer (described above to lyse cells in situ).
4. Scrape and transfer lysate to microfuge tube. Incubate on ice for 30 min. Microfuge at 14,000 rpm, 4° C., for 10 min.
5. Collect supernatants as lysates and aliquot for storage at −80° C. until use.

Lysis Buffer (made fresh and stored on ice):

| Final | ul | Stock |
|---|---|---|
| 1% Triton X-100 | 1000 | 10% |
| 20 mM Ths-HCI (pH 7.5) | 200 | 1M |
| 100 mM NaCl | 200 | 5M |
| 50 mM NaF | 500 | 1M |
| 50 mM Na beta-glycerophosphate | 1000 | 0.5M |
| 1 mM $Na_3VO_4$ | 100 | 0.1M |
| 5 mM EDTA | 100 | 0.5M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml Total | |

Assay design: Receptor complex formation is quantified ratiometrically based on the schematics illustrated in each figure. That is, the readout of the assays are the peak ratios of molecular tags, eTag2/eTag1.

The total assay volume is 40 ul. The lysate volume is adjusted to 10 ul with lysis buffer. The antibodies are diluted in lysis buffer up to 20 ul. Typically ~5000 to 500,000 cell-equivalent of lysates is used per reaction.

Procedure: Working concentrations of pre-mixed antibodies prior to adding into reaction: For Her-3/PI3K complex with cleaving probe at Her-3 (the design of FIG. 11A)

eTag1_anti-Her-3 at 10 nM (eTag1 was Pro14 in this assay)
eTag2_anti-PI3K at 10 nM (eTag2 was Pro1 in this assay)
Biotin_anti-Her-3 at 20 nM
Universal Standard US-1 at 700 nM
[The Universal Standard US-1 is BSA conjugated with biotin and molecular tag Pro8, which is used to normalize the amount of streptavidin-photo sensitizer beads in an assay]. The molecular tags were attached directly to antibodies by reacting an NHS-ester of a molecular tag precursor with free amines on the antibodies using conventional techniques, e.g. Hermanson (cited above).

For Her-3/PI3K complex with cleaving probe at PI3K (the design of FIG. 11C):

eTag1_anti-PI3K at 10 nM (eTag1 was Pro1 in this assay)
eTag2_anti-Her-3 at 10 nM (eTag2 was Pro14 in this assay)
Biotin_anti-PI3K at 20 nM
Universal Standard US-1 at 700 nM 9. To assay 96-well filter plate (Millipore MAGVN2250), add 20 ul antibody mix to 10 ul lysate and incubate for 1 hour at 4° C.
10. Add 10 ul streptavidin-derivatized cleaving probe (final 4 ug/well) to assay well and incubate for 40 min.
11. Add 200 ul wash buffer and apply vacuum to empty.
12. Add 30 ul illumination buffer and illuminate.
13. Transfer 10 ul of each reaction to CE assay plate for analysis.

Figure 11D:
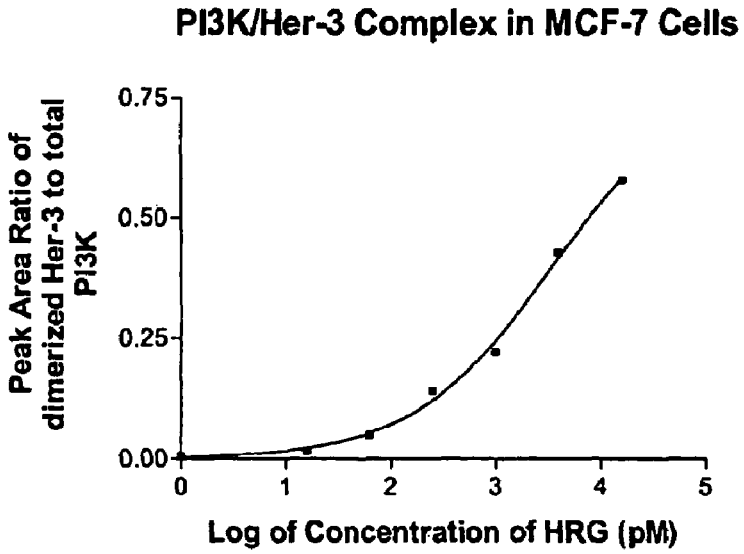

Data Analysis:

1. Normalize relative fluorescence units (RFU) signal of each molecular tag against that of internal Universal Standard US-1.
2. Subtract RFU of "no lysate" background control from corresponding normalized eTag reporter signals.
3. Report receptor complex formation as the ratiometric of normalized eTag2/eTag1 signal (shown in FIGS. 11B and 11D).

Example 8

Shc/Her-3 Receptor-Adaptor Interaction

Figure 12A:
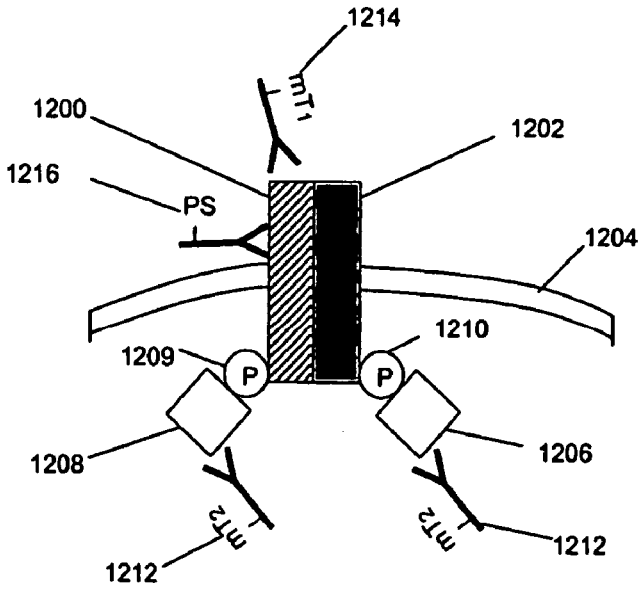
FIGS. 12A-12D illustrate the assay design and experimental results for detecting a Shc/Her3 receptor-adaptor complex.
Figure 12B:
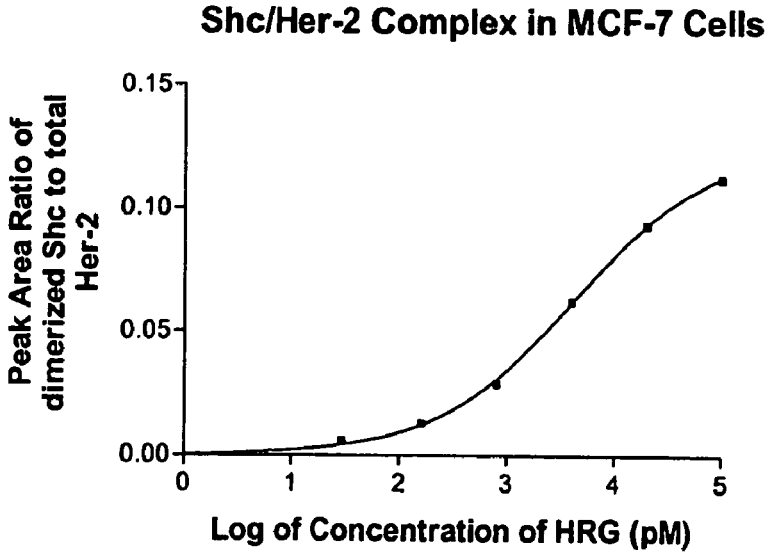
Figure 12C:
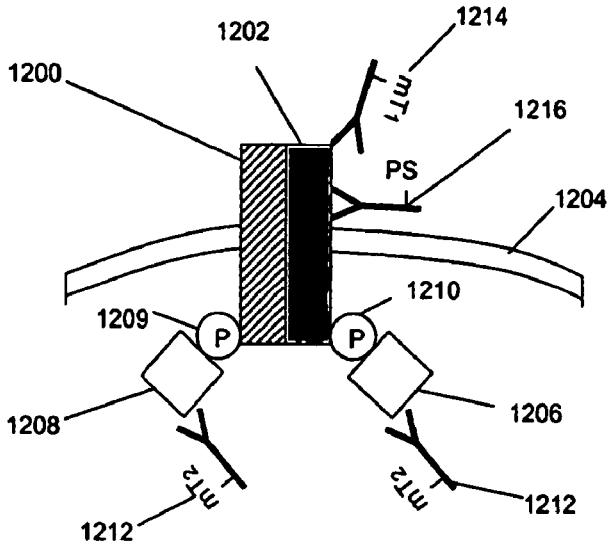

In this example, an assays were designed as shown in FIGS. 12A and 12C. In FIG. 12A, Her2 receptor (1200) and Her3 receptor (1202) form a dimer in cell surface membrane (1204) and each receptor is represented as having phosphorylated sites (1209 and 1210). Shc proteins (1206 and 1208) bind to phosphylation sites (1210) and (1209), respectively. A first binding compound (1214) and cleaving probe (1216) are specific for different antigenic determinants of the extracellular domain of Her2 receptor (1200). A second binding compound (1212) is specific for Shc proteins (1206 and 1208). The assay designs of FIGS. 12A and 12C are similar, except that in the design of FIG. 12A the cleaving probe is specific for the Her2 receptor, and in the design of FIG. 12C, the cleaving probe is specific for the Her3 receptor. Thus, in the former case, total Her2 receptor is measured, whereas in the latter case total Her3 receptor is measured. The assays were carried out as follows. Sample preparation was carried out as above (Example 7).

Figure 12D:
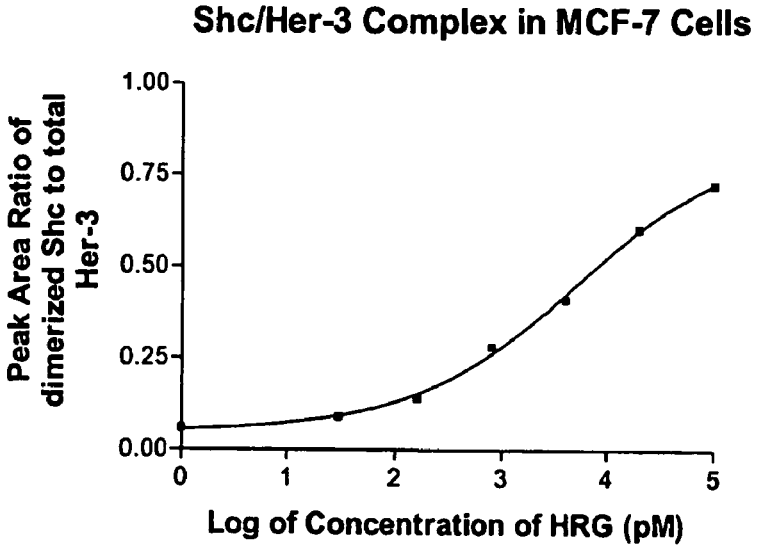

Assay design: Receptor complex formation is quantified ratiometrically based on the schematics illustrated in each figure. That is, in FIGS. 12B and 12D the readout of the assays are the peak ratios of $mT_2/mT_1$ as a function of HRG concentration.

The total assay volume is 40 ul. The lysate volume is adjusted to 10 ul with lysis buffer. The antibodies are diluted in lysis buffer up to 20 ul. Typically about 5000 to 500,000 cell-equivalent of lysates is used per reaction.

Procedure: Working concentrations of pre-mixed antibodies prior to adding into reaction:

For Her-3/Shc complex with cleaving probe at Her-3 (the design of FIG. 12B):

eTag1_anti-Her-3 at 10 nM (eTag1 was Pro14 in this assay)
eTag2_anti-Shc at 10 nM (eTag2 was Pro12 in this assay)
eTag3_anti-phospho-Tyr at 10 nM (eTag3 was Pro2 in this assay)
Biotin_anti-Her-3 at 20 nM
Universal Standard US-1 at 700 nM For Her-2/Shc complex with cleaving probe at Her-2 (the design of 12A):

eTag1_anti-Her-2 at 10 nM (eTag1 was Pro14 in this assay)
eTag2_anti-Shc at 10 nM (eTag2 was Pro 12 in this assay)
eTag3_anti-phospho-Tyr at 10 nM (eTag3 was Pro2 in this assay)
Biotin_anti-Her-2 at 20 nM
Universal Standard US-1 at 700 nM 1. To assay 96-well filter plate (Millipore MAGVN2250), add 20 ul antibody mix to 10 ul lysate and incubate for 1 hour at 4° C.
2. Add 10 ul streptavidin-derivatized cleaving probe (final 4 ug/well) to assay well and incubate for 40 min.
3. Add 200 ul wash buffer and apply vacuum to empty.

4. Add 30 ul illumination buffer and illuminate.
5. Transfer 10 ul of each reaction to CE assay plate for analysis.

Data Analysis:

1. Normalize relative fluorescence units (RFU) signal of each molecular tag against that of internal Universal Standard US-1.
2. Subtract RFU of "no lysate" background control from corresponding normalized signals for molecular tags.
3. Report receptor complex formation as the ratiometric of normalized $mT_2/mT_1$ signals (shown in FIGS. 12B and 12D) and receptor phosphorylation (data not shown) as mT3/mT1 signals.

Example 9

Figure 13:
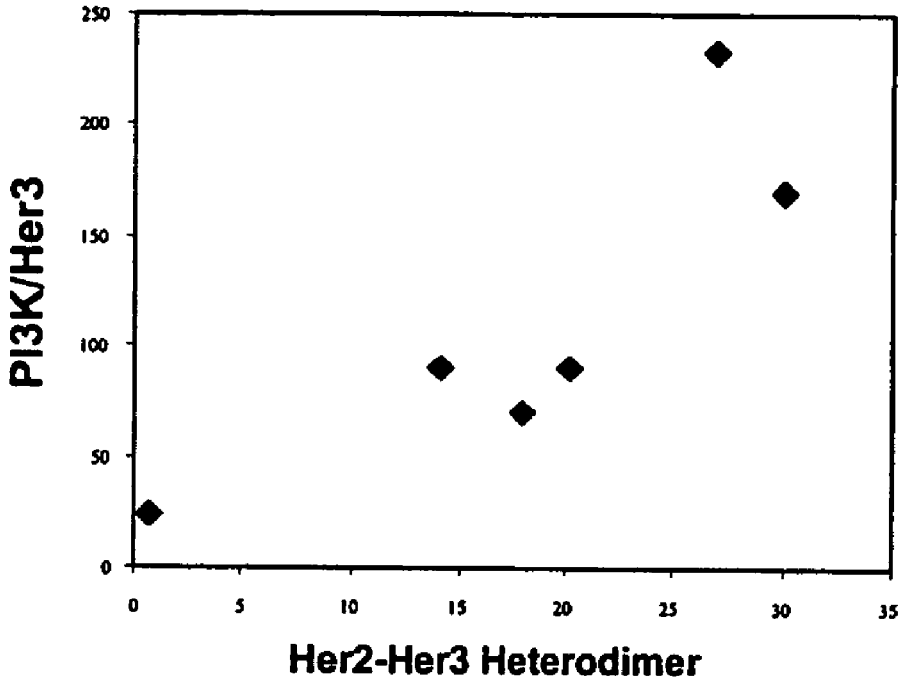
FIG. 13 shows data for a correlation between expression of Her2-Her3 heterodimers and PI3K//Her3 complexes in tumor cells.

Correlation Between Her2-Her3 Heterodimer Measurements and Her3-PI3K Complex Measurements in Breast Tumor Samples In this example, human breast tumor samples were separately assayed using the methods described above to determine the amounts of Her2-Her3 heterodimers and the amounts of Her3-PI3K complex. FIG. 13 illustrates data obtained from such assays, which shows that the two measurements are correlated.

Example 10

Expression of Her1-Her2 and Her2-Her3 Heterodimers in Breast Tumor Tissue Lysates and Normal Tissue Lysates Frozen human breast tumor tissue samples and normal tissue samples were obtained from the William Bainbridge Genomic Foundation (Bainbridge Island, Wash.). Assays having a format as shown in FIG. 3E were performed on 32 tumor tissue samples and 30 normal tissue samples. Tumor tissues consisted of a mixture of tumor and normal cells that varied from about 25 percent to over 90 percent according to pathology data supplied with the tissues by the vendor. Samples were prepared and the assays carried out essentially as described for Examples 2 and 6. Data is reported as peak area or intensity of the separated molecular tag released from the binding compound specifically bound to the receptor opposite the cleaving probe, i.e. the molecular tag corresponding to "$mT_1$" in FIG. 3E. No attempt was made to normalize the signals generated according to percentage tumor cells in a sample.

Figure 14B:
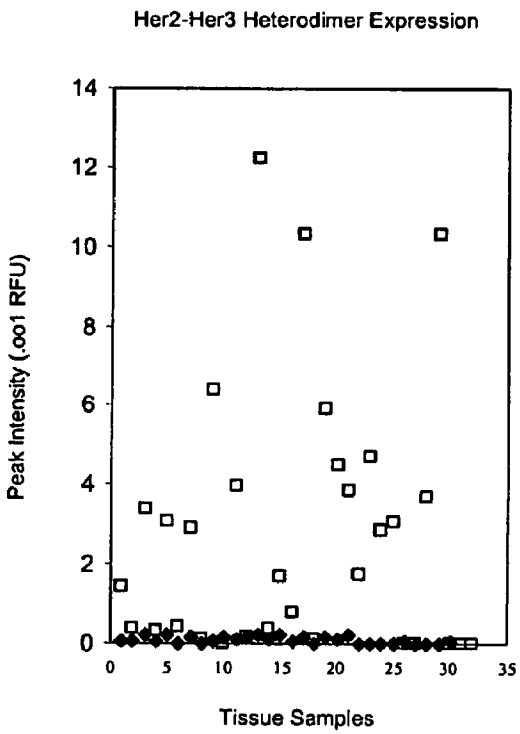
FIGS. 14A-14B show measurements of Her1-Her2 and Her2-Her3 receptor dimer populations obtained from normal breast tissue samples and from breast tumor tissue samples.
Figure 14A:
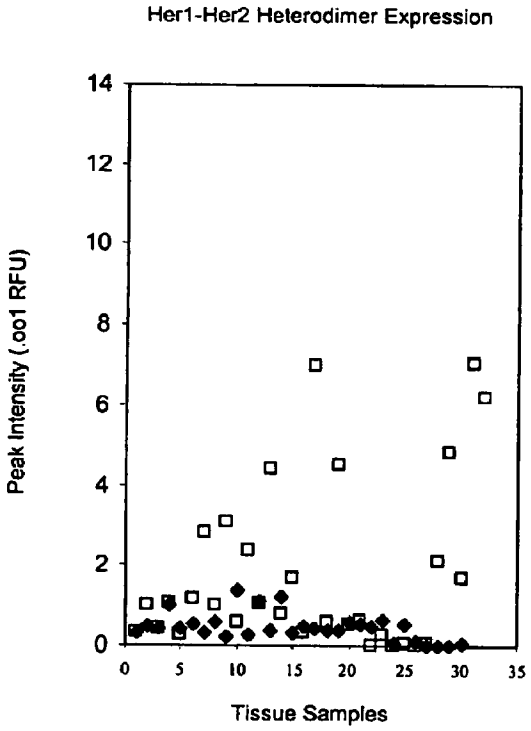

The data from these measurements are shown in FIG. 14A (Her1-Her2 heterodimer measurements) and FIG. 14B (Her2-Her3 heterodimer measurements), where the open squares (□) indicate measurements on tumor tissues and the solid diamonds (◆) indicate measurements on normal tissues. The data show that tumor cells in substantial fractions of the tumor tissue samples express large amounts of Her1-Her2 heterodimers and Her2-Her3 heterodimers relative to those expressed in the cells of the normal tissue samples.

Example 11

Measurement of Receptor Dimers in Formalin Fixed Paraffin Embedded Tissue Samples In this example, model fixed tissues made from pelleted cell lines were assayed for the presence of Her receptor dimers. The assay design for heterodimers was essentially the same as that described in FIG. 4A, with exceptions as noted below. That is, four components are employed: (i) a cleaving probe comprising a biotinylated monoclonal antibody conjugated to a cleavage-inducing moiety (in this example, a photo sensitizer-derivatized streptavidin, as illustrated in FIG. 3E) and specific for one of the receptors of the dimer, (ii) a monoclonal antibody derivatized with a first molecular tag and specific for the same receptor as the cleaving probe, (iii) a monoclonal antibody derivatized with a second molecular tag and specific for the receptor opposite to that the cleaving probe is specific for, and (iv) a monoclonal antibody derivatized with a third molecular tag and specific for an intracellular phosphorylated tyrosine. The assay design for homodimers was essentially the same as that described in FIG. 1D, with exceptions as noted below.

In each case, model fixed tissues were prepared as follows: cells grown on tissue culture plates were stimulated with either EGF or HRG as described in the prior examples, after which they were washed and removed by scrapping. The removed cells were centrifuged to form a pellet, after which formalin was added and the mixture was incubated overnight at 4° C. The fixed pellet was embedded in paraffin using a Miles Tissue Tek III Embedding Center, after which 10 μm tissue sections were sliced from the pellet using a microtome (Leica model 2145). Tissue sections were placed on positively charged glass microscope slides (usually multiple tissue sections per slide) and baked for 1 hr at 60° C.

Tissue sections on the slides were assayed as follows: Tissue sections on a slide were de-waxed with EZ-Dewax reagent (Biogenex, San Ramon, Calif.) using the manufacturer's recommended protocol. Briefly, 500 μL EZ-Dewax was added to each tissue section and the sections were incubated at RT for 5 min, after which the slide was washed with 70% EtOH. This step was repeated and the slide was finally rinsed with deionized water, after which the slide was incubated in water at RT for 20 min. The slide was then immersed into a 1× Antigen Retrieval solution (Biogenesis, Brentwood, N.H.) at pH 10, after which it was heated for 15 min in a microwave oven (5 min at high power setting followed by 10 min at a low power setting). After cooling to RT (about 45 min), the slide was placed in a water bath for 5 min, then dried. Tissue sections on the dried slide were circled with a hydrophobic wax pen to create regions capable of containing reagents placed on the tissue sections (as illustrated in FIGS. 1H-1I), after which the slide was washed three times in 1×Perm/Wash (BD Biosciences). To each section 50-100 μl blocking buffer was added, and the slide was placed in a covered humidified box containing deionized water for 2 hr at 4° C., after which the blocking buffer was removed from each section by suction. (Blocking buffer is 1×Perm/Wash solution with protease inhibitors (Roche), phosphatase inhibitors (sodium fluoride, sodium vanadate, β-glycerol phosphate), and 10% mouse serum). To each section 40-50 μL of antibody mix containing binding compounds and cleaving probe was added (each at 5 μg/mL, except that biotin-Ab5 (anti-Her1) was at 10 μg/mL in the Her1-Her2 assay), and the slide was placed in a humidified box overnight at 4° C. The sections were then washed three times with 100 μL Perm/Wash containing protease and phosphatase inhibitors, after which 50 μL of photosensitizer in 1×Perm/Wash solution (containing protease and phosphatase inhibitors) was added. The slide was then incubated for 1-1.5 hr at 4° C. in the dark in a humidified box, after which the photo sensitizer was removed by suction while keeping the slide in the dark. While remaining in the dark, the slide was then immersed in 0.01×PBS and incubated on ice for 1 hr. The slide was remove from the PBS, dried, and to each section, 40-50 μL 0.01×PBS with 2 pM fluorescein was added, after which it was illuminated with a high power laser diode (GaAIAs IR emitter, model OD-880W, OPTO DIODE CORP, Newbury Park, Calif.) for 1 hr. The fluorescein acts as a standard to assist in correlating peaks in an electropherogram with molecular tags. After illumination, the solution covering each tissue section was mixed by gentle pipeting and transferred to a CE plate for analysis on an Applied Biosystems (Foster City, Calif.) model 3100 capillary electrophoresis instrument.

Figure 15A:
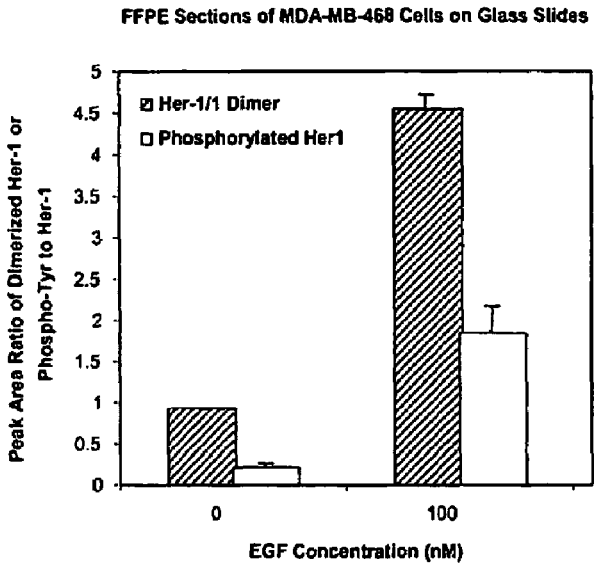
FIGS. 15A-15G show measurements of Her1-Her1 and Her2-Her2 homodimers and Her1-Her2 and Her2-Her3 heterodimers in sections of fixed pellets of cancer cell lines.

FIG. 15A shows data from analysis of Her1-Her1 homodimers and receptor phosphorylation in sections from fixed pellets of breast adenocarcinoma cell line, MDA-MB-468 (ATCC accession no. HTB-132), prepared from either non-stimulated cells or cells stimulated with 100 nM EGF. Biotinylated anti-Her1 monoclonal antibody (Labvision) at 2 μg/mL was use as the primary antibody of the cleaving probe (for cleavage methylene-blue derivatized streptavidin (described above) was attached through the biotin). Pro10-derivatized anti-Her1 monoclonal antibody (Labvision) at 2 μg/mL was used to measure homodimerized Her1. Pro1-derivatized anti-Her1 monoclonal antibody (Labvision) at 0.8 μg/mL was used to measure total Her1. Unlabeled antibody Ab-5 was also included in the reactions at 3.2 μg/mL. Pro2-derivatized monoclonal antibody (anti-phosphorylated-Tyr, Cell Signaling) at 0.5 μg/mL was used to measure intracellular phosphorylation. The data from fixed tissue measurements confirm and are consistent with measurements on cell lysates that show increases in Her1-Her1 homodimer expression and intracellular phosphoryation due to EGF stimulation.

Figure 15B:
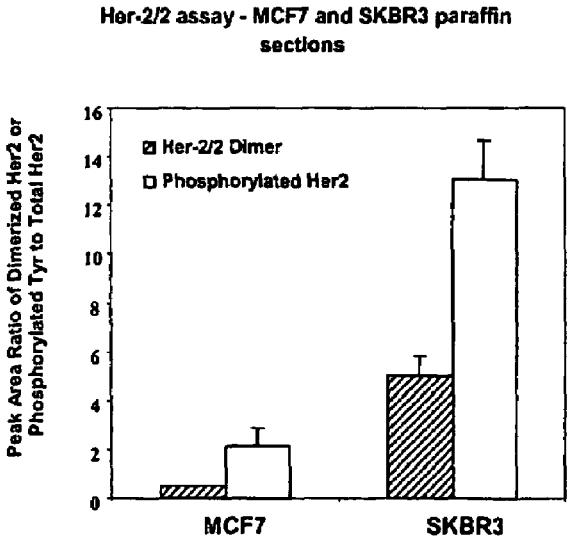

FIG. 15B shows data from analysis of Her2-Her2 homodimers and receptor phosphorylation in sections from fixed pellets of breast cancer cell lines MCF-7 and SKBR-3. All monoclonal antibodies used as cleaving probes or binding compounds were used at concentrations of 5 μg/mL. In order to generate better cleavage, in this assay two cleaving probes were employed, one directed to an extracellular antigenic determinant of Her2 and one directed to an intracellular antigenic determinant of Her2. The data from fixed tissue measurements confirm that SKBR3 cells express higher levels of Her2-Her2 homodimers than MCF-7 cells.

Figure 15C:
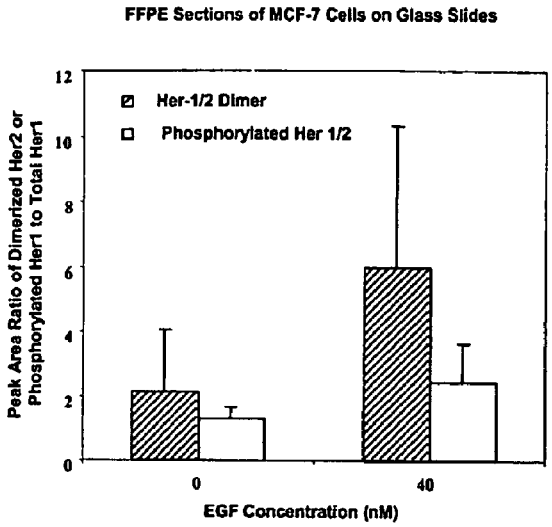

FIG. 15C shows data from analysis of Her1-Her2 heterodimers and receptor phosphorylation in sections from fixed pellets of breast adenocarcinoma cell line, MCF-7, prepared from either non-stimulated cells or cells stimulated with 40 nM EGF. Two cleaving probes were employed one comprising anti-Her1 monoclonal antibody (at 5 μg/mL) and the other comprising anti-Her1 monoclonal antibody (at 10 μg/mL) (both from Labvision) in order to increase the rate at which molecular tags were released. The data show that increases in Her1-Her2 heterodimer expression due to EGF stimulation is detected in fixed tissue.

Figure 15D:
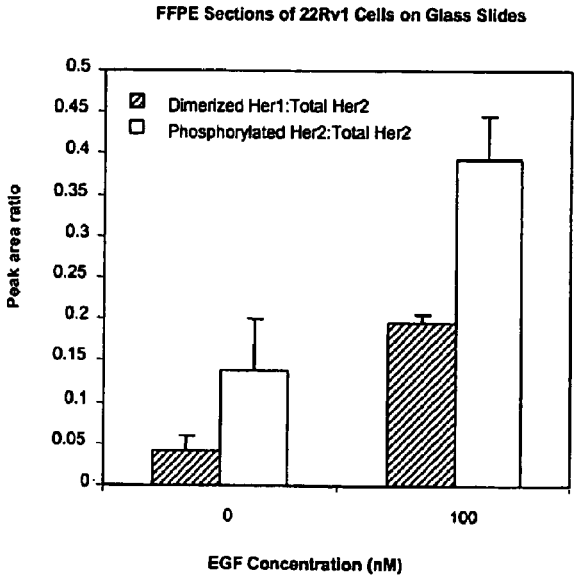

FIG. 15D shows data from analysis of Her1-Her2 heterodimers and receptor phosphorylation in sections from fixed pellets of breast adenocarcinoma cell line, 22Rv1, prepared from either non-stimulated cells or cells stimulated with 100 nM EGF. Again, measurements on fixed tissues demonstrates the up-regulation of Her1-Her2 dimers and Her receptor phosphorylation in response to treatment with EGF.

Figure 15E:
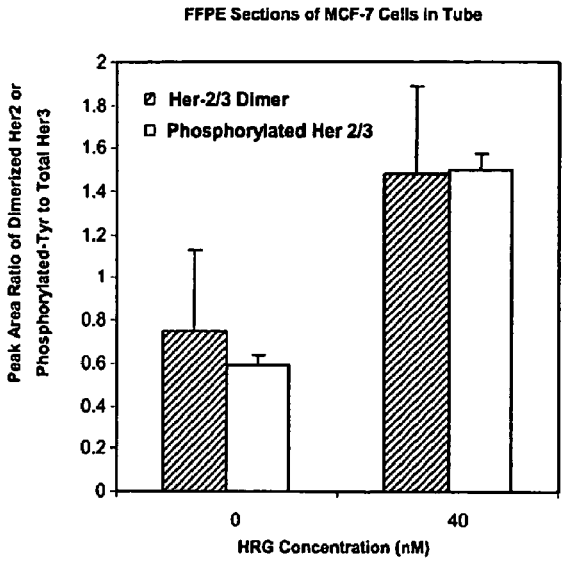

FIG. 15E shows data from analysis of Her2-Her3 heterodimers and receptor phosphorylation in sections from fixed pellets of breast adenocarcinoma cell line, MCF-7, prepared from either non-stimulated cells or cells stimulated with 40 nM HRG. In this example, binding reactions and cleavage reactions took place in tubes containing sections, rather than microscope slides. Otherwise, the protocol was essentially the same as that for detecting the Her1-Her2 dimers. The data show that increases in Her2-Her3 heterodimer expression due to HRG stimulation is detected in fixed tissue.

Figure 15F:
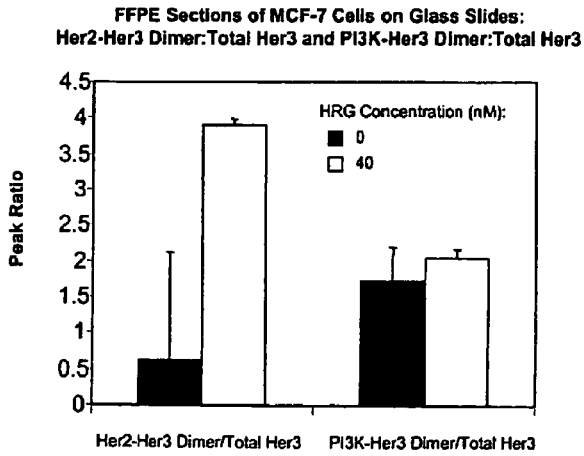

FIG. 15F shows data from analysis of Her2-Her3 heterodimers and PI3K-Her3 dimers in sections from fixed pellets of MCF-7 cells either non-stimulated or stimulated with 40 nM HRG. The assay design for PI3K-Her3 was essentially as described in FIG. 11A. The above fixation protocol was followed in both cases, except that neither sample was treated with antigen retrieval reagents. The data show that Her2-Her3 dimers increased with treatment by HRG, but that the amount of PI3K-Her3 dimer remained essentially unchanged.

Figure 15G:
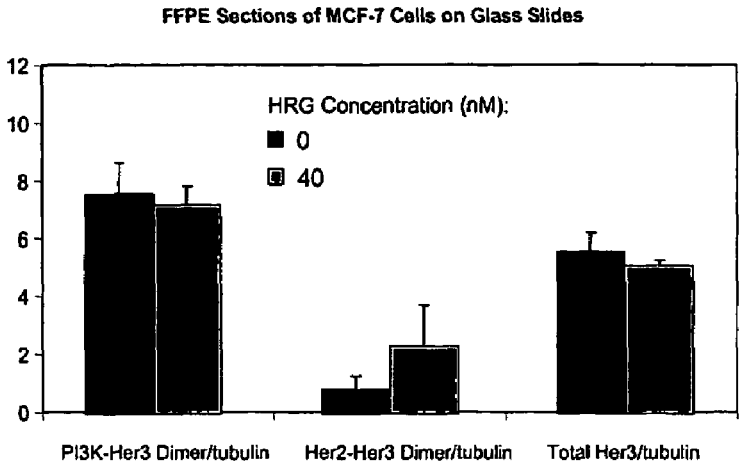

FIG. 15G shows data from analysis of total PI3K, total Her2-Her3 dimer, and total Her3 all relative to amount of tubulin. Tubulin was measured in a conventional sandwich-type assay employing a cleavage probe and a binding compound with a molecular tag. Tubulin was measured to test procedures for normalizing dimer measurement against a target representative of total cell number in a sample, which may be required for measurements on samples with heterogeneous cell types. The data show that the ratios of PI3K-Her3 and Her2-Her3 to tubulin are qualitatively the same as the measurements directly on PI3K-Her3 and Her2-Her3.

What is claimed is:

1. A method for detecting in a biological sample the presence or amount of a receptor complex comprising a phosphatidylinositol-3-kinase (PI3K) protein and a receptor, comprising: a. contacting with the sample a binding compound having a molecular tag attached thereto by a cleavable linkage and a cleaving probe having a cleavage inducing-moiety with an effective proximity, wherein the binding compound specifically binds either the PI3K or the receptor and the cleaving probe specifically binds an opposite member of the receptor complex from that bound by the cleaving probe; b. cleaving the cleavable linker of the binding compound within the effective proximity of the cleavage-inducing moiety of the cleaving probe, thereby releasing the molecular tag; and c. identifying the released molecular tag to determine the presence or amount of the receptor complex comprising the PI3K and the receptor in the sample.

2. The method of claim 1, wherein the receptor is Her1.

3. The method of claim 1, wherein the binding compound comprises an anti-PI3K antibody.

4. The method of claim 1, wherein the binding compound comprises an anti-Her3 antibody.

5. The method of claim 1, wherein the cleaving probe comprises an anti-PI3K antibody.

6. The method of claim 1, wherein the cleaving probe comprises an anti-Her3 antibody.

7. The method of claim 1, wherein the biological sample comprises cancer cells.

8. The method of claim 7, wherein the cancer cells are obtained from a patient.

9. The method of claim 8, wherein the biological sample is obtained by a biopsy of the cancer.

10. The method of claim 8, wherein the biological sample is obtained by purifying circulating cancer cells from the patient's blood.

11. The method of claim 7, wherein the cancer is a breast cancer.

12. The method of claim 1, wherein the step of detecting is preceded by electrophoretically separating the molecular tag.

13. The method of claim 1, wherein the cleavage-inducing moiety is a photosensitizer.

*14. The method of claim 1, wherein the receptor is Her2.*

*15. The method of claim 1, wherein the receptor is Her3.*

*16. The method of claim 1, wherein the binding compound comprises an anti-Her1 antibody.*

*17. The method of claim 1, wherein the binding compound comprises an anti-Her2 antibody.*

*18. The method of claim 1, wherein the cleaving probe comprises an anti-Her1 antibody.*

*19. The method of claim 1, wherein the cleaving probe comprises an anti-Her2 antibody.*

*20. The method of claim 7, wherein the cancer is a lung cancer.*

* * * * *